United States Patent
Pate et al.

(10) Patent No.: US 11,612,432 B2
(45) Date of Patent: Mar. 28, 2023

(54) SYSTEMS, DEVICES, AND METHODS FOR FORMING AN ANASTOMOSIS

(71) Applicant: Alleviant Medical, Inc., Austin, TX (US)

(72) Inventors: Thomas D. Pate, Austin, TX (US); Zachary R. Berman, Austin, TX (US)

(73) Assignee: Alleviant Medical, Inc., Austin, TX (US)

( * ) Notice: Subject to any disclaimer, the term of this patent is extended or adjusted under 35 U.S.C. 154(b) by 0 days.

(21) Appl. No.: 17/730,731

(22) Filed: Apr. 27, 2022

(65) Prior Publication Data

US 2022/0249160 A1 Aug. 11, 2022

Related U.S. Application Data

(63) Continuation of application No. 17/019,042, filed on Sep. 11, 2020.

(60) Provisional application No. 62/971,357, filed on Feb. 7, 2020, provisional application No. 62/900,034, filed on Sep. 13, 2019.

(51) Int. Cl.
    *A61B 18/14* (2006.01)
    *A61B 18/00* (2006.01)

(52) U.S. Cl.
    CPC ........ *A61B 18/1492* (2013.01); *A61B 2018/00351* (2013.01); *A61B 2018/00577* (2013.01); *A61B 2218/002* (2013.01)

(58) Field of Classification Search
    CPC .......... A61B 1/11; A61B 2017/1139; A61B 2017/00247; A61B 2018/00422
    See application file for complete search history.

(56) References Cited

U.S. PATENT DOCUMENTS

| | | |
|---|---|---|
| 5,403,338 A | 4/1995 | Milo |
| 5,725,552 A | 3/1998 | Kotula et al. |
| 5,951,576 A | 9/1999 | Wakabayashi |
| 6,699,256 B1 | 3/2004 | Logan et al. |
| 7,048,733 B2 | 5/2006 | Hartley et al. |
| 7,056,294 B2 | 6/2006 | Khairkhahan et al. |
| 7,112,197 B2 | 9/2006 | Hartley et al. |
| 7,340,307 B2 | 3/2008 | Maguire et al. |

(Continued)

FOREIGN PATENT DOCUMENTS

| | | |
|---|---|---|
| EP | 3 154 450 A0 | 4/2017 |
| EP | 2 673 038 B1 | 7/2017 |

(Continued)

OTHER PUBLICATIONS

International Search Report dated Jan. 19, 2021, for PCT Application No. PCT/US2020/050533, filed on Sep. 11, 2020, 6 pages.

(Continued)

*Primary Examiner* — Linda C Dvorak
*Assistant Examiner* — Christine A Dedoulis
(74) *Attorney, Agent, or Firm* — Cooley LLP

(57) ABSTRACT

Disclosed herein are systems, devices, and methods for treating heart failure. In some variations, a catheter for forming an anastomosis in a heart may comprise a first catheter comprising an electrode. A second catheter may be slidably disposed within the first catheter. The second catheter may comprise a barb and a dilator comprising a mating surface configured to engage the electrode.

27 Claims, 48 Drawing Sheets

(56) References Cited

U.S. PATENT DOCUMENTS

| | | | |
|---|---|---|---|
| 7,729,738 | B2 | 6/2010 | Flaherty et al. |
| 7,771,442 | B2 | 8/2010 | Shriver |
| 7,799,041 | B2 | 9/2010 | Beane et al. |
| 7,935,129 | B2 | 5/2011 | Gifford, III et al. |
| 7,947,040 | B2 | 5/2011 | Davies et al. |
| 8,091,556 | B2 | 1/2012 | Keren et al. |
| 8,096,990 | B2 | 1/2012 | Swanson et al. |
| 8,114,069 | B2 | 2/2012 | Sliwa, Jr. et al. |
| 8,147,424 | B2 | 4/2012 | Kassab et al. |
| 8,157,860 | B2 | 4/2012 | McNamara et al. |
| 8,192,425 | B2 | 6/2012 | Mirza et al. |
| 8,226,670 | B2 | 7/2012 | Beane et al. |
| 8,308,723 | B2 | 11/2012 | Kulesa et al. |
| 8,417,321 | B2 | 4/2013 | Saadat et al. |
| 8,496,655 | B2 | 7/2013 | Epp et al. |
| 8,679,107 | B2 | 3/2014 | Mirza et al. |
| 8,679,138 | B2 | 3/2014 | Beane et al. |
| 8,771,305 | B2 | 7/2014 | Shriver |
| 8,882,697 | B2 | 11/2014 | Celermajer et al. |
| 8,961,550 | B2 | 2/2015 | Lenker et al. |
| 9,055,959 | B2 | 6/2015 | Vaska et al. |
| RE45,638 | E | 8/2015 | Tartaglia et al. |
| 9,101,375 | B2 | 8/2015 | Biadillah et al. |
| 9,168,085 | B2 | 10/2015 | Juzkiw et al. |
| 9,277,957 | B2* | 3/2016 | Long ................ A61B 18/1206 |
| 9,526,573 | B2 | 12/2016 | Lopes et al. |
| 9,597,146 | B2 | 3/2017 | Davies et al. |
| 9,629,715 | B2 | 4/2017 | Nitzan et al. |
| 9,724,126 | B2 | 8/2017 | Gerber et al. |
| 9,775,636 | B2 | 10/2017 | Fazio et al. |
| 9,814,483 | B2 | 11/2017 | Vardi |
| 10,271,894 | B2 | 4/2019 | Woo et al. |
| 10,292,690 | B2 | 5/2019 | Celermajer et al. |
| 10,413,286 | B2 | 9/2019 | McNamara et al. |
| 11,304,753 | B2 | 4/2022 | Pate et al. |
| 2002/0082614 | A1 | 6/2002 | Logan et al. |
| 2002/0128672 | A1 | 9/2002 | Dinger et al. |
| 2005/0159738 | A1 | 7/2005 | Visram et al. |
| 2006/0111704 | A1 | 5/2006 | Brenneman et al. |
| 2006/0210605 | A1 | 9/2006 | Chang et al. |
| 2008/0004485 | A1 | 1/2008 | Moreschi |
| 2010/0114140 | A1 | 5/2010 | Chanduszko et al. |
| 2010/0160725 | A1 | 6/2010 | Kiser et al. |
| 2011/0270239 | A1 | 11/2011 | Werneth |
| 2011/0306959 | A1 | 12/2011 | Kellerman et al. |
| 2012/0165812 | A1* | 6/2012 | Christian ............ A61B 18/1492 606/41 |
| 2013/0310804 | A1 | 11/2013 | Jabba et al. |
| 2014/0046356 | A1 | 2/2014 | Abdul-Karim |
| 2014/0128796 | A1 | 5/2014 | Keren et al. |
| 2014/0236207 | A1 | 8/2014 | Makower et al. |
| 2014/0277045 | A1* | 9/2014 | Fazio ................ A61B 17/32053 606/170 |
| 2014/0350565 | A1 | 11/2014 | Yacoby et al. |
| 2015/0031959 | A1 | 1/2015 | Beane et al. |
| 2015/0173794 | A1 | 1/2015 | Tsao |
| 2015/0157353 | A1 | 6/2015 | Lenker et al. |
| 2015/0223839 | A1 | 8/2015 | Spence et al. |
| 2015/0359556 | A1 | 12/2015 | Vardi |
| 2016/0000499 | A1 | 1/2016 | Lennox et al. |
| 2016/0000501 | A1 | 1/2016 | Davies et al. |
| 2016/0100859 | A1 | 4/2016 | Sapir et al. |
| 2016/0220245 | A1* | 8/2016 | Hausen ............. A61B 17/1227 |
| 2016/0270810 | A1* | 9/2016 | Vardi ............... A61B 17/32053 |
| 2017/0042572 | A1 | 2/2017 | Jimenez et al. |
| 2017/0113026 | A1 | 4/2017 | Finch |
| 2018/0177516 | A1* | 6/2018 | Vardi ............. A61B 17/320016 |
| 2019/0029705 | A1 | 1/2019 | Vardi et al. |
| 2019/0216528 | A1 | 7/2019 | Woo et al. |
| 2019/0231424 | A1 | 8/2019 | Davies et al. |
| 2019/0239924 | A1 | 8/2019 | Urbanski et al. |
| 2019/0269392 | A1 | 9/2019 | Celermajer et al. |
| 2019/0374254 | A1* | 12/2019 | Arevalos .......... A61B 17/32002 |
| 2019/0374281 | A1 | 12/2019 | Davies et al. |
| 2021/0077186 | A1 | 3/2021 | Pate et al. |

FOREIGN PATENT DOCUMENTS

| | | |
|---|---|---|
| EP | 3 329 860 A1 | 6/2018 |
| EP | 3 275 390 B1 | 6/2019 |
| GB | 2498162 A | 7/2013 |
| WO | WO-89/07422 A1 | 8/1989 |
| WO | WO-01/15618 A2 | 3/2001 |
| WO | WO-01/15618 A3 | 3/2001 |
| WO | WO-03/077733 A2 | 9/2003 |
| WO | WO-03/077733 A3 | 9/2003 |
| WO | WO-2010/024761 A1 | 3/2010 |
| WO | WO-2015/085094 A1 | 6/2015 |
| WO | WO-2015/192109 A1 | 12/2015 |
| WO | WO-2017/118920 A1 | 7/2017 |
| WO | WO-2018/148456 A1 | 8/2018 |
| WO | WO-2019/109013 A1 | 6/2019 |

OTHER PUBLICATIONS

Non-Final Office Action dated Nov. 3, 2021, for U.S. Appl. No. 17/354,855, filed Jun. 22, 2021, 19 pages.

Notice of Allowance dated Mar. 7, 2022, for U.S. Appl. No. 17/354,855, filed Jun. 22, 2021, 11 pages.

Written Opinion of the International Searching Authority dated Jan. 19, 2021, for PCT Application No. PCT/US2020/050533, filed on Sep. 11, 2020, 11 pages.

* cited by examiner

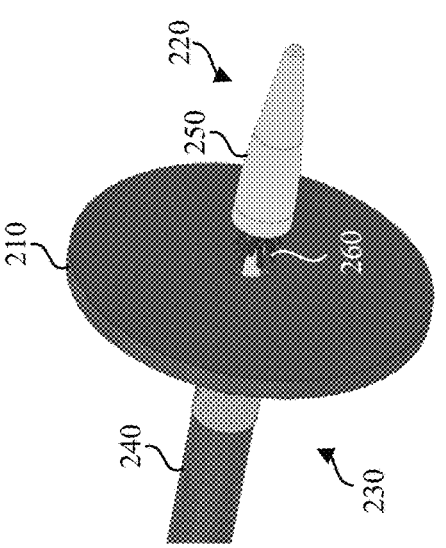
FIG. 2A
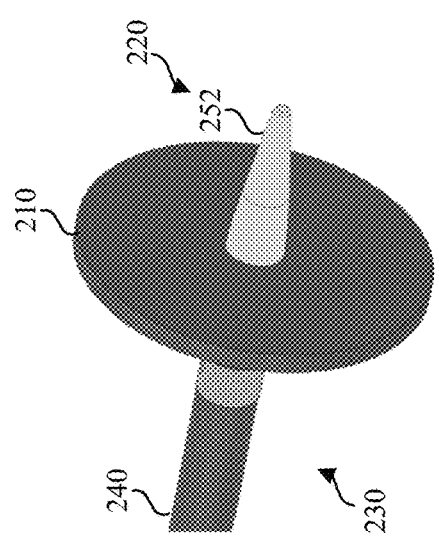
FIG. 2B
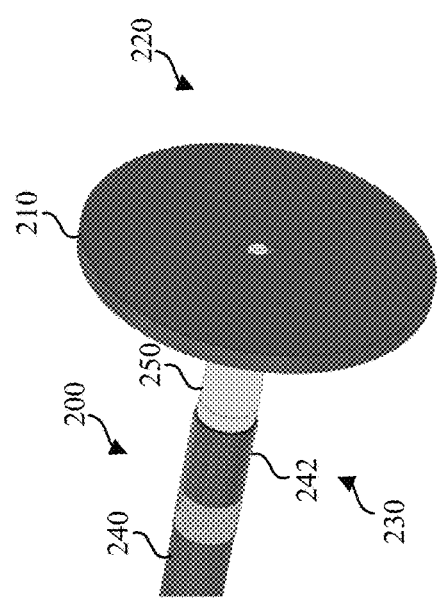
FIG. 2C
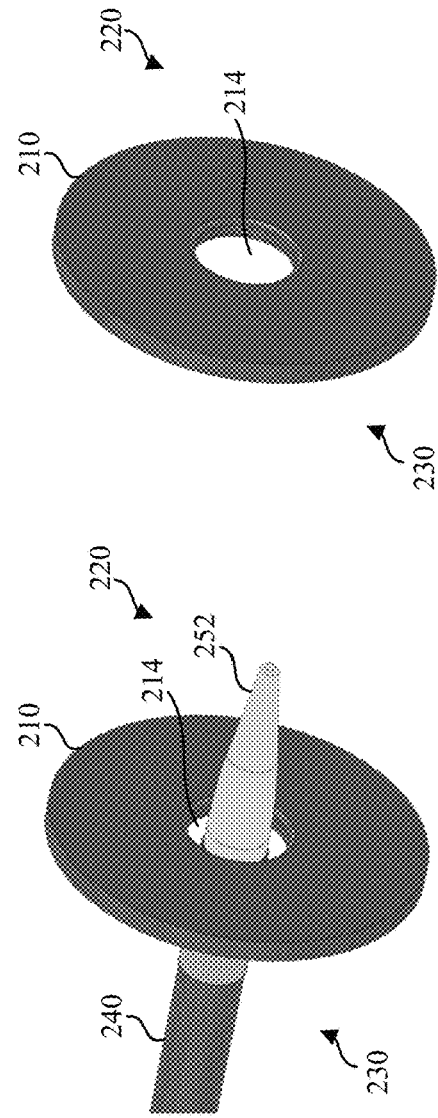
FIG. 2D
FIG. 2E
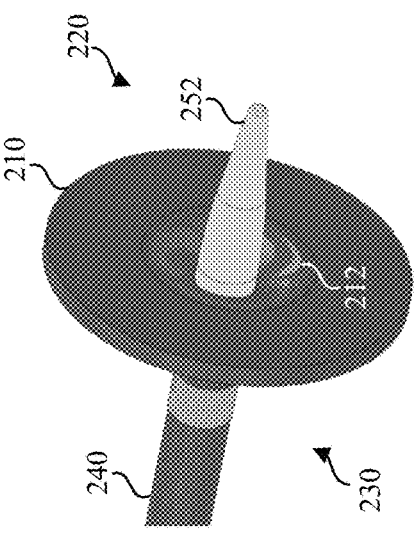
FIG. 2F

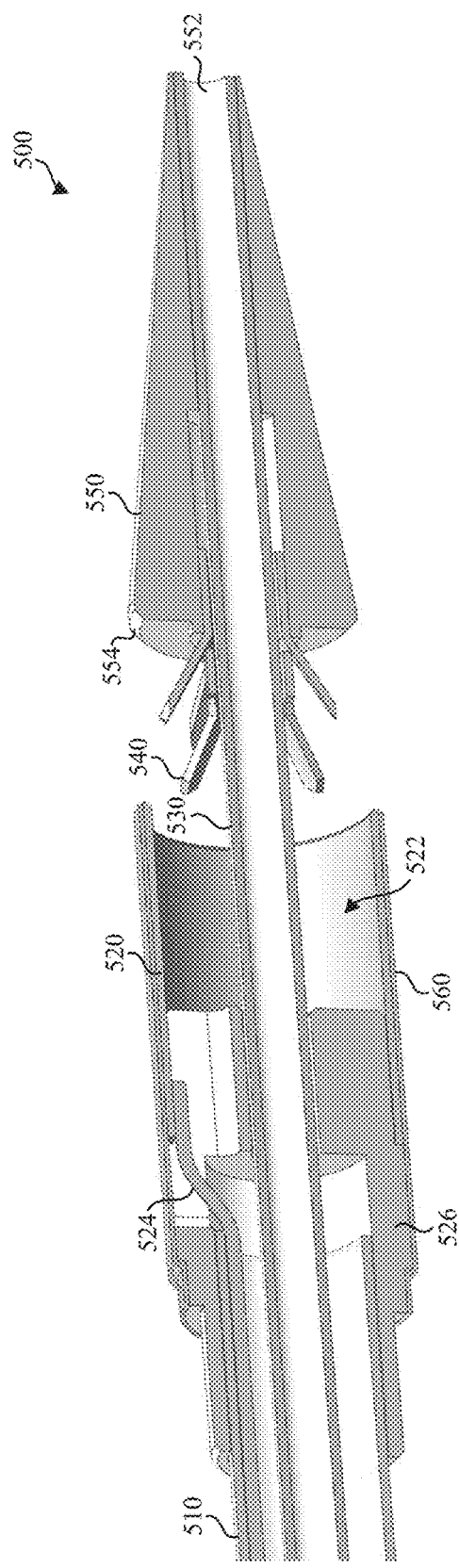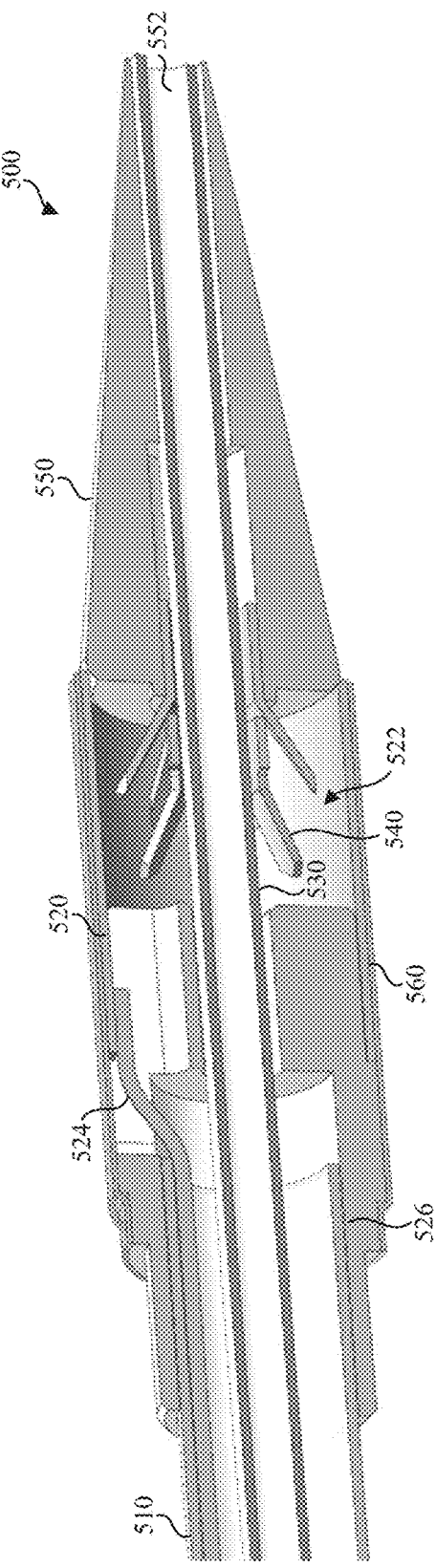
FIG. 5A
FIG. 5B

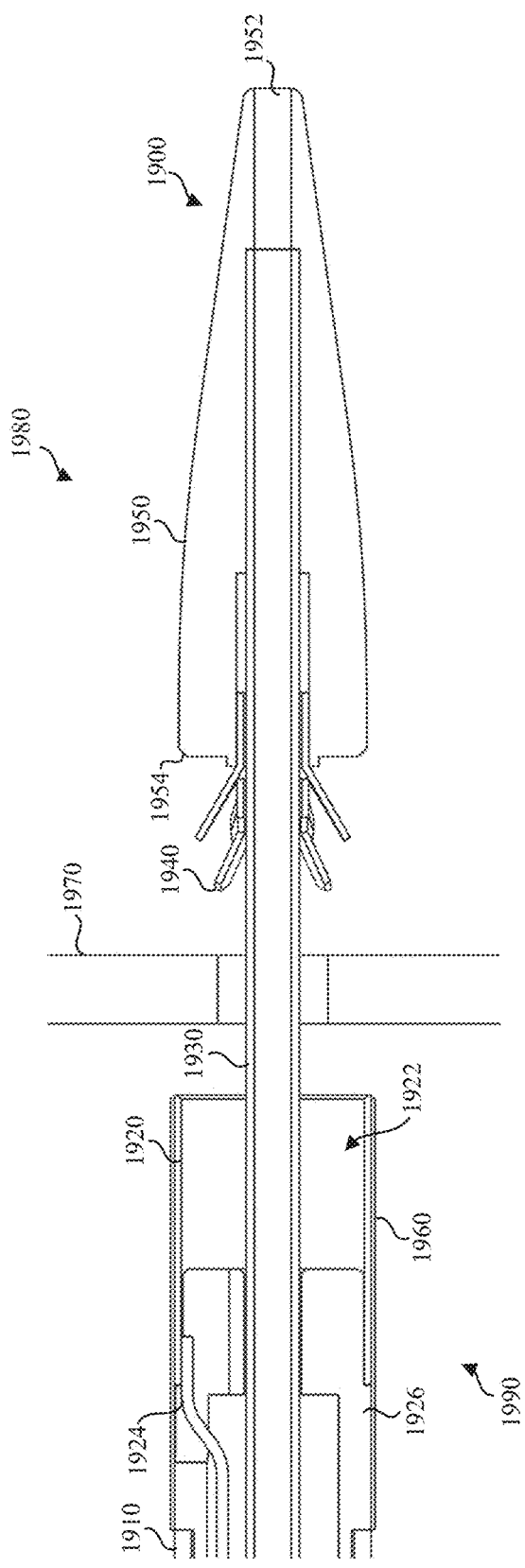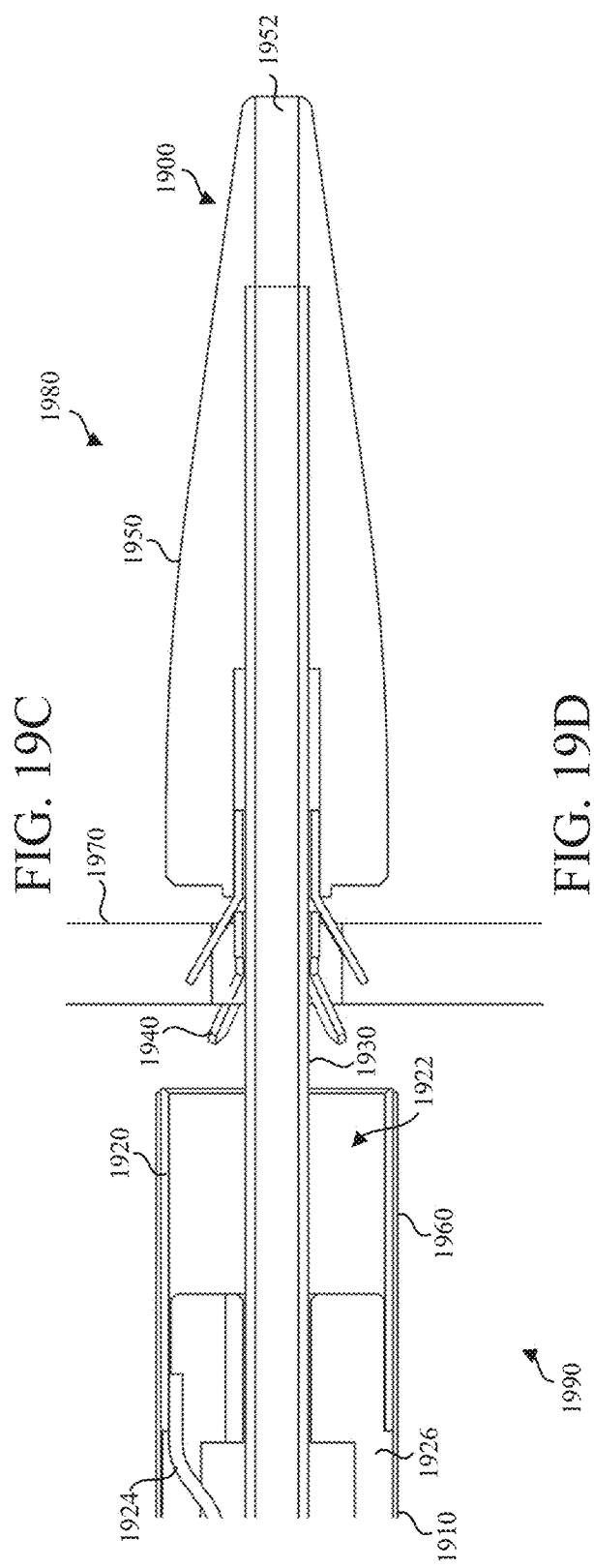

SYSTEMS, DEVICES, AND METHODS FOR FORMING AN ANASTOMOSIS

CROSS-REFERENCE TO RELATED APPLICATIONS

This application is a continuation of U.S. patent application Ser. No. 17/019,042, filed Sep. 11, 2020, which claims the benefit of U.S. Provisional Application No. 62/971,357, filed Feb. 7, 2020, and U.S. Provisional Application No. 62/900,034, filed Sep. 13, 2019, the content of each of which is hereby incorporated by reference in its entirety.

TECHNICAL FIELD

Devices, systems, and methods herein relate to forming an anastomosis, including but not limited to an anastomosis in a heart of a patient.

BACKGROUND

Congestive heart failure (CHF) is marked by declining function of the heart muscle, either due to a weakening of its pumping ability or a stiffening of the muscle with decreased ability to fill with blood prior to ejection. With poor flow of blood from the heart to vital organs, the renin-angiotensin-aldosterone system (RAAS) is activated, which signals the body to retain fluid, thereby increasing pressure in the heart chambers. In particular, as the left atrial pressure (LAP) rises, fluid backs up into the pulmonary circulation and may lead to pulmonary edema and severe shortness of breath. As such, additional devices, systems, and methods for treating heart failure may be desirable.

SUMMARY

Described herein are devices, systems, and methods for treating heart failure. These devices and systems may form an anastomosis in an anatomical structure. In some variations, a catheter for forming an anastomosis in a heart may comprise a first catheter comprising an electrode. A second catheter may be slidably disposed within the first catheter. The second catheter may comprise a barb and a dilator comprising a mating surface configured to engage the electrode.

In some variations, the barb may be disposed within a lumen of the electrode when the mating surface engages the electrode. In some variations, an outer diameter of the dilator may be less than an outer diameter of the electrode. In some variations, the barb may be configured to engage tissue.

In some variations, the second catheter may define a longitudinal axis. The barb may comprise at least one projection comprising a first portion and a second portion. The first portion may be angled relative to the second portion. A length of the first portion to a length of the second portion may be in a ratio between about 2:3 and about 1:5. In some variations, the second portion may comprise a length between about 0.1 mm and about 2 cm. The first portion may be angled between about 60 degrees and about 120 degrees relative to the longitudinal axis. In some variations, the first portion may be substantially perpendicular to the longitudinal axis. In some variations, the second portion may be angled up to about 30 degrees relative to the longitudinal axis. In some variations, the second portion may be substantially parallel to the longitudinal axis. In some variations, the barb may comprise between about 3 projections and about 7 projections. In some variations, at least one projection may comprise one of an "L" shape, "J" shape, and "C" shape. In some variations, at least one projection may comprise a plurality of projections configured in a set of concentric rings. In some variations, at least one projection may be configured to penetrate through tissue.

In some variations, the barb may comprise one or more projections angled between about 5 degrees and about 60 degrees relative to the longitudinal axis. In some of these variations, the one or more projections may be configured in rows along a length of the barb. In some variations, the projections may be configured to penetrate through the tissue and reduce tissue shear. In some variations, a length of the barb may be between about 0.1 mm and about 5 cm. In some variations, the electrode and the mating surface may be configured to compress tissue therebetween. In some variations, the second catheter may define a longitudinal axis, and the mating surface may be non-perpendicular and non-parallel to the longitudinal axis.

In some variations, the first catheter may comprise an insulator disposed over a portion of the electrode. In some variations, the insulator may comprise a fluoropolymer material. In some variations, a distal surface of the electrode and at least a portion of an inner diameter of the electrode may be uninsulated. In some variations, the electrode may be proximal to the dilator. In some variations, the first catheter may define a vent lumen. In some variations, a signal generator may be configured to generate a biphasic waveform, and the signal generator may be coupled to the electrode.

In some variations, the barb may define a longitudinal axis, and the barb may be configured to rotate about the longitudinal axis. In some variations, the barb may be configured to rotate up to about 360 degrees about the longitudinal axis.

In some variations, the dilator may define a recess configured to hold the barb. In some variations, the barb may be arranged inside the recess in a first configuration and at least a portion of the barb may be arranged outside the recess in a second configuration. In some variations, a length of the recess may be at least equal to a length of the barb. In some variations, the barb may be configured to translate relative to the dilator to transition between the first configuration and the second configuration.

In some variations, the dilator may comprise a fluid port configured to output a contrast agent. In some variations, a proximal portion of the dilator may comprise the fluid port. In some variations, the fluid port may be configured to receive the contrast agent from a lumen of the electrode. In some variations, the first catheter may comprise a contrast agent lumen. In some variations, the first catheter may be configured to output a contrast agent. In some variations, the contrast agent may be output into a lumen of the electrode. In some variations, the electrode may comprise a fluid port configured to output a contrast agent. In some variations, a distal end of the electrode may comprise the fluid port.

In some variations, the dilator may comprise an echogenic region. In some variations, the echogenic region may comprise one or more recesses or protrusions. In some variations, the one or more recesses or protrusions may comprise a diameter of between about 5 µm and about 100 µm. In some variations, the echogenic region may comprise a recess and protrusion density of between about 5% and about 50%. In some variations, the dilator may comprise one or more microspheres. In some variations, the one or more microspheres may comprise a gas core. In some variations, the one or more microspheres may comprise glass. In some variations, the echogenic region may be on a surface of the dilator. In some variations, the echogenic region may be below a surface of the dilator.

In some variations, a first catheter actuator may be configured to deflect a distal portion of the first catheter, the first catheter actuator electrically coupled to the electrode. In some variations, a proximal end of the first catheter actuator may be configured to couple to an actuation mechanism. In some variations, the first catheter actuator may comprise a pull wire extending along a length of the first catheter. In some variations, the distal portion of the first catheter may comprise a predetermined bend. In some variations, the predetermined bend may comprise an angle between about 30 degrees and about 70 degrees.

In some variations, the mating surface may define a recess configured to receive a distal end of the electrode. In some variations, the electrode may be configured to electrically short when the electrode engages the recess of the mating surface. In some variations, the mating surface may comprise a deformable material. In some variations, the mating surface may comprise a non-conductive portion. In some variations, the non-conductive portion may comprise one or more of a polymer, ceramic, and aluminum oxide. In some variations, the mating surface may comprise a conductive portion.

In some variations, a proximal portion of the dilator may be arranged within a lumen of the electrode when the mating surface engages the electrode. In some variations, between about 0.5 mm and about 2 mm of the proximal portion of the dilator may be disposed within the lumen of the electrode when the mating surface engages the electrode.

In some variations, a signal generator may be configured to generate a first waveform followed by a second waveform. The signal generator may be coupled to the electrode. The first waveform may comprise a first voltage and the second waveform may comprise a second voltage. The first voltage may be higher than the second voltage.

Also described here are methods. In some variations, a method of forming an anastomosis in a heart may comprise advancing a first and second catheter into a right atrium. The first catheter may comprise a tubular electrode defining a lumen and the second catheter may comprise a dilator and a barb. The second catheter may be advanced into a left atrium through an interatrial septum such that the first catheter is in the right atrium. The second catheter may be withdrawn relative to the first catheter to engage a first portion of the septum to the barb, withdraw the first portion into the lumen, and compress a second portion of the septum between the electrode and the dilator. An ablation waveform may be delivered to the electrode to cut the second portion such that the first portion is held within the lumen.

In some variations, withdrawing the second catheter towards the first catheter may comprise withdrawing the barb into the lumen. In some of these variations, a size of the first portion cut from the second portion may correspond to a distance the barb is withdrawn into the lumen. In some variations, withdrawing the second catheter towards the first catheter may stretch the first portion. In some variations, the first portion may form a substantially conical or cylindrical shape when engaged by the barb.

In some variations, the first portion of the septum may form a substantially cylindrical shape when withdrawn into the lumen. In some variations, the first portion of the septum engaged to the barb may be intact when withdrawn into the lumen. In some variations, the barb may pierce through the first portion when withdrawing the second catheter towards the first catheter. In some variations, an anastomosis comprising a diameter between about 1 mm and about 1.5 cm may be formed in response to delivering the ablation waveform. In some variations, the first portion may form a substantially conical shape when engaged by the barb. In some variations, the first portion may be engaged by the barb at least during delivery of the ablation waveform. In some variations, the first portion may be engaged by the barb after delivering the ablation waveform to the electrode.

In some variations, the second portion may be compressed with a force of at least 20 grams. In some variations, at least a portion of the barb may penetrate through the septum during engagement. In some variations, the electrode may be electrically shorted when the electrode contacts the dilator during delivery of the ablation waveform. In some variations, the ablation waveform may comprise a biphasic waveform. In some variations, a radiopaque portion of one or more of the first and second catheters may be fluoroscopically imaged during one or more steps.

In some variations, engaging the first portion of the septum to the barb may comprise rotating the barb about a longitudinal axis of the barb. In some variations, a size of the first portion cut from the second portion may correspond to a rotation angle of the barb. In some variations, rotating the barb may comprise a rotation angle of up to about 360 degrees.

In some variations, withdrawing the second catheter towards the first catheter may comprise translating the barb relative to the dilator to engage the first portion of the septum.

In some variations, withdrawing the second catheter towards the first catheter may comprise withdrawing the barb away from the dilator.

In some variations, withdrawing the second catheter towards the first catheter may comprise transitioning from a first configuration where the barb is arranged inside a recess of the dilator to a second configuration where the barb is arranged outside the recess.

In some variations, a contrast agent may be introduced into the heart via a fluid port in the dilator. In some variations, a contrast agent may be introduced into a lumen of the electrode. In some variations, ultrasound waves may be received from a distal end of the ablation device. In some variations, the distal end of the ablation device may comprise one or more microspheres comprising a diameter of between about 5 µm and about 100 µm.

In some variations, withdrawing the second catheter towards the first catheter may deform a proximal portion of the dilator. In some variations, withdrawing the second catheter towards the first catheter may comprise engaging the electrode to a mating surface of the second catheter. In some variations, compressing the second portion of the septum may comprise a distal end of the electrode and a mating surface of the dilator. In some variations, the second portion may be compressed with a force of up to about 25 N.

In some variations, an ablation waveform may comprise a first waveform followed by a second waveform. The first waveform may comprise a first voltage and the second waveform may comprise a second voltage. The first voltage may be higher than the second voltage.

In some variations, a proximal portion of the dilator may comprise a first step portion comprising a first diameter and a second step portion comprising a second diameter greater than the first diameter. The first step portion may be proximal to the second step portion. In some variations, the second step may comprise the mating surface configured to engage a distal end of the electrode. In some variations, the mating surface may be substantially perpendicular to a longitudinal axis of the dilator. In some variations, the first step may be configured to engage a sidewall of the electrode when the dilator engages the electrode. In some variations, the dilator may be configured to attach to the first catheter when the dilator engages the electrode.

In some variations, a system for forming an anastomosis in a heart may comprise a first catheter comprising an electrode, and a second catheter slidably disposed within the first catheter. The second catheter may comprise a barb and a dilator. A proximal portion of the dilator may comprise a first step portion comprising a first diameter and a second step portion comprising a second diameter greater than the first diameter. The first step portion may be proximal to the second step portion.

In some variations, a system for forming an anastomosis in a heart may comprise a first catheter comprising an electrode, and a second catheter slidably disposed within the first catheter. The second catheter may comprise a barb and a dilator. The barb may be enclosed within a lumen of the electrode when the dilator engages the electrode.

In some variations, a system for forming an anastomosis in a heart may comprise a first catheter comprising an electrode, and a second catheter slidably disposed within the first catheter. The second catheter may comprise a barb and a dilator. The system may be configured to compress tissue between the electrode and the dilator with a first predetermined force.

In some variations, the dilator may be configured to shear the tissue with a second predetermined force greater than the first predetermined force. In some variations, the first predetermined force may be up to about 25 N. In some variations, the second predetermined force may be more than about 25 N.

BRIEF DESCRIPTION OF THE DRAWINGS

FIGS. 2A-2F are schematic perspective views of an illustrative variation of a method of forming an anastomosis using an ablation system.

FIG. 5A is a schematic cross-sectional side view of an illustrative variation of an ablation device in an open configuration. FIG. 5B is a schematic cross-sectional side view of an illustrative variation of an ablation device in a closed configuration.

FIGS. 19C-19F are schematic cross-sectional side views of illustrative variations of an ablation device in an endocardial space.

DETAILED DESCRIPTION

Described here are devices, systems, and methods for treating heart failure (e.g., congestive heart failure) by reducing blood pressure in a left atrium of a patient. For example, an anastomosis between a right atrium and a left atrium may be formed to relieve elevated left atrial blood pressure using an energy-based tissue ablation system. Generally, the systems described here may, for example, dispose portions of a device on opposite sides of an interatrial septum. A portion of the septum may be engaged to the device using a barb. In some variations, a portion of the barb may penetrate through the septum such that the barb may securely hold an intact portion of the septum tissue. The engaged tissue may be stretched, secured, and withdrawn into a lumen of the device. In some variations, a size (e.g., diameter) of the tissue to be cut may be controlled by varying a distance that the engaged tissue is withdrawn into the lumen. Another portion of the septum may be compressed between an electrode and a proximal end of a dilator to secure additional portions of the septum to the device. The electrode may use radiofrequency (RF) energy to ablate tissue to form an anastomosis in the interatrial septum. After ablation, the electrode may contact the dilator such that the portion of tissue engaged, held, and/or secured by the barb remains enclosed within the lumen of the device for removal from the patient. One or more steps of a treatment procedure may be visualized using one or more visualization techniques and visualization features incorporated within the ablation device. Accordingly, the first and second catheters as described herein may improve the efficacy and safety of an anastomosis formation procedure, as well as allow a size of the catheter to be reduced.

Figure 1:
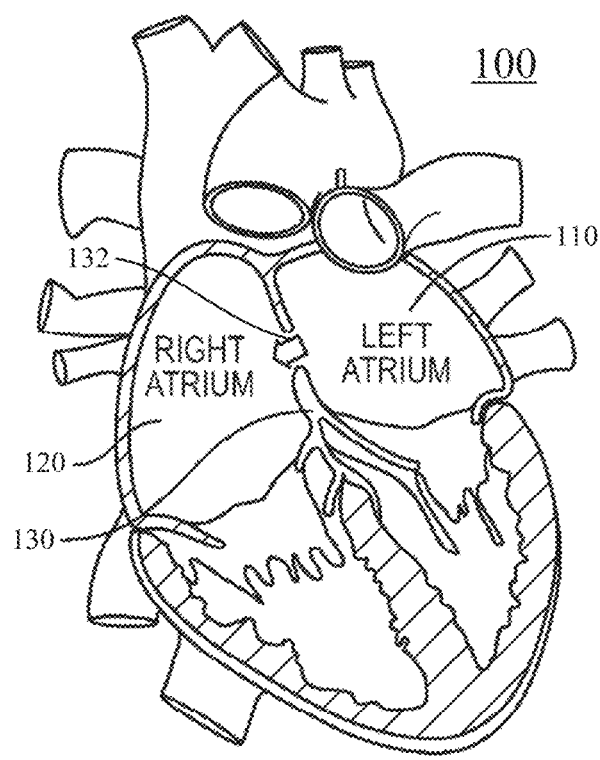
FIG. 1 provides a cross-sectional representation of a heart showing various anatomical structures.

In instances where the heart is the relevant anatomy, it may be helpful to briefly identify and describe the relevant heart anatomy. FIG. 1 is a cross-sectional view of the heart (100). Shown there is the left atrium (110), right atrium (120), and interatrial septum (130). FIG. 1 illustrates an opening (132) (e.g., aperture) formed between the left atrium (110) and the right atrium (120). For example, the opening (132) may be created during an anastomosis procedure using the systems, devices, and methods described herein. The opening (132) may have predetermined characteristics configured to treat heart failure.

Also described here are methods. In some variations, a method of forming an anastomosis in an interatrial septum may include the step shown in FIG. 2A including advancing an ablation device (200) into a right atrium (230) of a patient. A distal end of the device (200) may comprise a dilator of a second catheter (250) configured to puncture an interatrial septum (210) and advance into a left atrium (220) of the patient. In some variations, a guidewire (not shown) of the device (200) may be advanced across the interatrial septum (210) and into the left atrium (220). As shown in FIG. 2B, the dilator may puncture the septum (210) such that portions of the second catheter (250) are disposed within the left atrium (220) and the first catheter (240) is disposed within the right atrium (230).

FIG. 2C illustrates the second catheter (250) advanced relative to the first catheter (240) such that a barb (260) of the second catheter (250) is advanced across the septum (210) and into the left atrium (220). The barb (260) may be configured to engage a portion of the septum (210) for ablation. For example, a portion of the engaged septum may be held and/or secured between the projections of the barb (260). By positioning the device (200) across both sides of the interatrial septum (210), a predetermined force may be applied from respective catheters (240, 250) to engage and cut a predetermined portion of septum tissue.

As shown in FIG. 2D, the second catheter (250) may be withdrawn relative to the first catheter (240) such that a portion (212) of the septum (210) may engage the barb (260) and stretch. Each of the electrode (242) (FIG. 2A) and the barb (260) may be positioned to engage opposite sides of the septum tissue (212). For example, withdrawal of the barb (260) into a lumen of the electrode (242) may engage and stretch the tissue (212) so as to form a tent-like shape that may aid formation of an anastomosis. Tissue (212) in FIG. 2D is shown tented towards the right atrium (230). In this manner, tissue (212) to be cut is secured within the device (200) prior to excision to reduce the risk of uncontrolled tissue loss in the heart chambers and vasculature.

In some of these variations, the electrode (242) may comprise a tubular shape configured to cut tissue using RF energy and promote tissue capture. In some variations, a mating surface of the dilator (252) may be configured to engage, hold, and secure cut tissue against a cutting surface of the electrode (242). An ablation waveform may be delivered to the electrode (242) to cut the portion (212) of the interatrial septum (210) stretched by the device (200). For example, the ablation waveform may comprise RF energy as described in more detail herein. The second catheter (250) may be positioned against the first catheter (240) as the electrode (242) is energized such that the barb (260) is held in a lumen of the electrode (242).

Once the septum (210) is cut, as shown in FIG. 2E, a hole (214) may be formed in the septum (210). The second catheter (250) may be withdrawn from the left atrium (220) and the device (210) may be removed from the patient as shown in FIG. 2F. Accordingly, an ablation device (200) may form an interatrial anastomosis. The ablation devices as described herein may improve the efficacy and safety of an anastomosis procedure, as well as allow a reduction in a size of the device. For example, after crossing the interatrial septum (210), the operator may capture and secure tissue by advancing and retracting the second catheter (250) relative to the first catheter (240) without additional actuation mechanisms. This and other benefits of the devices and methods are described in more detail below herein.

I. System

Overview

Figure 3:
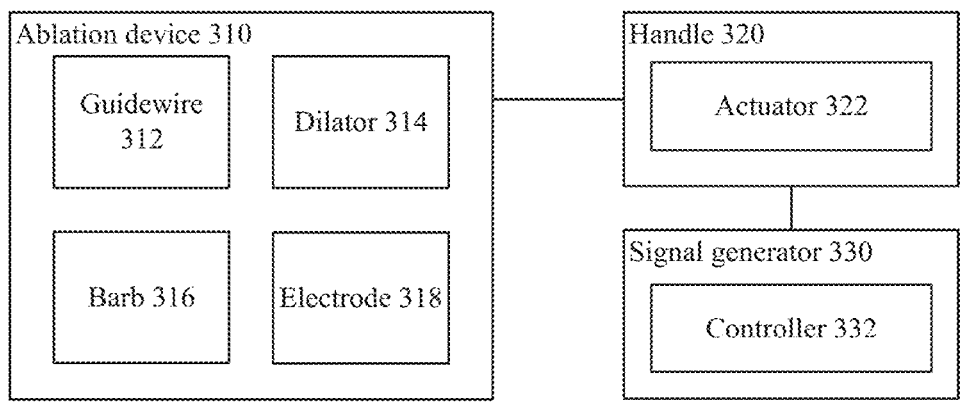
FIG. 3 is a schematic block diagram of an illustrative variation of an ablation system.

Systems described here may include one or more of the components used to ablate tissue using the devices as described herein. FIG. 3 is a block diagram of a variation of an ablation system (300) comprising an ablation device (310), handle (320), and signal generator (330). In some variations, the ablation device (310) may be designed to be disposable after each use, while in other variations, one or more portions of the ablation device (310) may be designed to be reusable (e.g., used multiple times, and with one or more patients) such as the handle (320) and signal generator (330).

In some variations, the ablation device (310) may comprise first and second catheters sized and shaped to be placed in a body cavity of the patient such as a heart chamber. In some variations, the ablation device (310) may comprise one or more of a guidewire (312), dilator (314), barb (316), and electrode (318). A distal end of the ablation device (310) may comprise the dilator (314) and the guidewire (312) may extend from a lumen of the dilator (314). In some variations, the electrode (318) may be disposed proximal to the barb (316), while in other variations, the electrode (318) may be disposed distal to the barb (316). Additionally or alternatively, the ablation system (300) may comprise a delivery catheter configured to advance over the ablation device (310). Furthermore, the ablation device (310) may comprise one or more sensors configured to measure one or more predetermined characteristics such as temperature, pressure, impedance, and the like.

In some variations, a proximal end of the ablation device (310) may be coupled to a handle (320). The handle (320) may comprise an actuator (322) configured to control one or more of movement, positioning, configuration, orientation, operation, and energy delivery of the ablation device (310). For example, the actuator (322) may be operated to steer and/or translate one or more portions of the ablation device (310). In some variations, a signal generator (330) may be coupled to one or more of the ablation device (310) and handle (320). The signal generator (330) may be configured to generate one or more ablation waveforms for delivery to the electrode (318) of the ablation device (310). The signal generator (330) may comprise a controller (332) configured to control the signal generator (330) and provide appropriate energy waveforms for tissue ablation and ensure patient safety.

Figure 4:
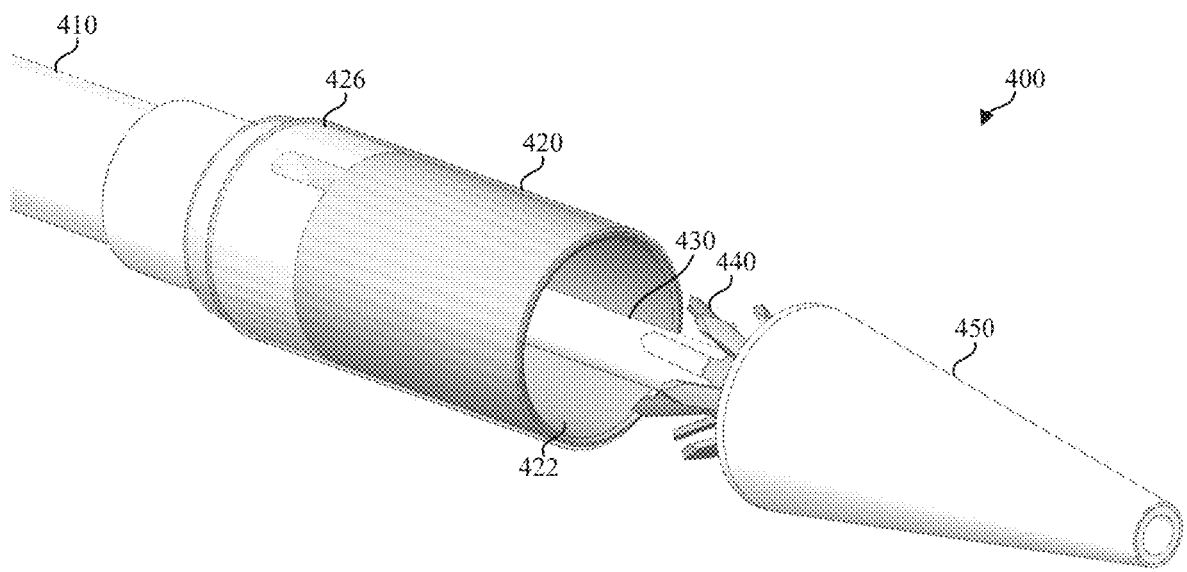
FIG. 4 is a perspective view of an illustrative variation of an ablation device.

FIG. 4 is a perspective view of a variation of an ablation device (400). In some variations, the ablation device (400) may comprise a first catheter (410) and a second catheter (430). The first catheter (410) may comprise a tubular electrode (420). The electrode (420) may define a lumen (422) configured to hold one or more portions of the second catheter (430). The electrode (420) shown in FIG. 4 has a cylindrical shape. However, the electrode (420) may comprise any desired cross-sectional shape (e.g., oval, square, rectangular, triangular). The electrode (420) shown in FIG. 4 may comprise a distal cutting edge. However, the electrode (420) may have a beveled or non-planar edge (e.g., wavy, crenelated, saw-tooth, sinusoidal, periodic, etc.).

In some variations, the ablation device (400) may comprise a second catheter (430) slidably disposed within the first catheter (410). The second catheter (430) may comprise a barb (440) and a dilator (450) configured to engage the electrode (420). In some variations, the barb (440) may be coupled to a proximal portion of the dilator (450). A tissue engagement portion (e.g., projection, point) of the barb (440) may generally face the electrode (420). The barb (440) may comprise a plurality of projections. In some variations, one or more of the projections may be bent to form a curvilinear shape. In some variations, a proximal portion of the dilator (450) may be configured to contact the electrode (420) when the second catheter (430) is withdrawn relative to the first catheter (410). The dilator (450) may have, for example, a generally conical shape that tapers toward a distal end of the second catheter (430). However, the dilator (450) may comprise any predetermined size, pattern, and shape. For example, at least a portion of the dilator (450) may be configured to recess into the lumen (422) of the electrode (420) to secure the dilator (450) to the catheter (410) during catheter delivery and removal and further secures excised tissue during withdrawal from the patient.

As described in more detail herein, the second catheter (430) may be configured to translate relative to the first catheter (410). For example, the second catheter (430) may translate along a longitudinal axis of the first catheter (410). In some variations, one or more of the second catheter (430), barb (440), and dilator (450) may translate into the lumen (422) of the electrode (420). As described in more detail herein, the electrode (420) may be configured to ablate tissue compressed between a distal end (e.g., distal cutting edge, chamfer) of the electrode (420) and the dilator (450).

FIG. 5A is a schematic cross-sectional side view of a variation of an ablation device (500) in an open configuration. In some variations, the ablation device (500) may comprise a first catheter (510) and a second catheter (530). The first catheter (510) may comprise a tubular electrode (520) and a connector (526) coupled to the electrode (520). The electrode (520) may define a lumen (522) configured to hold one or more portions of the second catheter (530). The first catheter (510) may further comprise a lead (524) coupled to the electrode (520) and a signal generator (not shown). In some variations, the first catheter (510) may comprise an insulator (560) configured to cover a portion of the electrode (520). For example, the insulator (560) may be configured to cover an outer surface of the electrode (520) where a distal end and inner surface of the electrode (520) are uninsulated.

In some variations, the ablation device (500) may comprise a second catheter (530) slidably disposed within the first catheter (510). The second catheter (530) may comprise a barb (540) and a dilator (550) configured to engage the electrode (520). In some variations, the barb (540) may comprise a plurality of projections arranged in rows that are angled generally towards the electrode (520). For example, the projections may be configured in rows along a length of the dilator (550). Additionally or alternatively, one or more of the projections may be bent to form a curvilinear shape. The dilator (550) may be tapered and define a lumen (552). The electrode (520) may be proximal to the dilator (550). In some variations, the dilator (550) may comprise a mating surface (554) configured to engage the electrode (520). For example, the electrode (520) and mating surface (554) may be configured to compress tissue therebetween (not shown). In some variations, the mating surface (554) may be non-perpendicular and non-parallel to a longitudinal axis of the second catheter (530) (e.g., chamfered, beveled). As shown in FIGS. 5A and 5B, the distal end of the electrode (520) and the mating surface (554) may be radial.

FIG. 5B is a schematic cross-sectional side view of a variation of the ablation device (500) in a closed configuration. The barb (540) may be enclosed by the electrode (520), connector (526), and dilator (550) in the closed configuration. That is, the barb (540) may be disposed within a lumen (522) of the electrode (520) when the mating surface (554) engages the electrode (520). Accordingly, any tissue engaged by the barb (540) may also be enclosed and secured within the ablation device (500) in the closed configuration by one or more of the barb (540) and electrode (520). In some variations, an outer diameter of the dilator (550) may be less than an outer diameter of a distal end of the first catheter (510). For example, the outer diameter of the dilator (550) may be less than an outer diameter of the electrode (520). This may control a shape of the tented tissue engaged by the ablation device (500). As described in more detail herein, a length and shape of the barb (540) may further control a size and shape of the tented tissue.

Figure 6A:
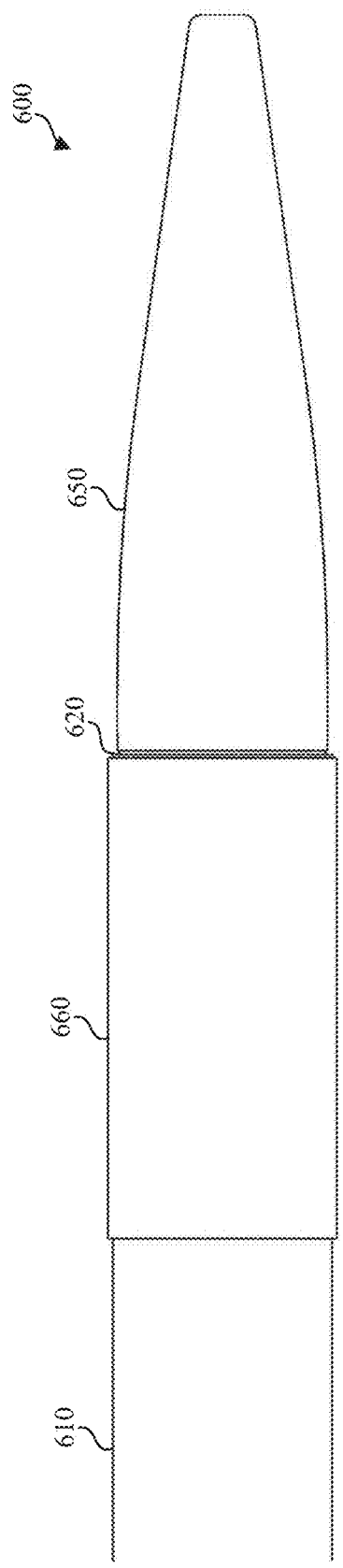
FIG. 6A is a schematic side view of an illustrative variation of an ablation device in a closed configuration.
Figure 6B:
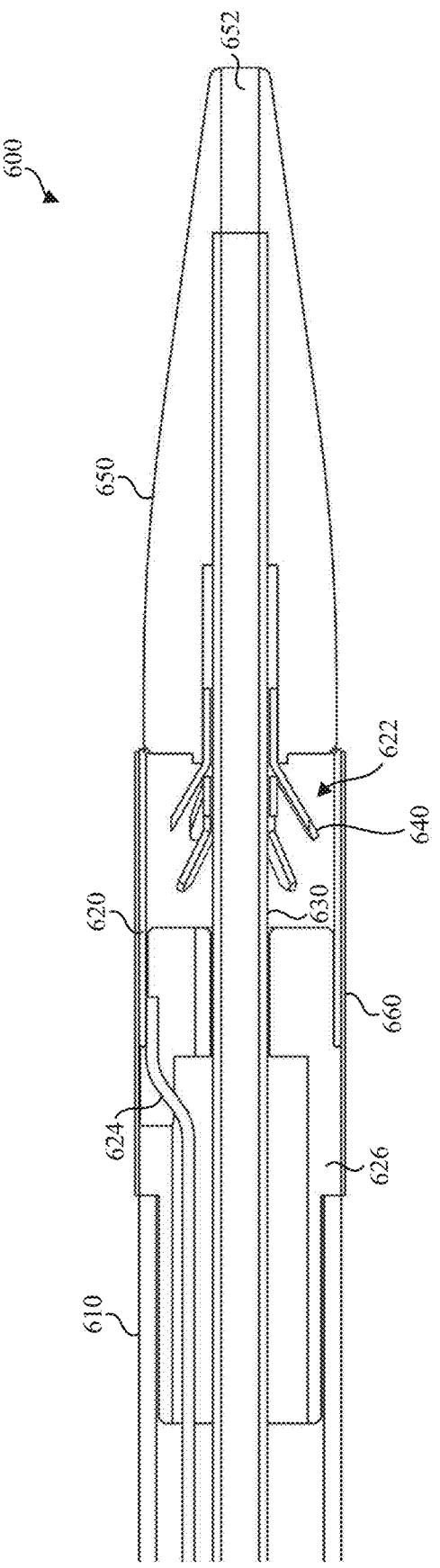
FIG. 6B is a schematic cross-sectional side view of the ablation device shown in FIG. 6A.

FIG. 6A is a schematic side view of a variation of an ablation device (600) in a closed configuration. FIG. 6A shows the ablation device (600) comprising a first catheter (610), electrode (620), dilator (650), and insulator (660). FIG. 6B is a schematic cross-sectional side view of the ablation device (600). In some variations, the ablation device (600) may comprise a first catheter (610) and a second catheter (630). The first catheter (610) may comprise a tubular electrode (620) and a connector (626) coupled to the electrode (620). The electrode (620) may define a lumen (622) configured to hold one or more portions of the second catheter (630). The first catheter (610) may further comprise a lead (624) coupled to the electrode (620) and a signal generator (not shown). In some variations, the first catheter (610) may comprise an insulator (660) configured to cover a portion of the electrode (620). For example, the insulator (660) may be configured to cover an outer surface of the electrode (620) where a distal end and inner surface of the electrode (620) are uninsulated.

In some variations, the ablation device (600) may comprise a second catheter (630) slidably disposed within the first catheter (610). The second catheter (630) may comprise a barb (640) and a dilator (650) configured to engage the electrode (620). In some variations, the barb (640) may comprise a plurality of projections arranged in rows that are angled generally towards the electrode (620). For example, the projections may be configured in rows along a length of the dilator (650). Additionally or alternatively, one or more of the projections may be bent to form a curvilinear shape. The dilator (650) may be tapered and define a lumen (652). The electrode (620) may be proximal to the dilator (650). Additionally or alternatively, one or more of the projections may be bent to form a curvilinear shape.

In the closed configuration, the barb (640) may be enclosed by the electrode (620), connector (626), and dilator (650). That is, the barb (640) may be disposed within a lumen (622) of the electrode (620) when the mating surface (654) engages the electrode (620). Accordingly, any tissue engaged by the barb (640) may also be enclosed, held, and/or secured within the ablation device (600) in the closed configuration.

Figure 6C:
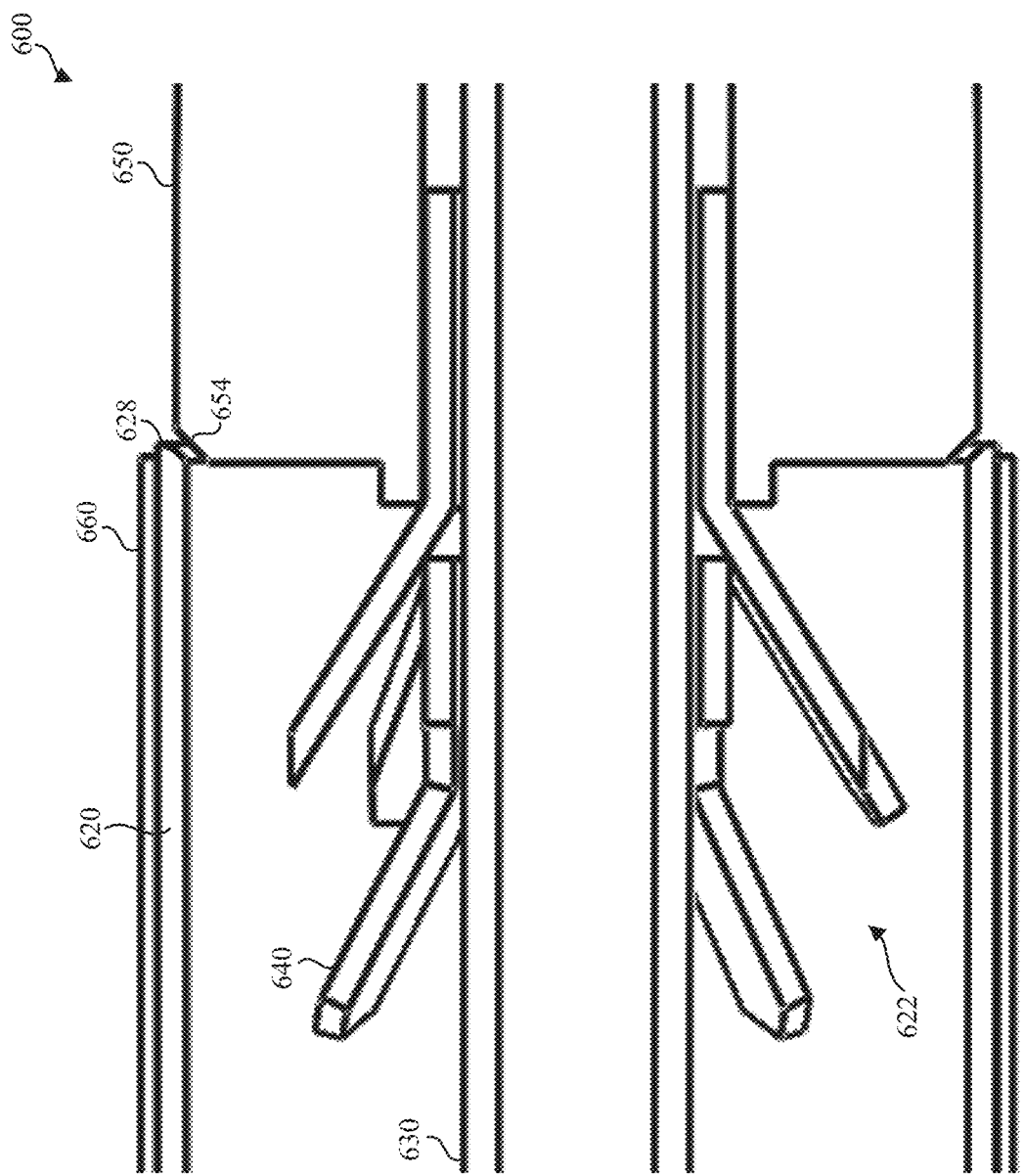
FIG. 6C is a detailed cross-sectional side view of the ablation device shown in FIG. 6B.

FIG. 6C is a detailed cross-sectional side view of the ablation device (600) shown in FIG. 6B. In particular, the dilator (650) may comprise a mating surface (654) configured to engage the electrode (620). For example, the electrode (620) and mating surface (654) may be configured to compress tissue therebetween (not shown). In some variations, the mating surface (654) may be non-perpendicular and non-parallel to a longitudinal axis of the second catheter (630) (e.g., chamfered, beveled). The distal end of the electrode (620) and the mating surface (654) may be radial. As shown in FIGS. 6B and 6C, an outer diameter of the dilator (650) may be less than an outer diameter of the electrode (620).

Figure 7A:
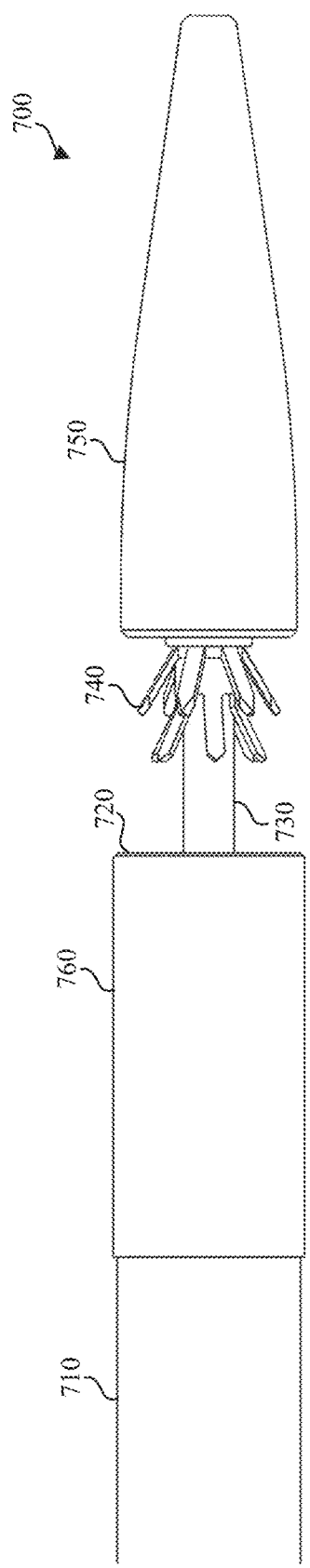
FIG. 7A is a schematic side view of an illustrative variation of an ablation device in an open configuration.
Figure 7B:
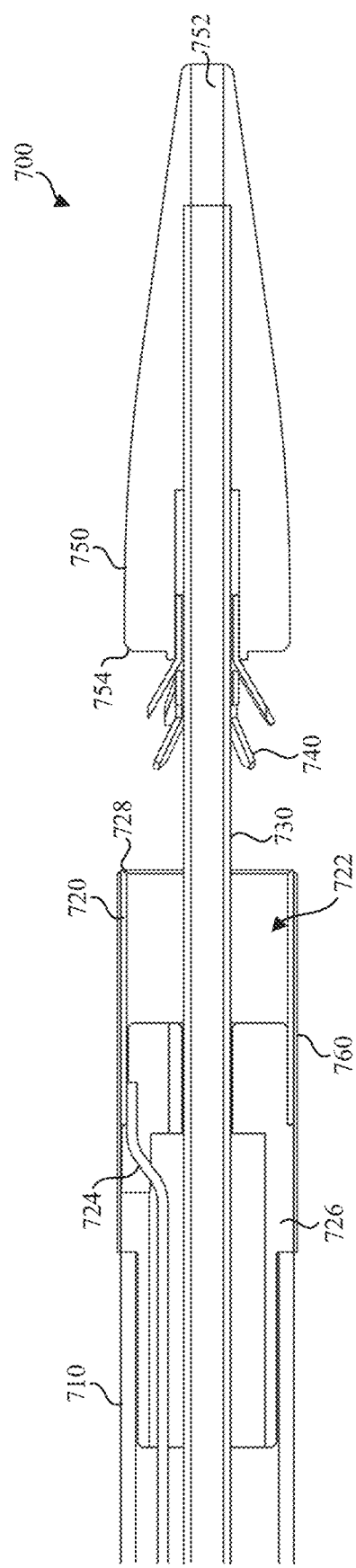
FIG. 7B is a schematic cross-sectional side view of the ablation device shown in FIG. 7A.

FIG. 7A is a schematic side view of a variation of an ablation device (700) in an open configuration. FIG. 7A shows the ablation device (700) comprising a first catheter (710), electrode (720), second catheter (730), barb (740), dilator (750), and insulator (760). FIG. 7B is a schematic cross-sectional side view of the ablation device (700) shown in FIG. 7A. In some variations, the ablation device (700) may comprise a first catheter (710) and a second catheter (730). The first catheter (710) may comprise a tubular electrode (720) and a connector (726) coupled to the electrode (720). The electrode (720) may define a lumen (722) configured to hold one or more portions of the second catheter (730). The first catheter (710) may further comprise a lead (724) coupled to the electrode (720) and a signal generator (not shown). In some variations, the first catheter (710) may comprise an insulator (760) configured to cover a portion of the electrode (720). For example, the insulator (760) may be configured to cover an outer surface of the electrode (720) where a distal end and inner surface of the electrode (720) are uninsulated.

In some variations, the ablation device (700) may comprise a second catheter (730) slidably disposed within the first catheter (710). The second catheter (730) may comprise a barb (740) and a dilator (750) configured to engage the electrode (720). In some variations, the barb (740) may comprise a plurality of projections arranged in rows that are angled generally towards the electrode (720). For example, the projections may be configured in rows along a length of the dilator (750). Additionally or alternatively, one or more of the projections may be bent to form a curvilinear shape. The dilator (750) may be tapered and define a lumen (752). The electrode (720) may be proximal to the dilator (750).

Figure 7C:
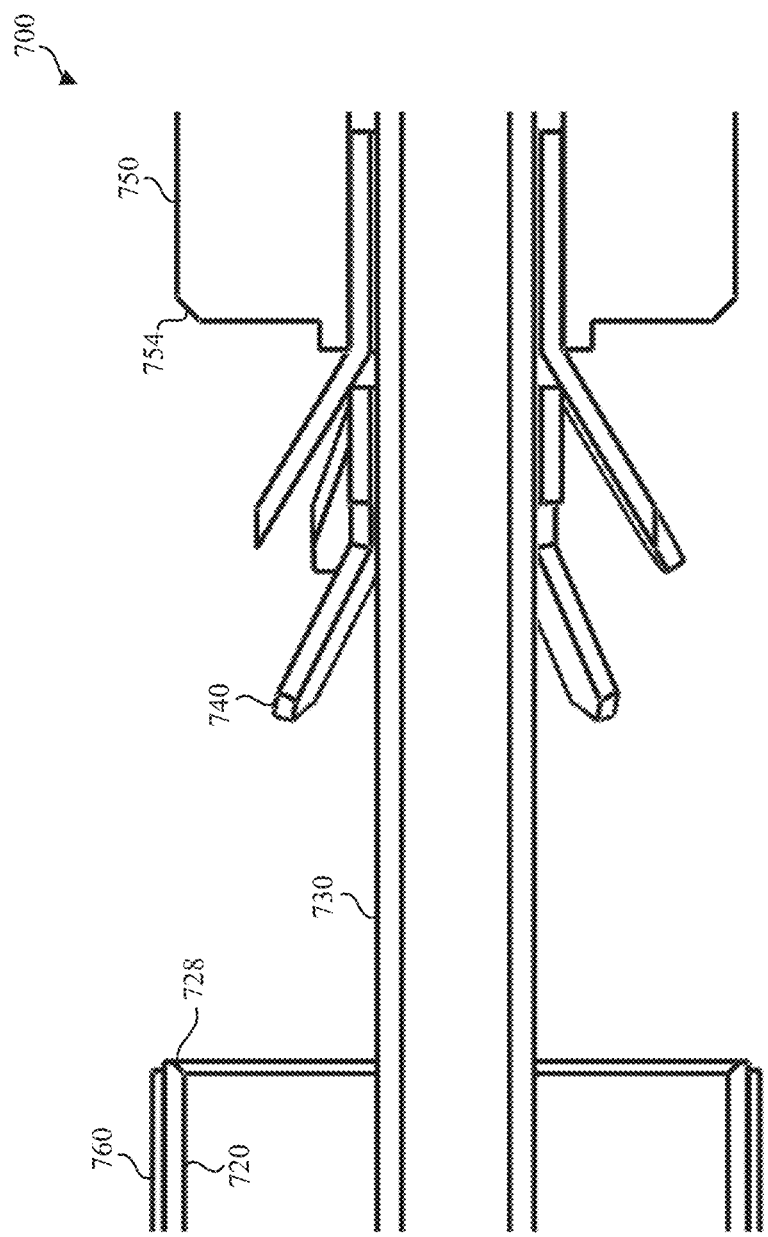
FIG. 7C is a detailed cross-sectional side view of the ablation device shown in FIG. 7B.

FIG. 7C is a detailed cross-sectional side view of the ablation device (700) shown in FIG. 7B. In particular, the dilator (750) may comprise a mating surface (754) configured to engage the electrode (720). For example, the electrode (720) and mating surface (754) may be configured to compress tissue therebetween (not shown). In some variations, the mating surface (754) may be non-perpendicular and non-parallel to a longitudinal axis of the second catheter (730) (e.g., chamfered, beveled). The distal end of the electrode (720) and the mating surface (754) may be radial.

Figure 8:
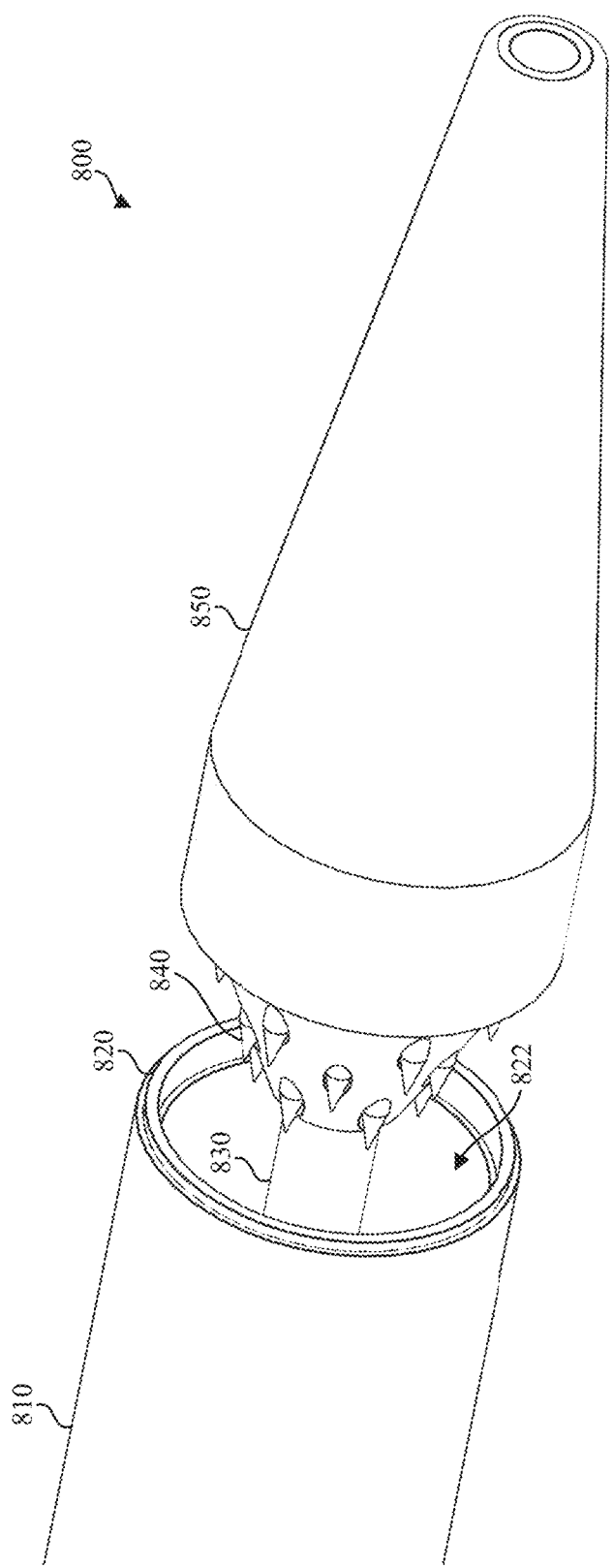
FIG. 8 is a schematic perspective view of an illustrative variation of an ablation device.

FIGS. 8-10B illustrate additional ablation device variations. FIG. 8 is a perspective view of a variation of an ablation device (800). In some variations, the ablation device (800) may comprise a first catheter (810) and a second catheter (830). The first catheter (810) may comprise a tubular electrode (820). The electrode (820) may define a lumen (822) configured to hold one or more portions of the second catheter (830). The electrode (820) shown in FIG. 8 has a cylindrical shape. However, the electrode (820) may comprise any desired cross-sectional shape (e.g., oval, square, rectangular, triangular).

In some variations, the ablation device (800) may comprise a second catheter (830) slidably disposed within the first catheter (810). The second catheter (830) may comprise a barb (840) and a dilator (850) configured to engage the electrode (820). In some variations, the barb (840) may be coupled to a proximal portion of the dilator (850). The barb (840) may comprise a tapered portion and a plurality of projections disposed radially about the barb (840) and arranged in staggered rows along a length of the second catheter (830). Tissue engaged by one or more of the projections may form a generally conical shape that generally follows the tapered shape of the barb (840). The plurality of projections may have the same or different length, diameter, and taper. Each row may have the same or different number of projections. The plurality of projections may have the same or different angle relative to the second catheter (830).

In some variations, the plurality of projections (e.g., tissue engagement portions) of the barb (840) may be generally parallel to a longitudinal axis of the second catheter (830). In some variations, a proximal portion of the dilator (850) may be configured to contact the electrode (820) when the second catheter (830) is withdrawn relative to the first catheter (810). The dilator (850) may have, for example, a generally conical shape that tapers toward a distal end of the second catheter (830). However, the dilator (850) may comprise any predetermined size, pattern, and shape.

As described in more detail herein, the second catheter (830) may be configured to translate relative to the first catheter (810). For example, the second catheter (830) may translate along a longitudinal axis of the first catheter (810). In some variations, one or more of the second catheter (830), barb (840), and dilator (850) may translate into the lumen (822) of the electrode (820). As described in more detail herein, the electrode (820) may be configured to ablate tissue compressed between a distal end of the electrode (820) and the dilator (850).

Figure 9A:
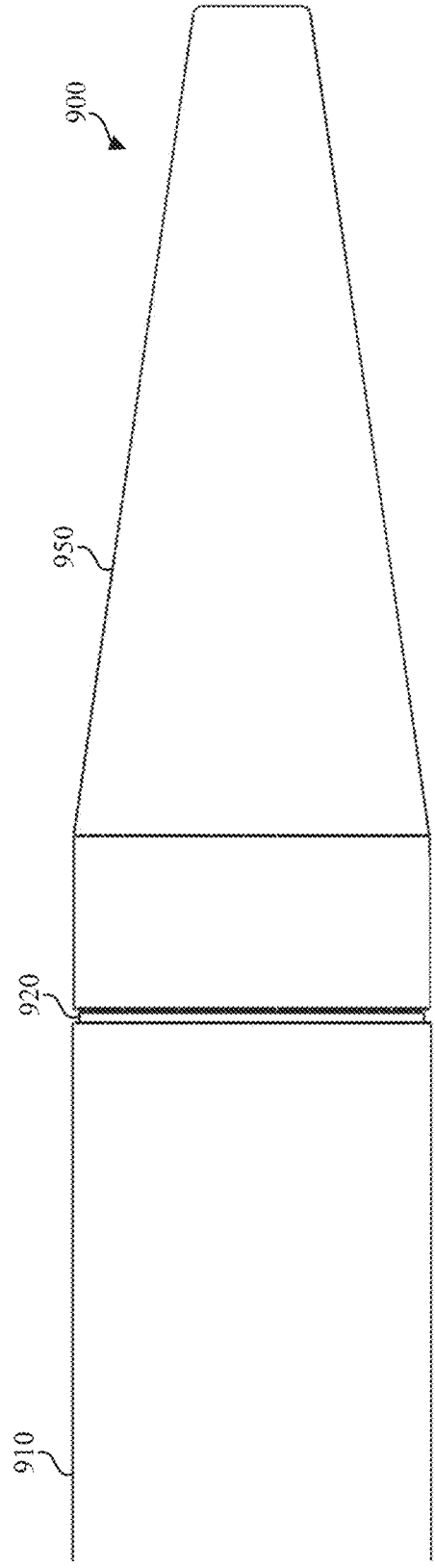
FIG. 9A is a schematic side view of an illustrative variation of an ablation device in a closed configuration.
Figure 9B:
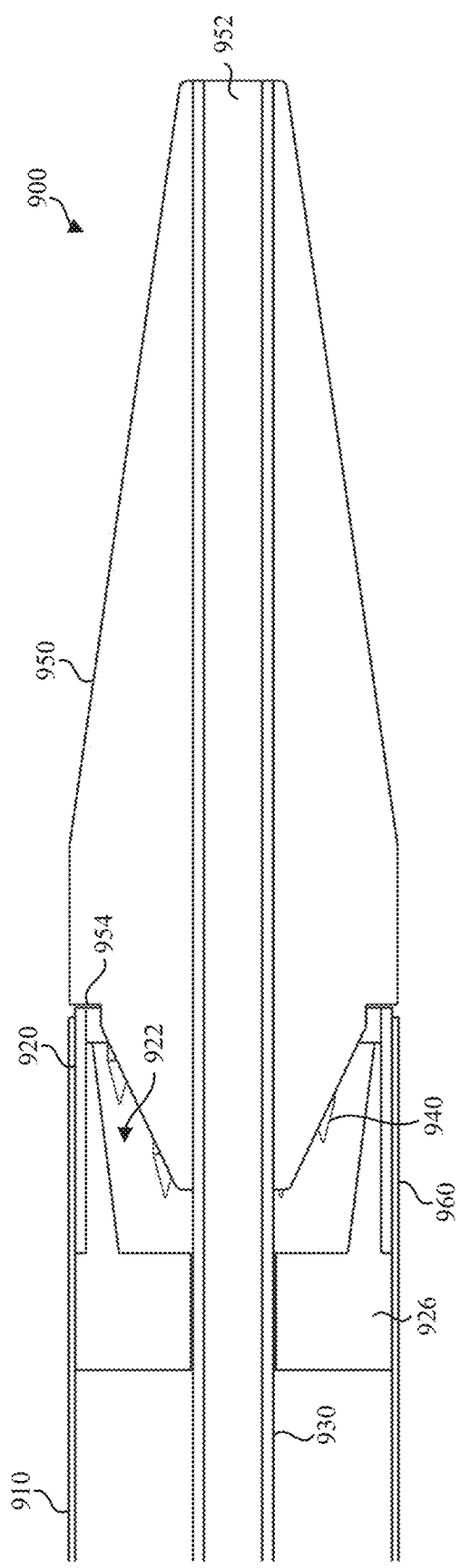
FIG. 9B is a schematic cross-sectional side view of an illustrative variation of an ablation device in a closed configuration.

FIG. 9A is a schematic side view of a variation of an ablation device (900) in a closed configuration. FIG. 9A shows the ablation device (900) comprising a first catheter (910), electrode (920), and dilator (950). FIG. 9B is a schematic cross-sectional side view of the ablation device (900). In some variations, the ablation device (900) may comprise a first catheter (910) and a second catheter (930). The first catheter (910) may comprise a tubular electrode (920) and a connector (926) coupled to the electrode (920). The electrode (920) may define a lumen (922) configured to hold one or more portions of the second catheter (930) (e.g., barb (940)). The first catheter (910) may further comprise a lead (not shown) coupled to the electrode (920) and a signal generator (not shown). In some variations, the first catheter (910) may comprise an insulator (960) configured to cover a portion of the electrode (920). For example, the insulator (960) may be configured to cover an outer surface of the electrode (920) such that a distal end and inner surface of the electrode (920) are uninsulated.

In some variations, the ablation device (900) may comprise a second catheter (930) slidably disposed within the first catheter (910). The second catheter (930) may comprise a barb (940) and a dilator (950) configured to engage the electrode (920). In some variations, the barb (940) may comprise a plurality of projections arranged in rows that are generally parallel to a longitudinal axis of the second catheter (930). For example, the projections may be configured in rows along a length of the second catheter (930). Additionally or alternatively, one or more of the projections may be bent to form a curvilinear shape. The dilator (950) may be tapered and define a lumen (952). In some variations, the dilator (950) may comprise a mating surface (954) configured to engage the electrode (920). For example, the electrode (920) and mating surface (954) may be configured to compress tissue therebetween (not shown). In FIG. 9B, the mating surface (954) is generally perpendicular to the longitudinal axis of the second catheter (930). The electrode (920) may be proximal to the dilator (950). The distal end of the electrode (920) and the mating surface (954) may be radial.

In the closed configuration, the barb (940) may be enclosed by the electrode (920), connector (926), and dilator (950). That is, the barb (940) may be disposed within a lumen (922) of the electrode (920) when a mating surface (954) of the dilator (950) engages the electrode (920). Accordingly, any tissue engaged by the barb (940) may also be enclosed, held, and/or secured within the ablation device (900) in the closed configuration.

Figure 10A:
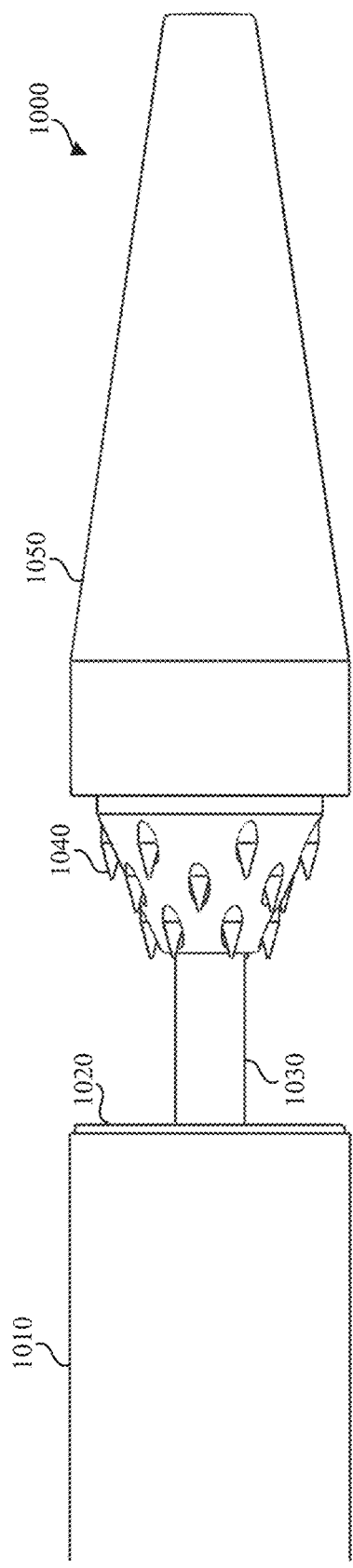
FIG. 10A is a schematic side view of an illustrative variation of an ablation device in an open configuration.
Figure 10B:
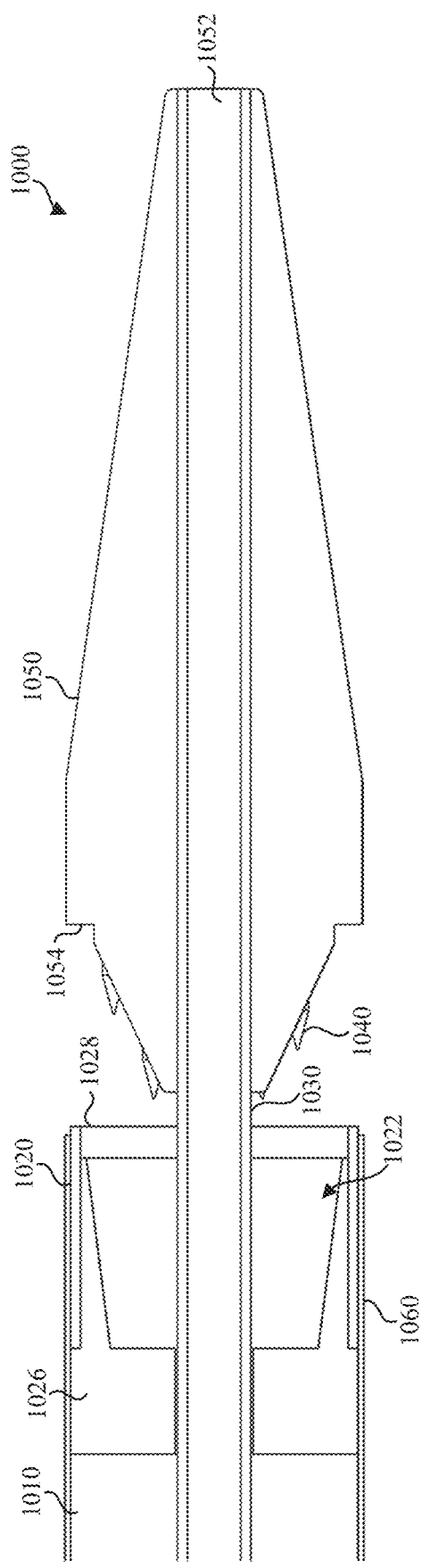
FIG. 10B is a schematic cross-sectional side view of an illustrative variation of an ablation device in an open configuration.

FIG. 10A is a schematic side view of a variation of an ablation device (1000) in an open configuration. FIG. 10A shows the ablation device (1000) comprising a first catheter (1010), electrode (1020), second catheter (1030), barb (1040), and dilator (1050). FIG. 10B is a schematic cross-sectional side view of the ablation device (1000) shown in FIG. 10A. In some variations, the ablation device (1000) may comprise a first catheter (1010) and a second catheter (1030). The first catheter (1010) may comprise a tubular electrode (1020) and a connector (1026) coupled to the electrode (1020). The electrode (1020) may define a lumen (1022) configured to hold one or more portions of the second catheter (1030). The first catheter (1010) may further comprise a lead (not shown) coupled to the electrode (1020) and a signal generator (not shown). In some variations, the first catheter (1010) may comprise an insulator (1060) configured to cover a portion of the electrode (1020). For example, the insulator (1060) may be configured to cover an outer surface of the electrode (1020) such that a distal end and inner surface of the electrode (1020) are uninsulated.

In some variations, the ablation device (1000) may comprise a second catheter (1030) slidably disposed within the first catheter (1010). In some variations, the barb (1040) may comprise a plurality of projections arranged in rows that are generally parallel to a longitudinal axis of the second catheter (1030). For example, the projections may be configured in rows along a length of the second catheter (1030). Additionally or alternatively, one or more of the projections may be bent to form a curvilinear shape. The dilator (1050) may be tapered and define a lumen (1052). In some variations, the dilator (1050) may comprise a mating surface (1054) configured to engage the electrode (1020). For example, the electrode (1020) and mating surface (1054) may be configured to compress tissue therebetween (not shown). In FIG. 10B, the mating surface (1054) is generally perpendicular to the longitudinal axis of the second catheter (1030). The electrode (1020) may be proximal to the dilator (1050). The distal end of the electrode (1020) and the mating surface (1054) may be radial.

Figure 38A:
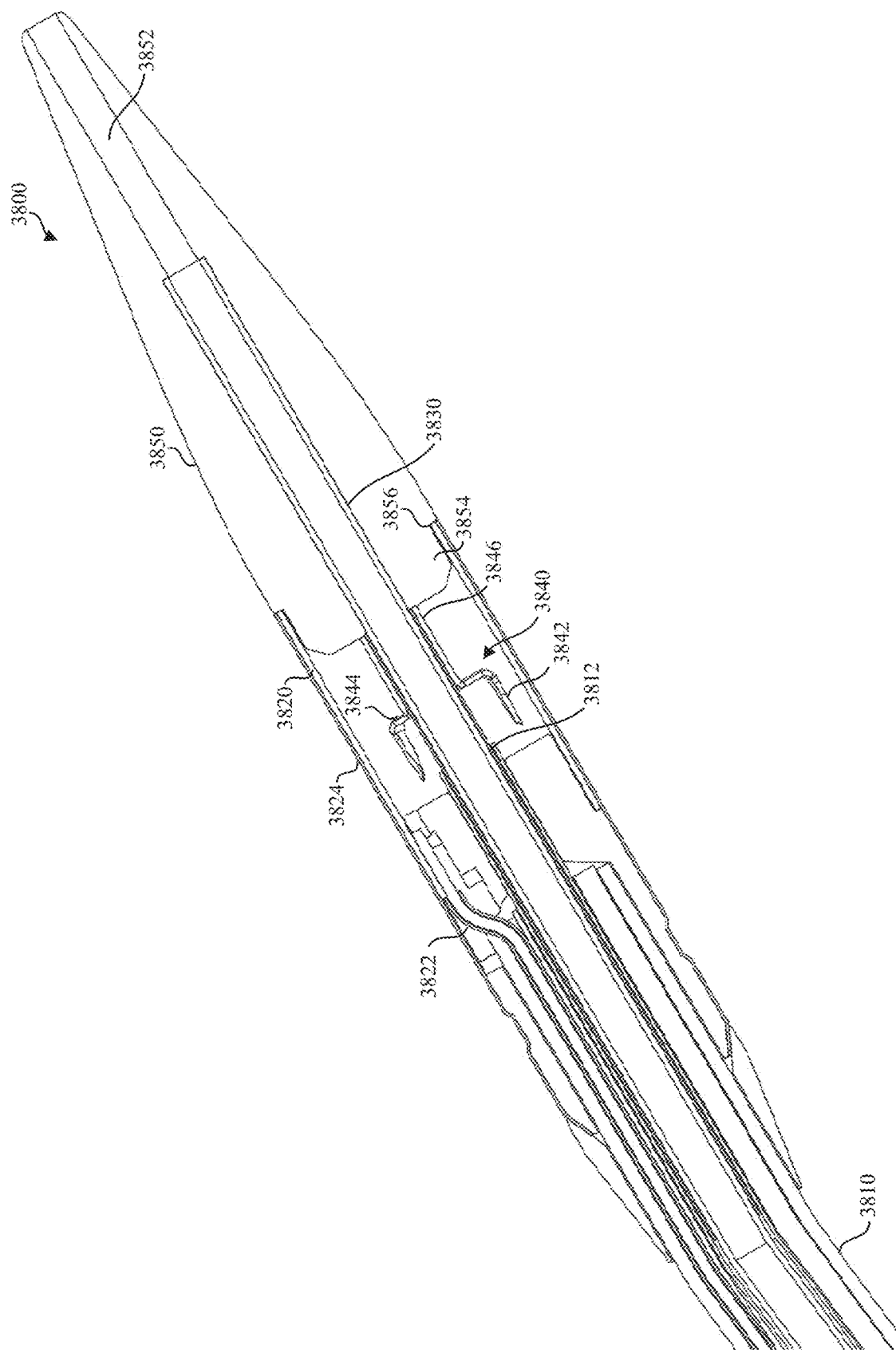
FIGS. 38A and 38B are cross-sectional side views of an illustrative variation of an ablation device in open and closed configurations.

FIG. 38A is a schematic cross-sectional side view of a variation of an ablation device (3800) in a closed configuration. In some variations, the ablation device (3800) may comprise a first catheter (3810) and a second catheter (3830). The first catheter (3810) may comprise a electrode (3820) such as a tubular electrode. The electrode (3820) may define a lumen configured to hold one or more portions of the second catheter (3830). The first catheter (3810) may further comprise a first catheter actuator (3822) (e.g., lead, electrical pull wire) coupled to the electrode (3820) and a signal generator (not shown). As described in more detail herein, the first catheter actuator (3822) may be configured to deliver electrical energy to the electrode (3820) as well as deflect a distal portion of the ablation device (3800) in the manner of a pull wire. In some variations, the first catheter (3810) may comprise an insulator (3824) configured to cover a portion of the electrode (3820). For example, the insulator (3824) may be configured to cover an outer surface of the electrode (3820) where a distal end and an inner surface of the electrode (3820) are uninsulated. In some variations, the first catheter (3810) may comprise a contrast agent lumen (3812) as described in more detail herein.

In some variations, the ablation device (3800) may comprise a second catheter (3830) slidably disposed within the first catheter (3810). The second catheter (3830) may comprise a barb (3840) and a dilator (3850) configured to engage the electrode (3820). In some variations, the barb (3840) may comprise a plurality of projections (3842, 3844) radially arranged that generally extend towards the electrode (3820). For example, the projections (3842) may comprise a distal portion configured to pierce tissue and the projections (3844) may comprise a proximal portion (3846) configured as a backstop to tissue.

In some variations, the dilator (3850) may be tapered and define a lumen (3852). In some variations, a guidewire (not shown) may be slidably disposed within the lumen (3852). In some variations, the dilator (3850) may comprise a proximal portion (3854) and an echogenic region (not shown). For example, the echogenic region may comprise a predetermined surface texture configured for visualization using ultrasonic imaging. The proximal portion (3854) of the dilator (3850) may be configured to engage the electrode (3820) in the closed configuration. That is, the proximal portion (3854) may be configured to be in a lumen of the electrode (3820) in the closed configuration of the ablation device (3800). In some variations, the dilator (3850) may comprise a mating surface (3856) configured to engage the electrode (3820). For example, the electrode (3820) and mating surface (3856) may be configured to compress tissue therebetween (not shown) as discussed in more detail with respect to FIG. 36A. The mating surface (3856) of the dilator (3850) may extend radially and/or lengthwise.

In the closed configuration, the barb (3840) may be enclosed by the first catheter (3810), electrode (3820), and dilator (3850). That is, the barb (3840) may be disposed within a lumen of the electrode (3820) when the proximal portion (3854) (e.g., mating surface (3856)) engages (e.g., is seated within) the electrode (3820). Accordingly, any tissue engaged by the barb (3840) may also be enclosed and secured within the ablation device (3800) in the closed configuration by one or more of the barb (3840) and electrode (3820). The proximal portion (3854) arranged within the lumen of the electrode (3820) may securely and coaxially attach the electrode (3820) to the dilator (3850). For example, the dilator (3850) may be secured to the first catheter (3810) to withstand dislodgment from a lateral load such as when the ablation device (3800) is tracked over a curved guidewire. Furthermore, the electrode (3820) securely engaged to the dilator (3850) may be configured to prevent the ablation device (3800) from catching (e.g., snagging) against a vessel, tissue (e.g., transseptal crossing), introducer, sheath, and the like during advancement and withdrawal through a body cavity. In some variations, between about 0.5 mm and about 2 mm of the proximal portion (3854) of the dilator (3850) may be disposed within the lumen of the electrode (3820) when the mating surface engages the electrode (3820).

Figure 36A:
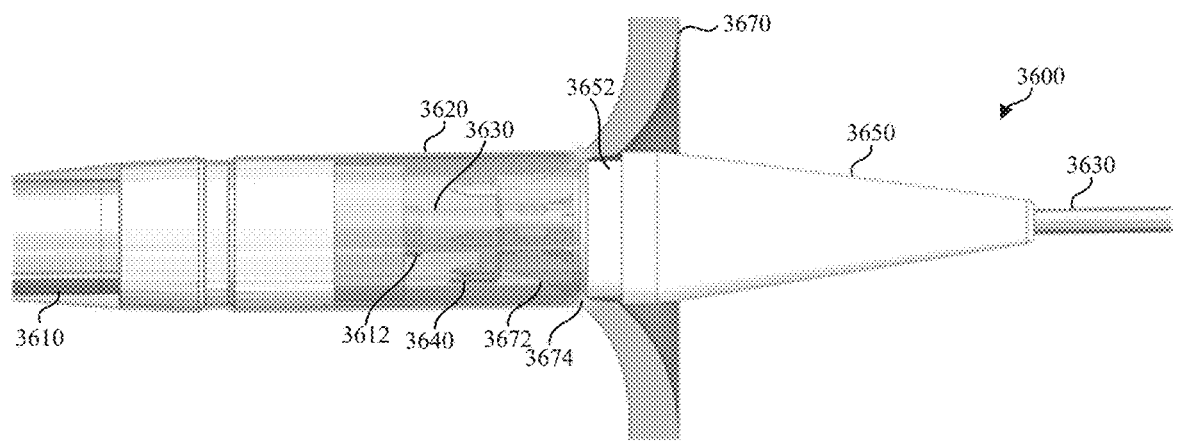
FIGS. 36A and 36B are side views of an illustrative variation of an ablation device in an endocardial space.
Figure 38B:
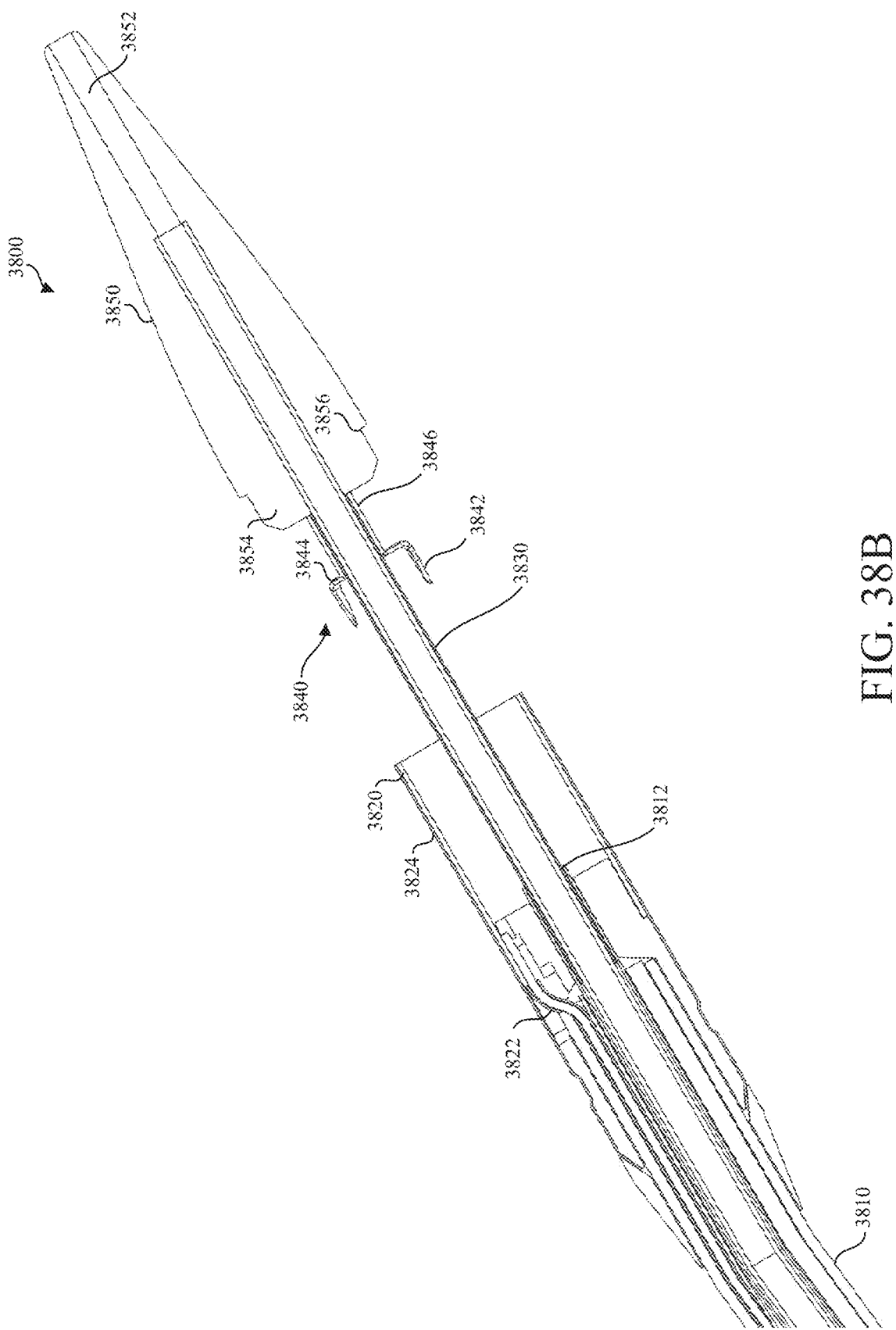

FIG. 38B is a schematic cross-sectional side view of a variation of the ablation device (3800) in an open configuration. The second catheter (3830) may be configured to translate relative to the first catheter (3810) via an actuation mechanism of a handle such as described herein with respect to FIGS. 39A and 39B. FIG. 36A illustrates an ablation device (3600) in a cutting configuration between the open configuration and closed configuration. The ablation device (3600) may correspond to the ablation device (3800).

In some variations, a proximal portion (3854) of the dilator (3850) may comprise a first step portion comprising a first diameter and a second step portion comprising a second diameter greater than the first diameter. The first step portion may be proximal to the second step portion. In some variations, the second step may comprise the mating surface (3856) configured to engage a distal end of the electrode (3820). In some variations, the mating surface (3856) may be substantially perpendicular to a longitudinal axis of the dilator (3850). In some variations, the first step may be configured to engage a sidewall of the electrode (3820) when the dilator (3850) engages the electrode (3820). In some variations, the dilator (3850) may be configured to attach to the first catheter (3810) when the dilator (3850) engages the electrode (3820).

Electrode

Generally, the electrodes described here may be configured to ablate tissue such as a portion of an interatrial septum of a patient to reduce blood pressure in a left atrium of a patient. In some variations, the electrode may engage the septum and be energized to excise a portion of septum tissue to form a predetermined opening between the left atrium and right atrium. For example, tissue may be heated using radiofrequency (RF) energy during an electrosurgical procedure. RF energy tissue ablation may be used to quickly and precisely cut tissue without significant damage to surrounding tissue. In some variations, RF energy may be delivered to tissue by an electrode to quickly and precisely cut tissue so as to form an anastomosis of a predetermined shape and size.

In some variations, tissue ablation characteristics may be controlled by the size, shape, and/or geometry of the conductive region of the electrode. For example, the electrode may comprise a thin, radial edge configured to apply high density energy to a small contact surface area of tissue being cut. This may cut tissue quickly and with less energy relative to an electrode having a larger contact surface area. In some variations, a distal end of the electrode may be angled (e.g., chamfered, beveled) relative to a longitudinal axis of the electrode to further reduce a contact surface area of the electrode with respect to tissue. In some variations, a width of the chamfered surface may be between about 0.025 mm and about 0.040 mm, including all ranges and sub-values in-between. For example, a width of the chamfered surface may be between about 0.05 mm and about 0.08 mm.

Furthermore, a small contact surface area of the electrode may aid compression of the tissue prior to ablation. For example, as shown in FIGS. 6A-6C and FIGS. 9A-9B, a distal end of the electrode (620, 920) may be configured to abut against a corresponding mating surface (654, 954). A smaller contact surface area of the electrode may increase the compression force applied to tissue against the mating surface. Compression of the tissue between the electrode and mating surface may provide numerous benefits. For example, reducing the thickness of the tissue to be cut via compression may allow the septum to be cut faster and with less energy. Furthermore, compressed tissue may hold (e.g., secure, lock) the tissue in place relative to the ablation device to ensure that only a predetermined portion of tissue is cut. In some variations, compression of the tissue during activation may fuse layers of tissue (e.g., left and right atrial septal layers) together during ablation, thereby reducing a surface area of exposed tissue along a perimeter of the anastomosis after tissue excision. In some variations, compression of tissue may be used to reduce the volume of tissue, thus enabling a larger volume of tissue to be contained within the lumen of the electrode following ablation, thereby allowing a relatively larger anastomosis to be formed.

In some variations, a shape of the opening in the interatrial septum may be based on a shape of the electrode. For example, the electrodes (420, 820) in respective FIGS. 4 and 8 may comprise a tubular shape that may be used to generate a generally circular opening. In some variations, at least a portion of a distal end of an electrode may be angled between about 5 degrees and about 75 degrees relative to a longitudinal axis of the electrode so as to form a chamfer and/or bevel. For example, at least a portion of a distal end of an electrode may be angled between about 30 degrees and about 60 degrees relative to a longitudinal axis of the electrode. For example, a distal end (628, 728) of the electrode (620, 720) in respective FIGS. 6C and 7C may be radially angled at about a 45 degree angle relative to the longitudinal axis of the electrode (620, 720).

As discussed herein, a chamfered electrode may reduce a contact surface area of the electrode and allow for increased compression force on tissue. In some variations, a corresponding mating surface of a dilator may be similarly chamfered to aid alignment and coupling of the dilator to the electrode as the dilator is withdrawn relative to the electrode. In some variations, at least a portion of a mating surface of a dilator may be angled between about 5 degrees and about 75 degrees relative to a longitudinal axis of the dilator. For example, at least a portion of a mating surface of a dilator may be angled between about 30 degrees and about 60 degrees relative to a longitudinal axis of the dilator. In this manner, the chamfered electrode may allow the dilator to seat itself into the electrode by providing tolerance for misalignment between the electrode and dilator due to, for example, tissue disposed therebetween.

In some variations, one or more portions of an electrode may be covered by an insulator (e.g., PTFE, ePTFE, PET, polyolefin, parylene, FEP, silicone, nylon, PEEK, polyimide) to reduce the contact surface area of the electrode. A relatively small contact surface area may reduce vapor bubble formation, as well as char formation and activation time of the electrode. In some variations, an inner surface of the electrode may remain uninsulated and serve as a conduction pathway for current to travel through the contained tissue during and after tissue excision. In some variations, conduction through the tissue may shrink the volume of excised tissue via dessication and/or denaturation of protein, thereby enabling containment of larger volumes of tissue.

Figure 11A:
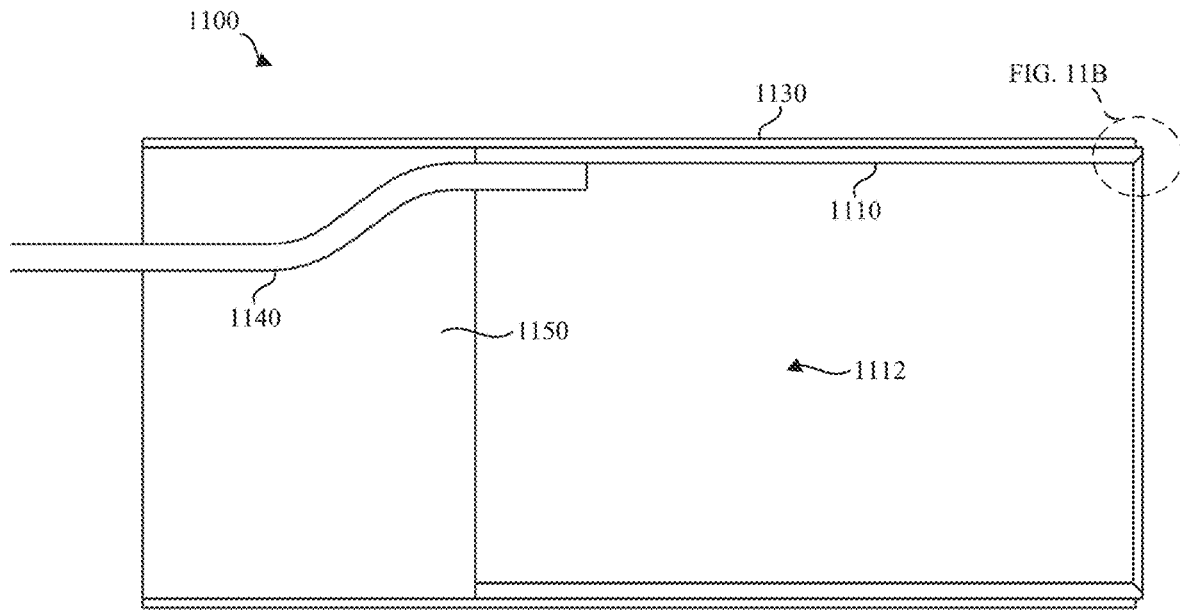
FIG. 11A is a schematic cross-sectional side view of an illustrative variation of an electrode of an ablation device.
Figure 11B:
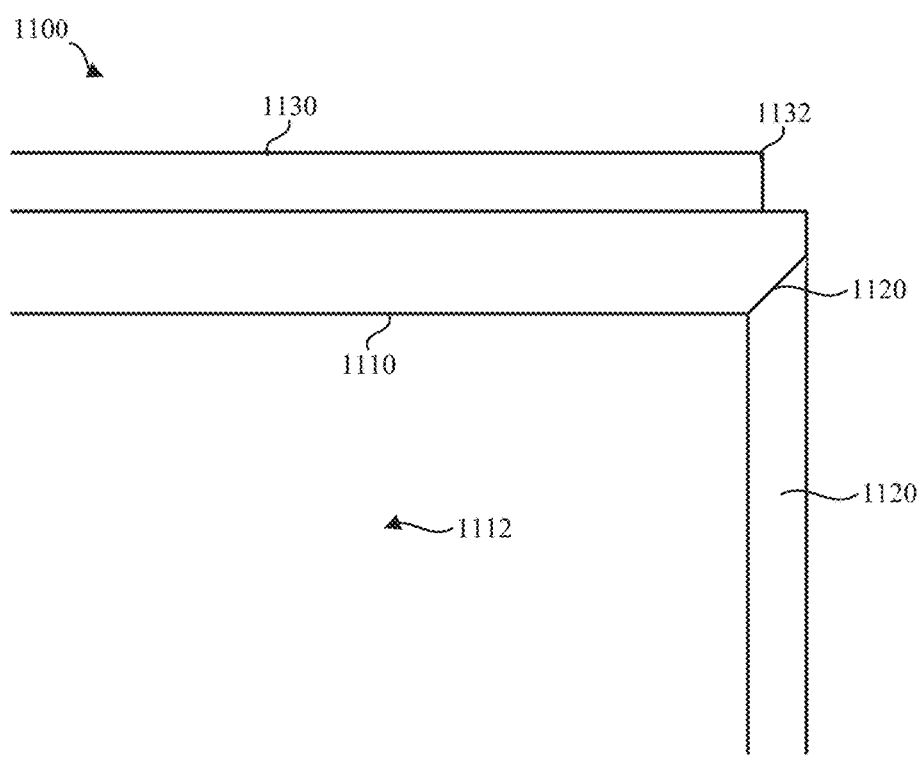
FIG. 11B is a detailed cross-sectional side view of a distal end of the electrode shown in FIG. 11A.
Figure 22:
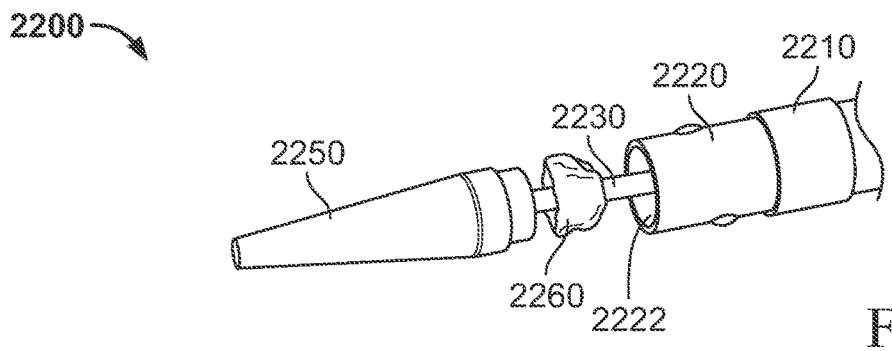
FIG. 22 is perspective view of an illustrative variation of an ablation device engaged to cut tissue.
Figure 27A:
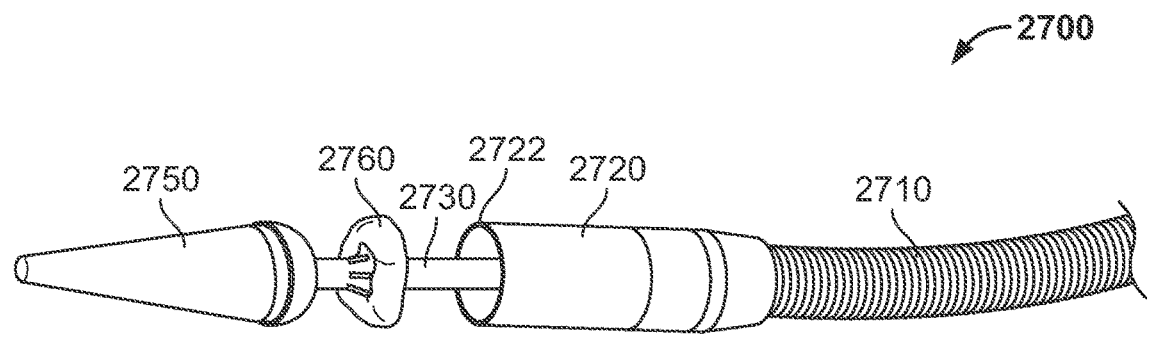
FIGS. 27A and 27B are perspective views of an illustrative variation of an ablation device engaged to cut tissue.
Figure 27B:
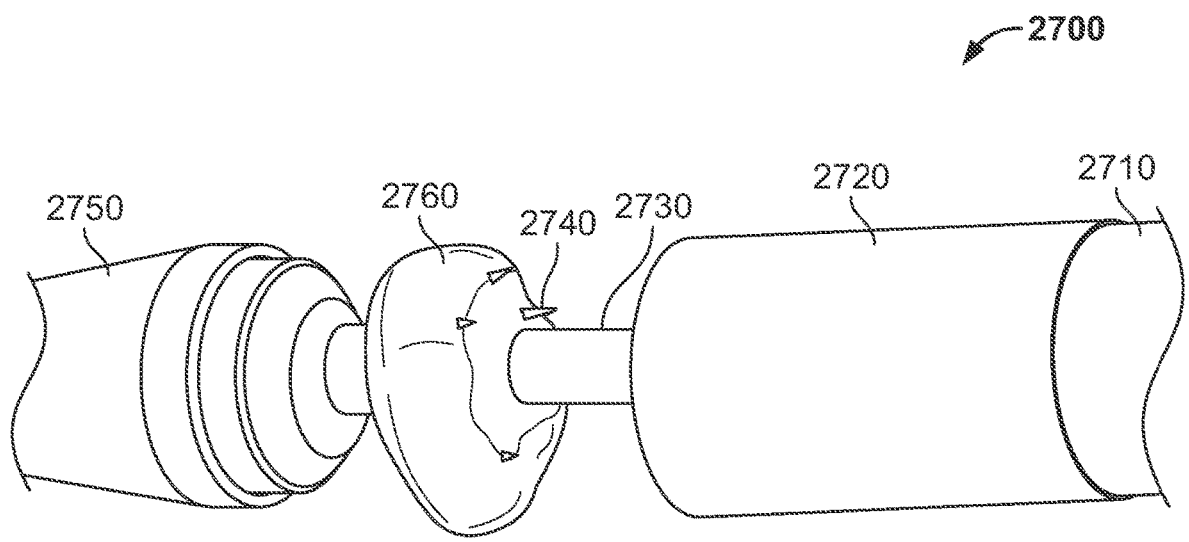
Figure 28A:
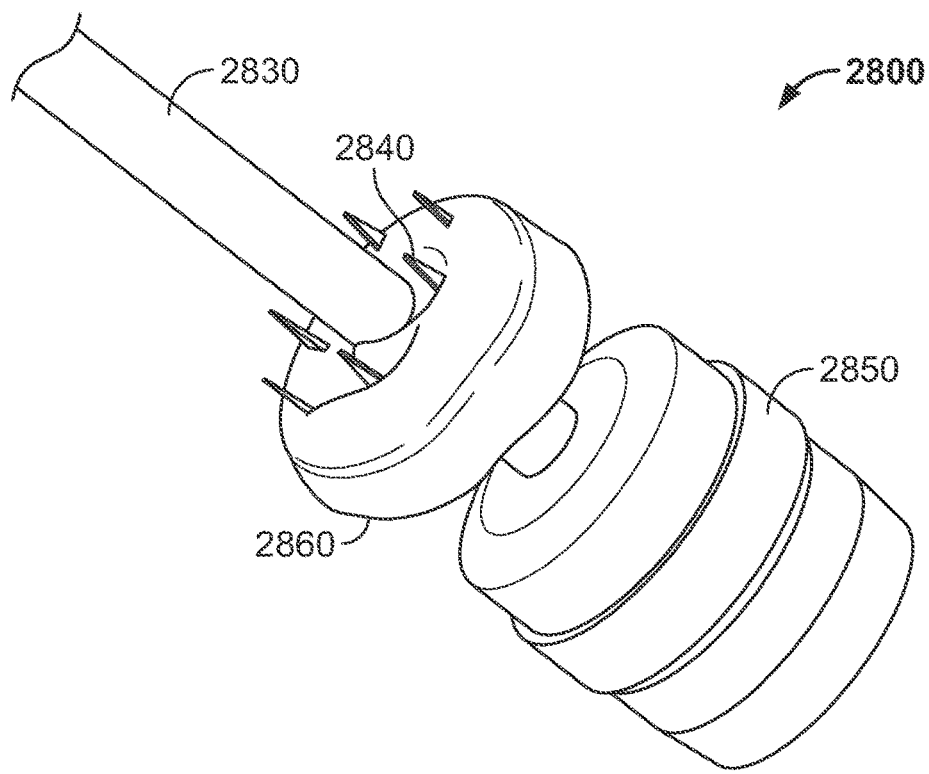
FIGS. 28A and 28B are perspective views of an illustrative variation of an ablation device engaged to cut tissue.
Figure 28B:
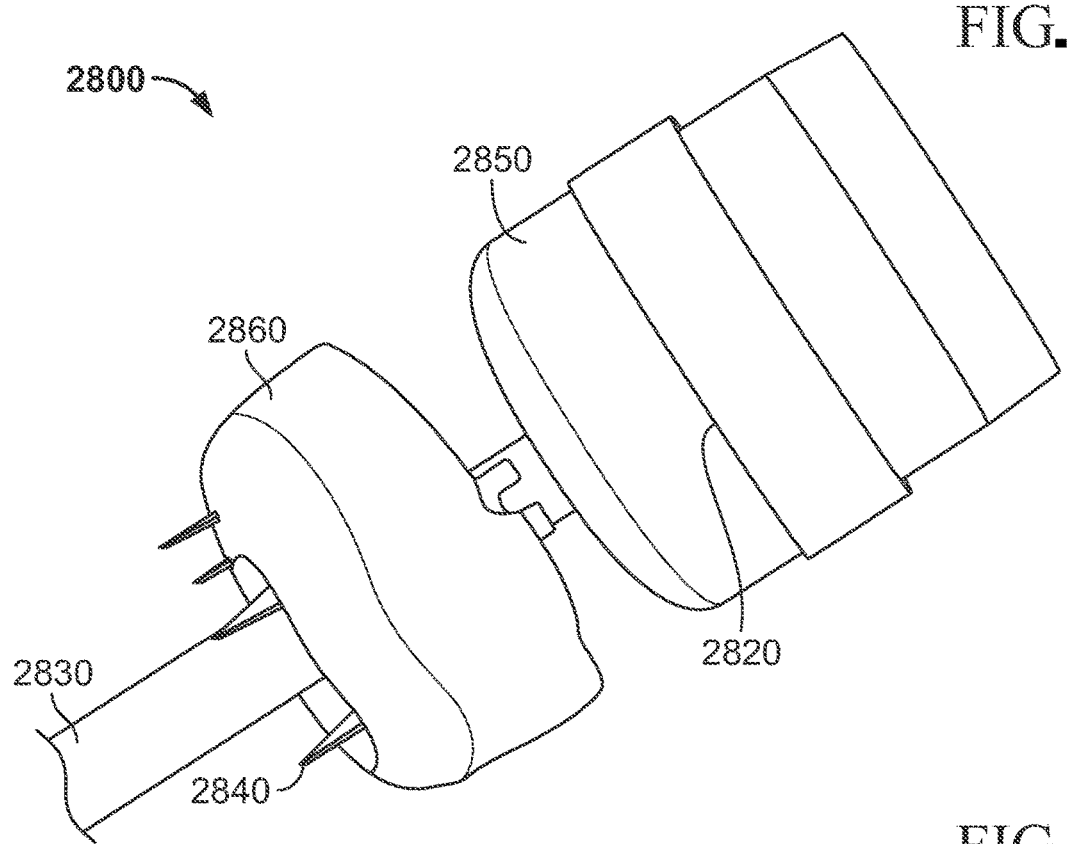

FIGS. 11A and 11B are schematic cross-sectional side views of an electrode (1110) of an ablation device (1100). In particular, a distal end of a first catheter may comprise the electrode (1110) having a distal end (1120), insulator (1130), lead (1140), and connector (1150). The electrode (1110) may have a tubular shape comprising a distal end (1120) and defining a lumen (1112). In some variations, the lumen (1112) may be configured to enclose one or more of a barb, tissue engaged by the barb, and a proximal portion of a dilator. FIG. 5A illustrates a cross-sectional perspective view of lumen (522) and FIG. 5B shows a barb (540) and a portion of a dilator (550) disposed within the lumen (522). Furthermore, as shown in FIG. 22, the lumen (2222) may have a volume sufficient to enclose a predetermined volume of tissue (2260). Similarly, FIGS. 27A and 27B are images including a predetermined volume of tissue (2760) that fit within a lumen of an electrode (2720). As yet another example, the tissue (2860) shown in FIGS. 28A and 28B is configured to fit within a lumen of an electrode (not shown). In some variations, the lumen may have a length of at least 1 mm. For example, the lumen may have a length between about 5 mm and about 4 cm.

In some variations, the connector (1150) may couple to each of the electrode (1110) and lead (1140). The insulator (1130) may be configured to cover an outer surface of one or more of the electrode (1110) and connector (1150). In some variations, the inner surface of the electrode (1110) may be uninsulated. In some variations, up to about 2 mm of an outer surface of an electrode may be uninsulated. For example, up to about 0.15 mm of an outer surface of an electrode may be uninsulated.

As shown in the detailed cross-sectional side view of FIG. 11B, a distal end (1120) of the electrode (1110) may be angled (e.g., chamfered, beveled) relative to a longitudinal axis of the electrode (1110). In some variations, the chamfer may extend radially along the distal end (1120). The distal end (1120) may comprise a single angle or a plurality of angles. For example, a surface of the distal end (1120) may comprise a sine-wave like shape where a corresponding mating surface of a dilator may comprise a corresponding sine-wave like shape. This may allow the respective mating surfaces of the electrode and dilator to contact and compress each other in a predetermined orientation.

In some variations, the electrode may comprise one or more biocompatible metals such as titanium, stainless steel, nitinol, palladium, silver, platinum, combinations thereof, and the like. In some variations, the electrode may comprise an atraumatic (e.g., blunt, rounded) distal edge such that the electrode does not puncture tissue when pressed against an opposing surface such as a mating surface of a dilator. For example, the electrode may engage and compress the tissue along its chamfered circumferential edge.

In some variations, the cut tissue may comprise a diameter of between about 1 mm and about 1.5 cm, including all ranges and sub-values in-between. For example, the cut tissue may comprise a diameter of between about 0.5 mm and about 12 mm. For example, the cut tissue may comprise a diameter of between about 6 mm and about 9 mm.

In some variations, the heating of tissue may shrink the tissue prior to cutting. In some variations, the heating of tissue may shrink the tissue after cutting. In some variations, the tissue may be heated to a predetermined range of temperatures. In some variations, the tissue to be cut may be heated to at least about 60° C., about 70° C., about 80° C., about 90° C., and about 100° C. for a predetermined amount of time. In some variations, the tissue to be cut may be heated between about 50° C. and about 100° C. for a predetermined amount of time. In some variations, only the tissue to be cut may be heated, while in other variations, only part of the tissue to be cut may be heated. In some variations, the electrode may be configured to rotate, oscillate, and/or vibrate during and subsequent to energy delivery to prevent, minimize, and/or disrupt char formation.

In some variations, the electrode may be connected by a lead (e.g., conductive wire) to a signal generator. The lead may extend from a proximal portion of the first catheter to the electrode at a distal portion of the first catheter. One or more portions of the lead may be insulated. The lead may be configured to sustain a predetermined voltage potential without dielectric breakdown of its corresponding insulation.

Figure 12A:
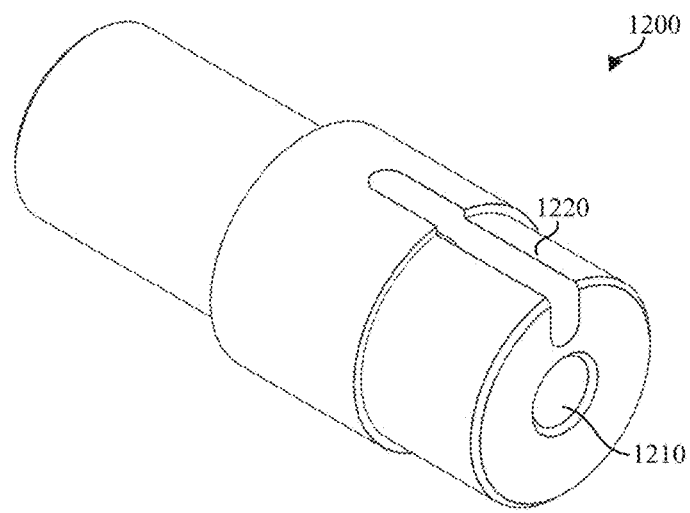
FIG. 12A is a schematic perspective view of an illustrative variation of a connector of an ablation device.
Figure 12B:
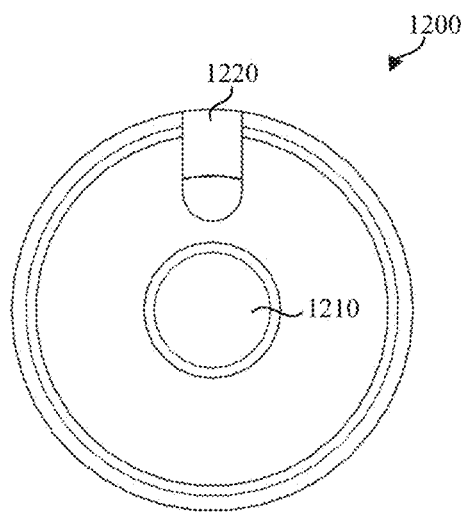
FIG. 12B is a schematic front view of an illustrative variation of a connector of an ablation device.
Figure 12C:
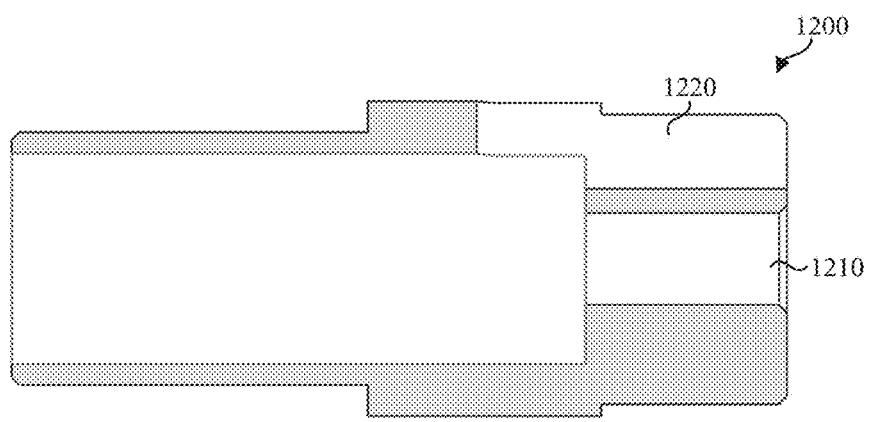
FIG. 12C is a schematic cross-sectional side view of an illustrative variation of a connector of an ablation device.

FIGS. 12A and 12B are respective perspective and front views of a connector (1200) of an ablation device. FIG. 12C is a cross-sectional side view of the connector (1200). In some variations, the connector (1200) may be configured to couple an electrode and a lead to a shaft of a first catheter (not shown for the sake of clarity). The connector (1200) may comprise a lumen (1210) configured to slidably dispose a second catheter, and a channel (1220) configured for a distal end of a lead. In some variations, at least a portion of the inner surface of the connector (1200) may be lubricious to aid translation of the second catheter relative to the connector (1200). For example, an inner surface of the connector (1200) may comprise a layer of PTFE to facilitate lubricious translation and/or rotation of a second catheter slidably disposed within the lumen (1210). In some variations, a connector (1200) may comprise a vent lumen (not shown) configured to vent fluid (e.g., air, heat, liquid) from a lumen of the electrode to a lumen of a first catheter.

In some variations, the connector (1200) may comprise a length of at least 0.1 mm. For example, the connector (1200) may comprise a length of between about 1 mm and about 2 cm, and between about 2 mm and about 7 mm. In some variations, the lumen (1210) may comprise a length of at least 0.1 mm. For example, the lumen (1210) may comprise a length of between about 1 mm and about 1 cm. In some variations, the channel (1220) may comprise a length of at least 0.1 mm. For example, the channel (1220) may comprise a length of between about 1 mm and about 5 mm.

In some variations, the systems disclosed herein may comprise a return electrode (e.g., RF energy sink) to draw RF energy out of the patient. In some variations, a second catheter may comprise a return electrode. In some variations, the return electrode may be external to and in contact with the return electrode (e.g., a skin patch electrode, grounding pad). For example, a set of return electrodes may be disposed on a back of a patient to allow current to pass from the electrode through the patient and then to the return electrode. For example, one or more return electrodes may be disposed on a skin of a patient. A conductive gel may be applied between the return electrodes and the skin to improve contact.

Insulator

Generally, the insulators described here may be configured to electrically isolate one more portions of the electrode and/or catheters of the ablation device. In some variations, the insulator may comprise one or more of a poly(p-xylylene) polymer (e.g. parylene C, parylene N), polyurethane (PU), polytetrafluoroethylene (PTFE), expanded PTFE (ePTFE), polyimide (PI), polyester, polyethylene terephthalate (PET), PEEK, polyolefin, silicone, copolymer, a ceramic, combinations thereof, and the like.

Barb

Generally, the barbs described here may be configured to engage tissue such as an interatrial septum of a patient to control a size and shape of the septum tissue to be cut. In some variations, a portion of septum tissue may be engaged by one or more projections of the barb and stretched across one or more projections to hold tissue in place before and after tissue ablation. In some variations, the projections may be configured to penetrate a predetermined distance into the tissue or through the tissue. For example, the projections may be configured to penetrate through multiple layers of the interatrial septum (e.g., one or more left atrium layers and right atrium layers) to secure the septum tissue to the barb while maintaining the structural integrity of the septum as a whole. In some of these variations, penetration of the projections through the tissue may hold the tissue to the barb to reduce the shearing strain of the tissue as it is pulled into the electrode, thereby improving the consistency and shape (e.g., cylindricity) of the cut. That is, the barb may be configured to capture but not tear tissue such that the tissue may remain engaged by the barb throughout an electrosurgical procedure.

For example, the barb may be configured to prevent tearing by distributing pressure as tissue is engaged and pulled. For example, the engaged tissue may form a generally conical tent-like shape over the barb to apply tension to the septum. In some variations, a barb may be configured to provide counter tension to the interatrial septum during energization of the electrode so as to minimize any unintended tissue deformation, rotation, and displacement due to unbalanced forces (e.g., tissue motion due to the heart beating). The engaged tissue and barb may be withdrawn into a lumen of an ablation device to hold and secure the tissue during tissue ablation. In some variations, the size of an anastomosis may depend on the distance the barb is withdrawn into the electrode such that a size of an anastomosis may be independent of the diameter of the ablation device. This allows an ablation device having an electrode with a fixed diameter to form an anastomosis having a diameter larger than that of the electrode. The size (e.g., diameter, length) and shape of the barb should be such that it may fit within a lumen of an electrode while engaged to tissue. In some variations, a diameter of an opening in tissue may be calculated using equation (1):

$$D = 2\sqrt{\left(\frac{d}{2}\right)^2 + z^2} \tag{1}$$

where, D is a diameter of the opening, d is an inner diameter of an electrode, and z is a distance the tissue is pulled into the electrode.

Figure 13A:
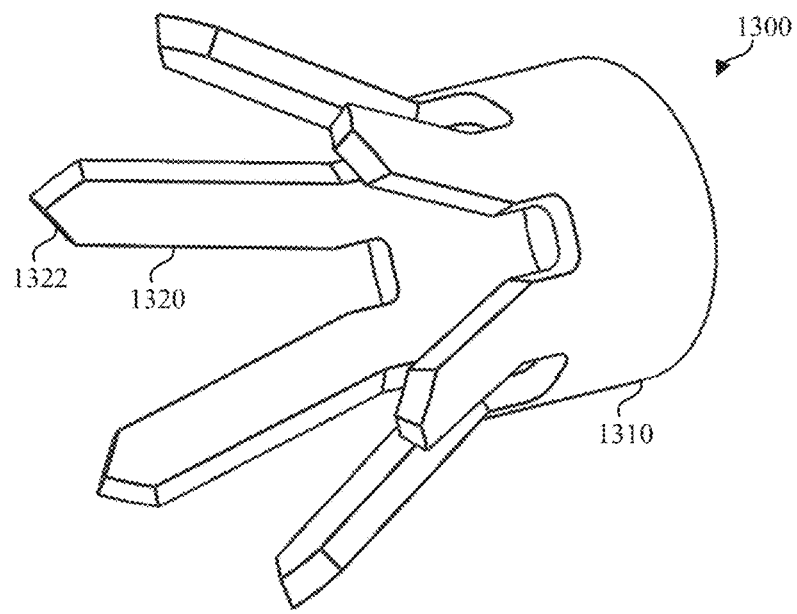
FIG. 13A is a schematic perspective view of an illustrative variation of a barb of an ablation device.
Figure 13B:
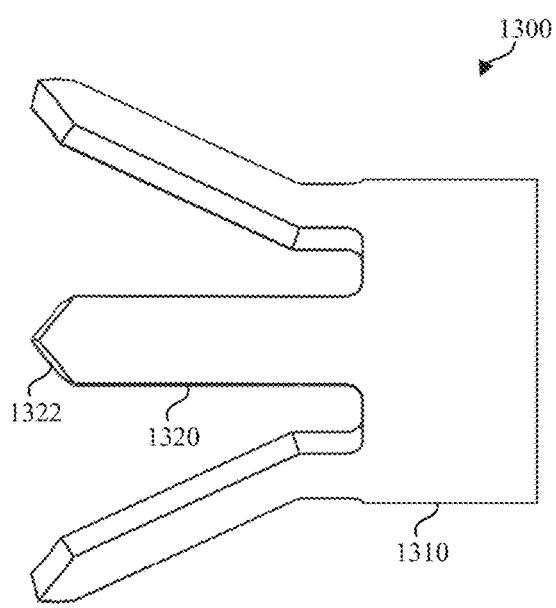
FIG. 13B is a schematic side view of an illustrative variation of a barb of an ablation device.
Figure 13C:
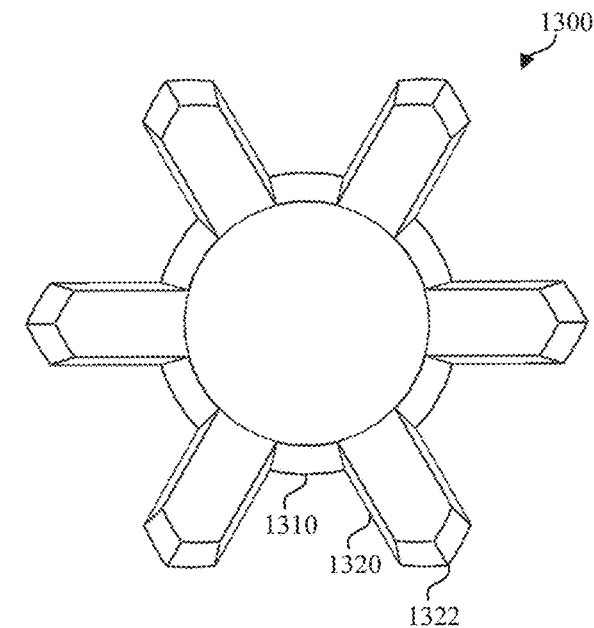
FIG. 13C is a schematic front view of an illustrative variation of a barb of an ablation device.

FIGS. 13A-13C depict various views of a barb (1300) of an ablation device. The barb (1300) may comprise a base (1310) and one or more projections (1320) (e.g., prongs) having a proximal end comprising a tissue engagement portion (1322) (e.g., point). The base (1310) may be generally cylindrical and configured to couple to a proximal portion of a dilator and a shaft of a second catheter (not shown). For example, the base (1310) may be proximal to a dilator of the second catheter.

One or more of the projections (1320) may couple to a proximal end of the base (1310). In some variations, the projection (1320) may comprise an elongate element. For example, the barb (1300) may comprise at least one projection (1320). In some variations, the projections (1320) may be spaced apart substantially equally about a circumference of the base (1310). In some variations, each of the projections (1320) may have the same or different lengths. In some variations, a length of the barb (1300) may be between about 0.1 mm and about 5 cm. In some variations, one or more of the projections (1320) may be linear, bent, curvilinear, rounded, arcuate, and the like.

In some variations, the projection (1320) may comprise one or more tissue engagement portions (1322). The tissue engagement portion (1322) and/or projection (1320) may be configured to engage tissue while not tearing the tissue to prevent a loss of tissue integrity. In some variations, the tissue engagement portion (1322) may be configured to pierce or penetrate through the tissue. In some variations, the geometry and size of each tissue engagement portion (1322) may be the same or different. For example, the tissue engagement portion (1322) may comprise a sharp point or a blunt, atraumatic end. In some variations, the tissue engagement portion (1322) may comprise one or more secondary structures (e.g., serrations) to prevent tissue from sliding down the projection (1320). In some variations, the tissue engagement portion (1322) may comprise an angle of between about 10 degrees and about 90 degrees relative to a longitudinal axis of its projection (1320). In some variations, a length of the projection (1320) and/or tissue engagement portion (1322) may be between about 0.1 mm and about 2 cm.

In some variations, the projections (1320) may be generally linear, but may be angled relative to a longitudinal axis of the base (1310). For example, the projections (1320) may be configured to splay outward to catch and engage tissue. In some variations, the projections may comprise one or more curved or angulated portions. In some variations, tissue may be configured to engage one or more portions of the projection (1320). In some variations, a projection of the barb may be angled between about 5 degrees and about 60 degrees relative to the longitudinal axis of the base (1310), including all values and sub-ranges in-between. For example, the projection (1320) may comprise an angle of between about 30 degrees and about 45 degrees. Each projection (1320) may have the same angle or a different angle relative to the longitudinal axis.

In some variations, the projection (1320) may be configured to engage a predetermined length and/or volume of tissue. For example, the projection (1320) may comprise a proximal portion configured as a barrier (e.g., backstop, wall) against additional tissue engagement (e.g., advancement, penetration), thereby reducing tissue tearing.

Figure 14:
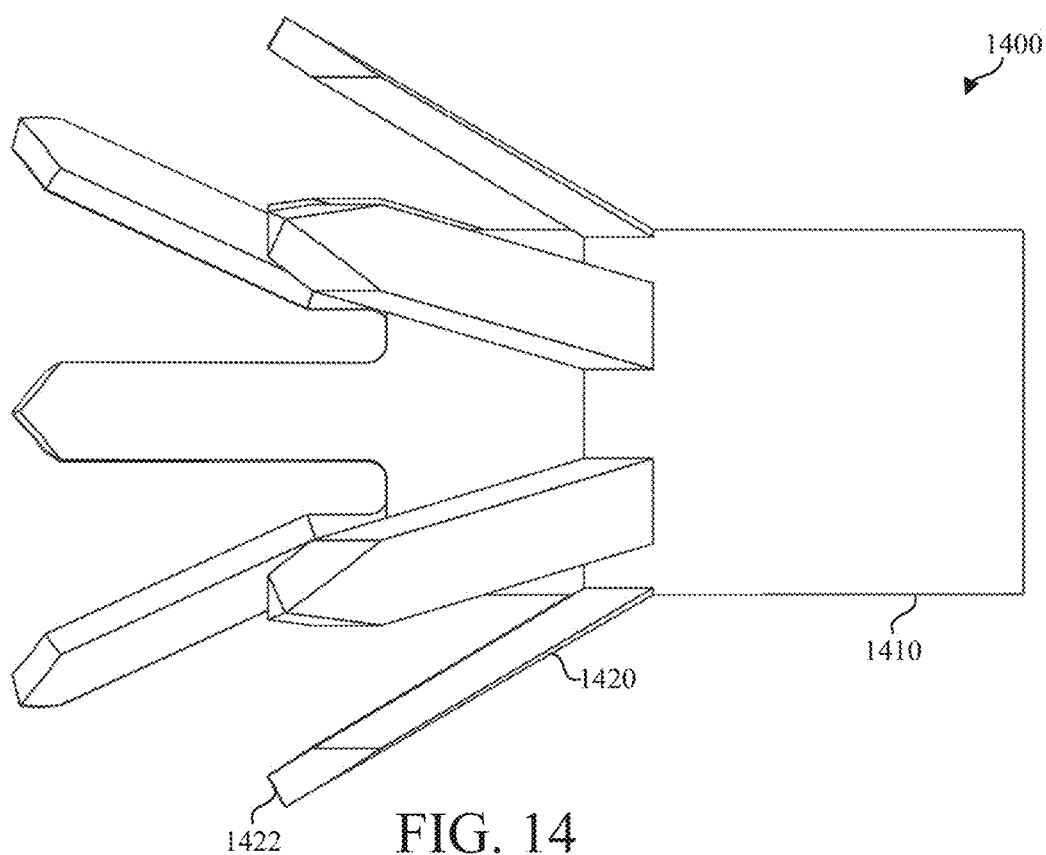
FIG. 14 is a schematic side view of an illustrative variation of a barb of an ablation device.

FIG. 14 is a schematic side view of a barb (1400) of an ablation device. The barb (1400) may comprise a base (1410) and one or more projections (1420) having a proximal end comprising a tissue engagement portion (1422). The projections (1420) of the barb (1400) may be angled in a similar manner as the barb (1300) of FIGS. 13A-13C. In some variations, a barb may comprise between about 2 projections and about 12 projections, including all values and sub-ranges in-between. For example, a barb may comprise between about 5 projections and about 7 projections.

Figure 15A:
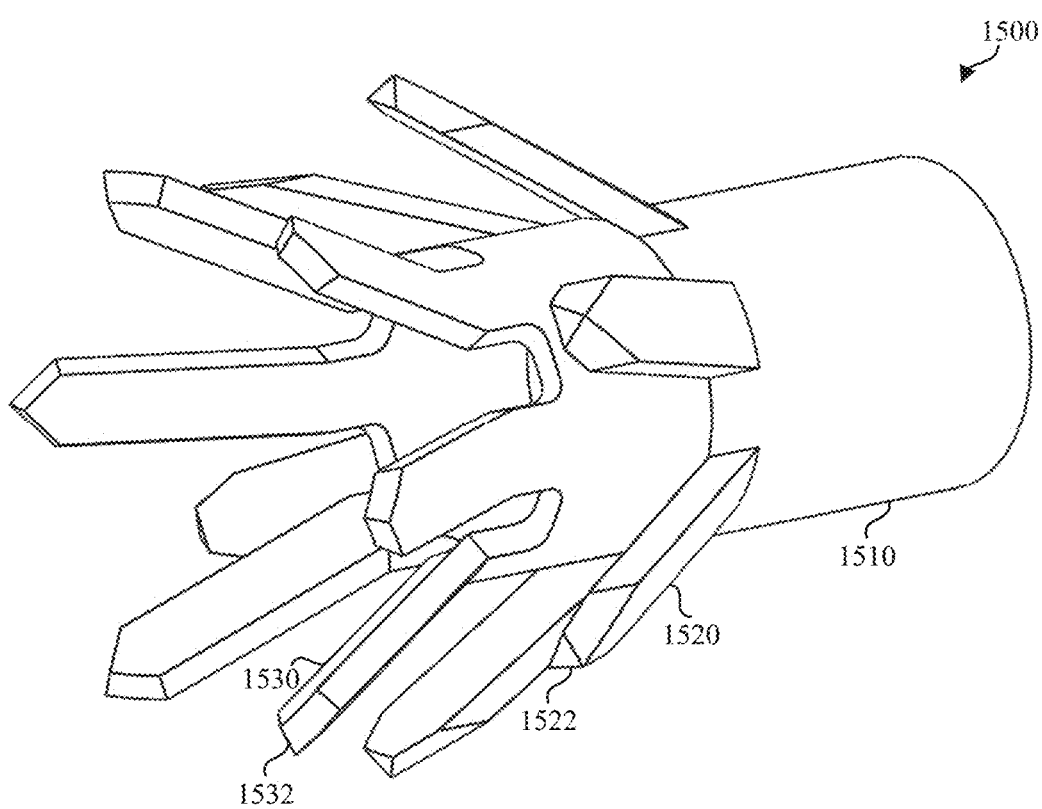
FIG. 15A is a schematic perspective view of an illustrative variation of a barb of an ablation device.
Figure 15B:
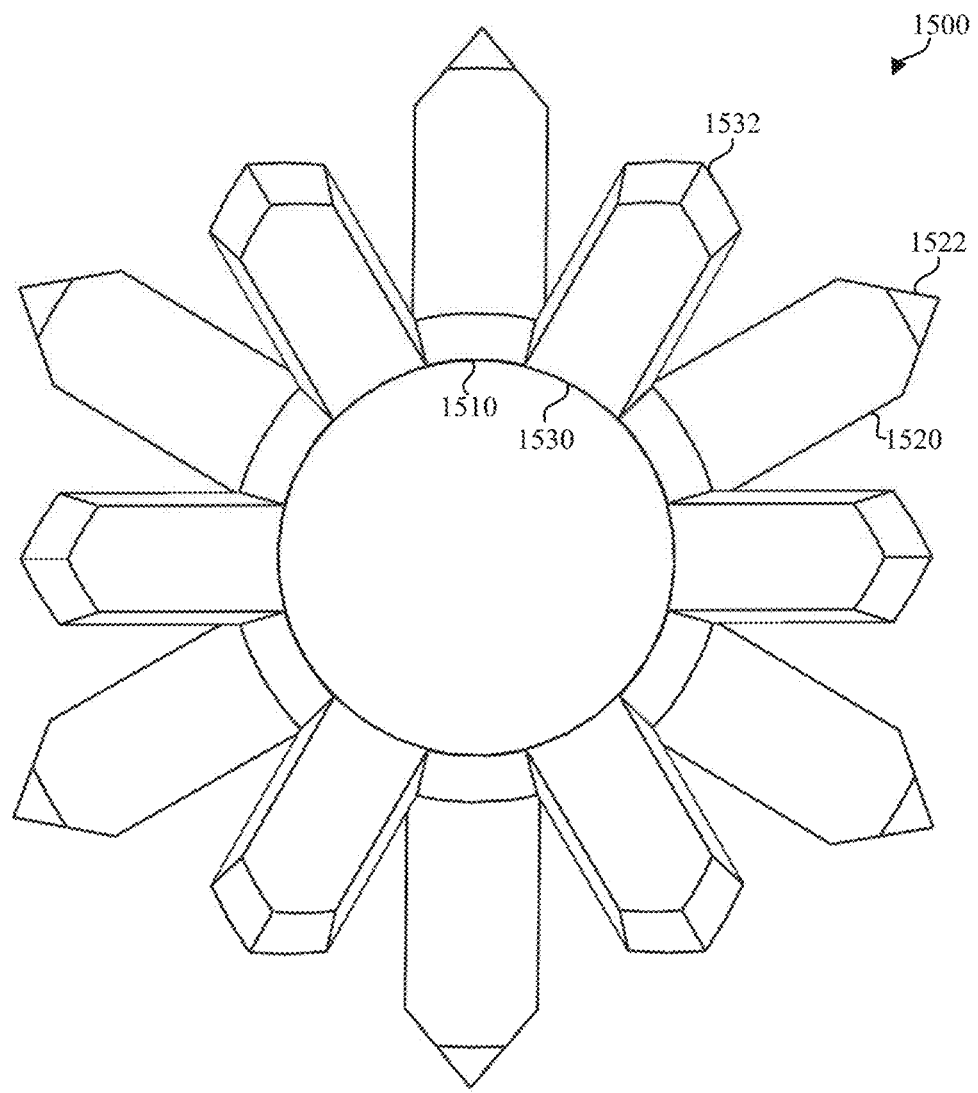
FIG. 15B is a schematic front view of an illustrative variation of a barb of an ablation device.

FIG. 15A is a schematic side view of a barb (1500) of an ablation device. FIG. 15B is a front view of the barb (1500). The barb (1500) may comprise a base (1510) and one or more projections (1520, 1530) having respective proximal ends each comprising a respective tissue engagement portion (1522, 1532). In some variations, one or more projections (1520, 1530) may be configured in rows along a length of the barb (1500). For example, the barb (1500) may comprise one or more rows of projections (1520, 1530). In some variations, the rows of projections (1520, 1530) may be staggered such as shown in FIGS. 15A and 15B. Tissue engaged to the barb (1500) may form a generally conical tent-like shape.

Figure 16:
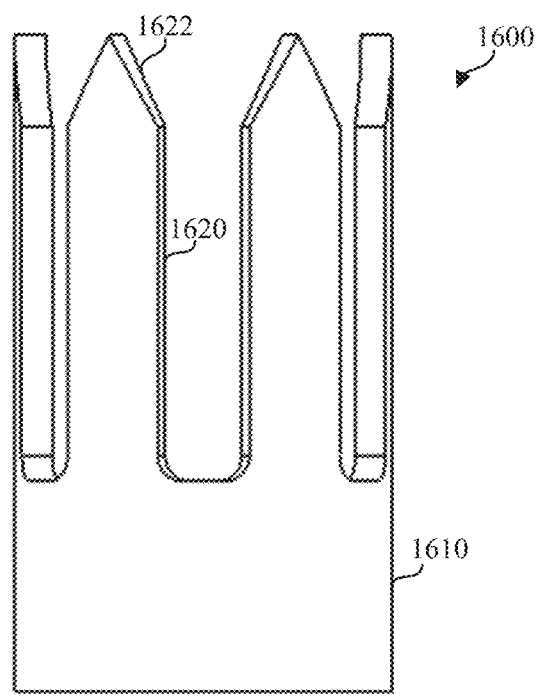
FIG. 16 is a schematic side view of an illustrative variation of a barb of an ablation device.
Figures 17A, 17B:
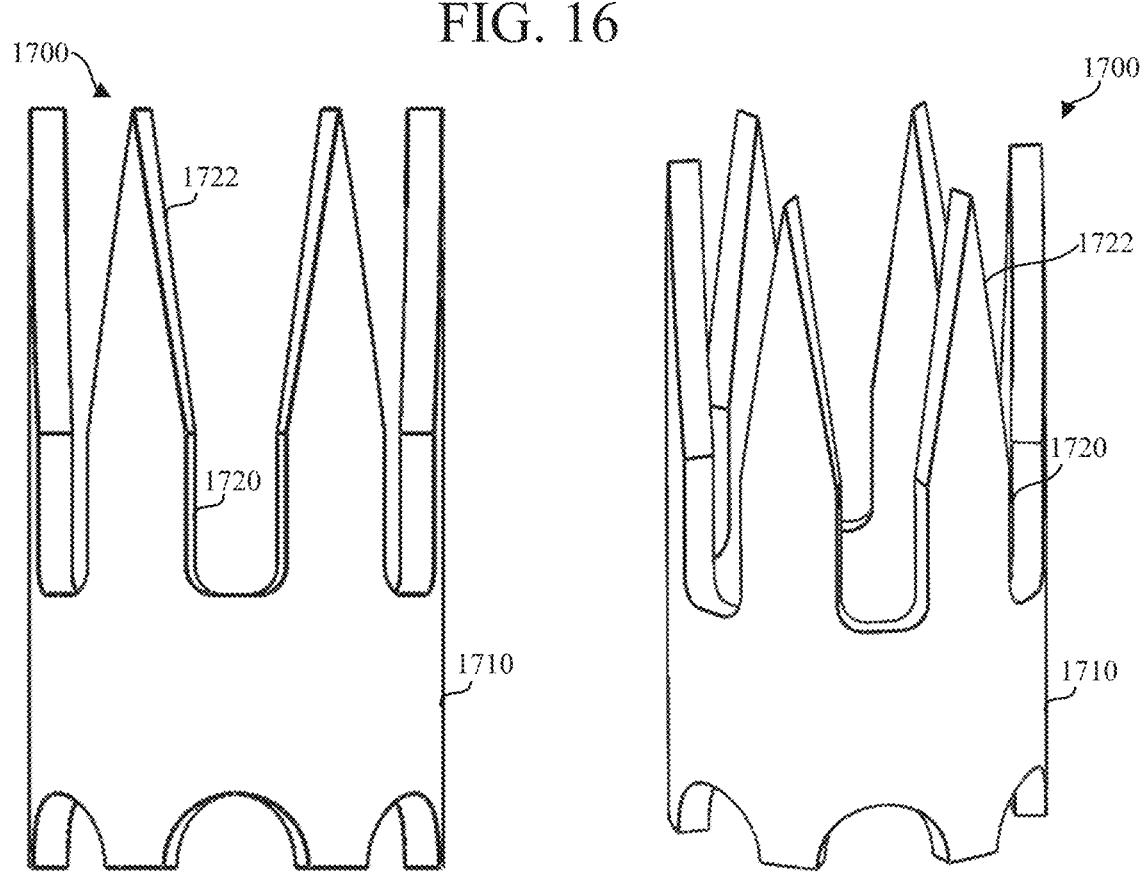
FIGS. 17A and 17B are schematic side and perspective views of an illustrative variation of a barb of an ablation device.
Figure 41A:
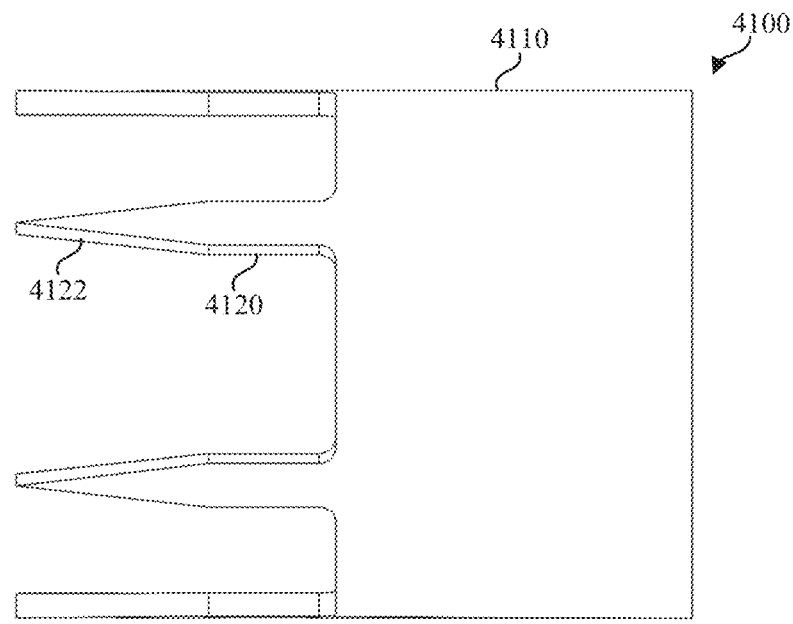
FIGS. 41A and 41B are schematic side and perspective views of an illustrative variation of a barb of an ablation device.
Figure 41B:
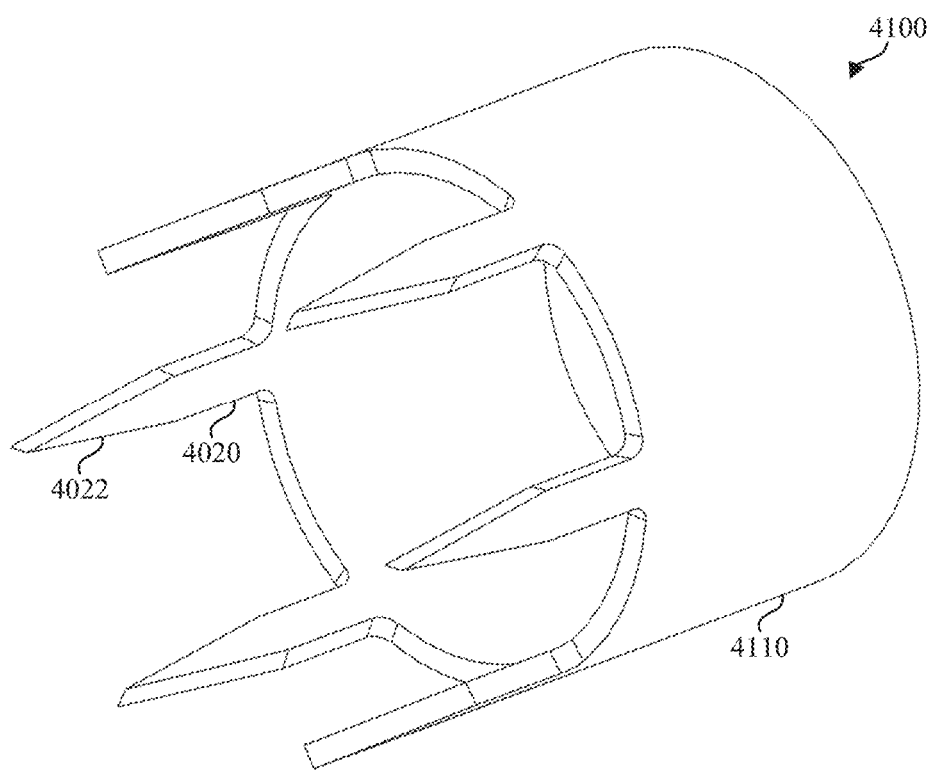

FIG. 16 is a schematic side view of a barb (1600) of an ablation device. The barb (1600) may comprise a base (1610) and one or more projections (1620) having a proximal end comprising a tissue engagement portion (1622). The projections (1620) may be parallel to a longitudinal axis of the base (1610). FIGS. 17A and 17B are respective schematic side and perspective views of a barb (1700) of an ablation device. The barb (1700) may comprise a base (1710) and one or more projections (1720) having a proximal end comprising a tissue engagement portion (1722). The tissue engagement portions (1722) may extend along a majority of a length of the projection (1720). In some variations, the base (1610) may comprise a diameter less than a diameter of an electrode. In some variations, the projections (1620, 1720) and tissue engagement portions (1622, 1722) may comprise a length configured to pierce through an interatrial septum. One or more tissue engagement portions (1722) may comprise a length, as shown in FIGS. 17A and 17B that may aid piercing and/or penetration of tissue with reduced force due to an increased taper FIGS. 41A and 41B are respective schematic side and perspective views of a barb (4100) of an ablation device. The barb (4100) may comprise a base (4110) and one or more projections (4120) having a proximal end comprising a tissue engagement portion (4122). In some variations, the projections (4120) and tissue engagement portions (4122) may comprise a length configured to pierce through an interatrial septum. One or more tissue engagement portions (4122) may comprise a length, as shown in FIGS. 41A and 41B that may aid piercing and/or penetration of tissue.

Figure 26A:
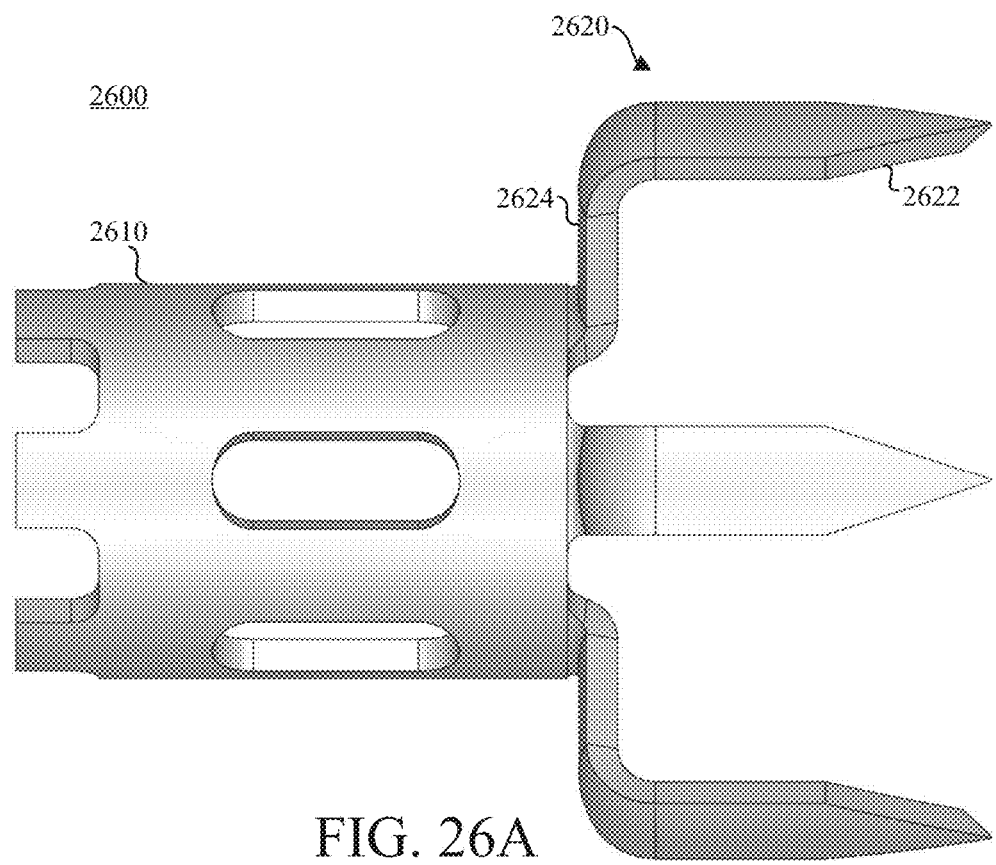
FIG. 26A is a schematic side view of an illustrative variation of a barb of an ablation device.
Figure 26B:
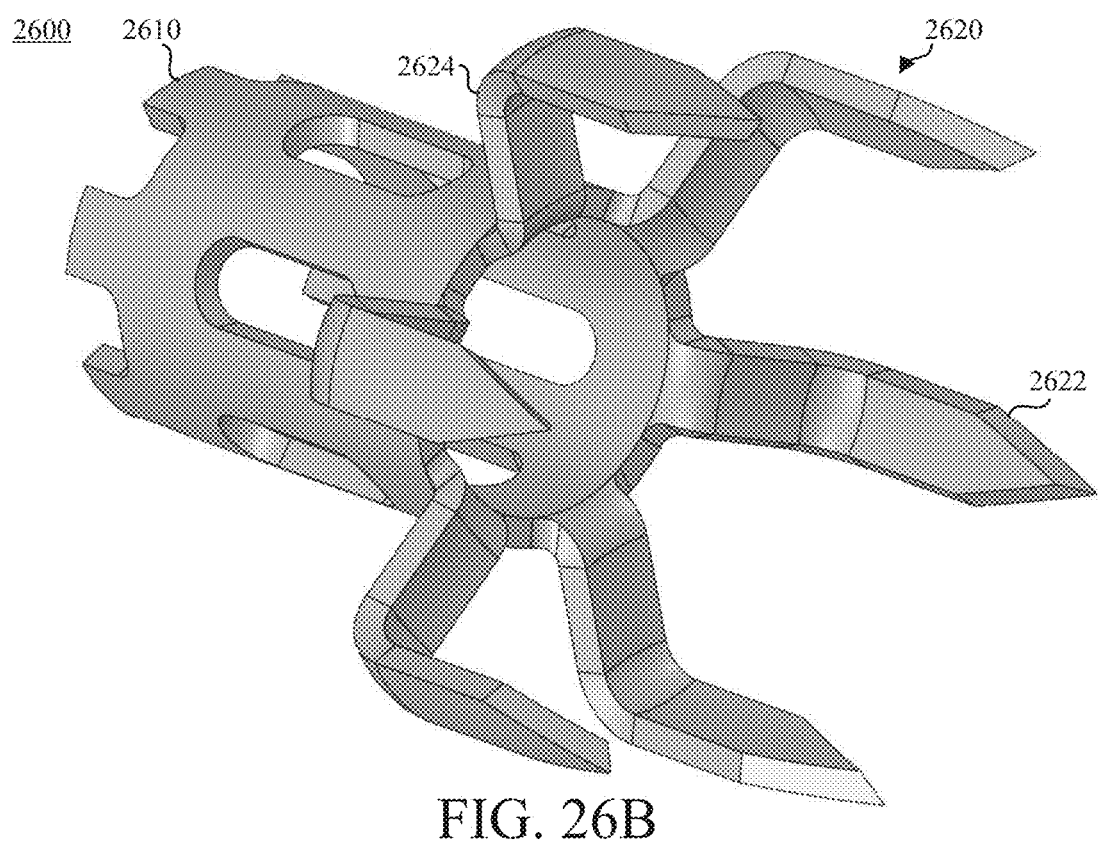
FIG. 26B is a schematic perspective view of an illustrative variation of a barb of an ablation device.
Figure 26C:
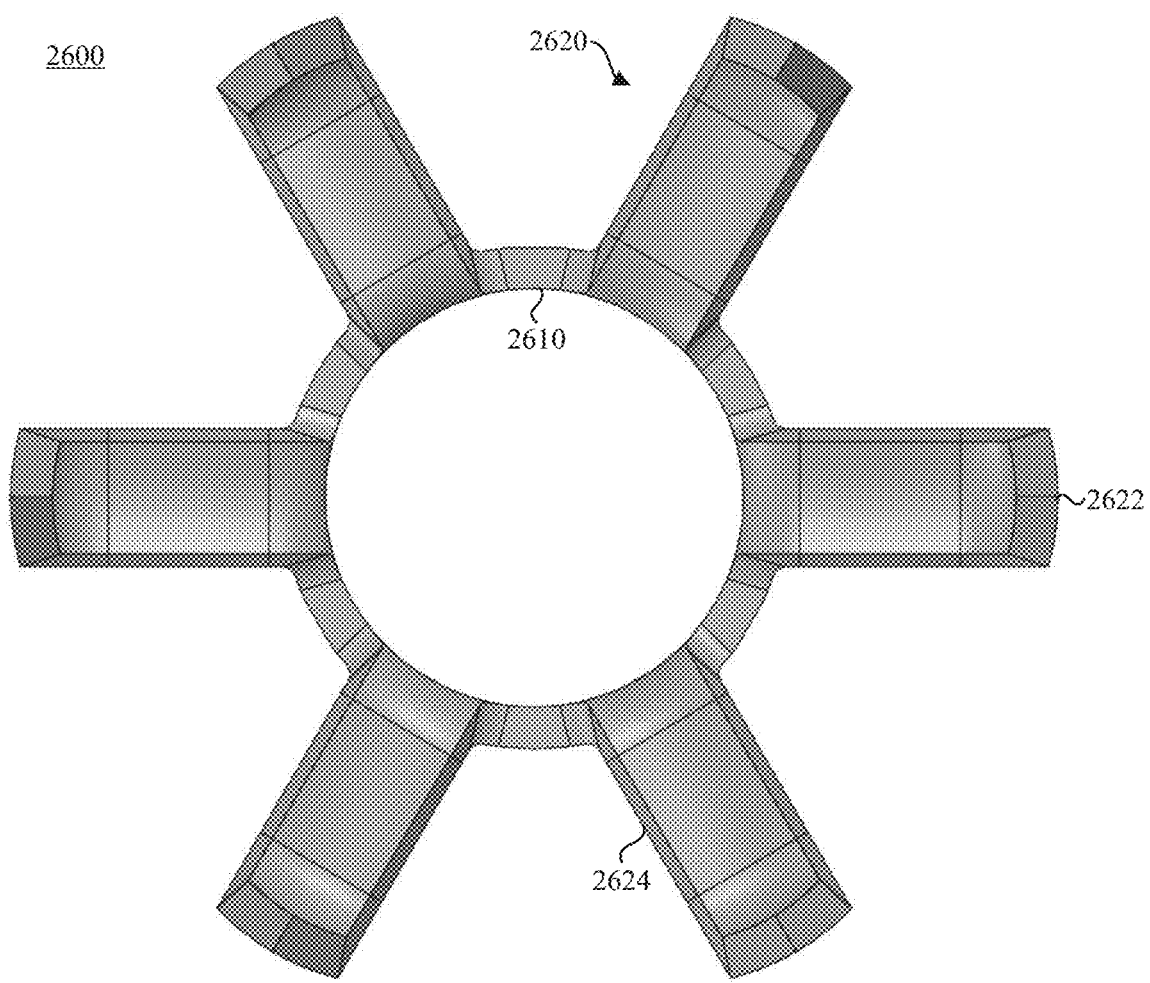
FIG. 26C is a schematic front view of an illustrative variation of a barb of an ablation device.

FIGS. 26A-26C depict various views of a barb (2600) of an ablation device. The barb (2600) may comprise a base (2610) and one or more projections (2620) (e.g., prongs, tines). The projection (2620) may comprise a first portion (2624) and a distal portion (e.g., tissue engagement portion) (2622) (e.g., tip, point). In some variations, the first portion (2624) may be angled relative to the second portion (2622). For example, the projection (2620) may comprise a bend where the first portion (2624) is substantially perpendicular to the second portion (2622). The base (2610) may be generally cylindrical and configured to couple to a proximal portion of a dilator and a shaft of a second catheter (not shown). For example, the base (2610) may be proximal to a dilator of the second catheter.

One or more of the projections (2620) may couple to an end of the base (2610). In some variations, the projection (2620) may comprise an elongate element. For example, the barb (2600) may comprise at least one projection (2620). In some variations, the projections (2620) may be spaced apart substantially equally about a circumference of the base (2610) and extended away from a longitudinal axis of the base (2610). In some variations, each of the projections (2620) may have the same or different lengths. In some variations, a length of the barb (2600) may be between about 0.1 mm and about 5 cm. In some variations, a length of the proximal portion to a length of the distal portion may be in a ratio between about 2:3 and about 1:5. In some variations, one or more of the projections (2620) may be linear, bent, curvilinear, rounded, arcuate, and the like. For example, projection (2610) may comprise an "L" shape, "J" shape, or "C" shape where the projections (2610) collectively define a diameter greater than a diameter of the base (2610).

In some variations, the distal portion (2622) of a projection (2620) may comprise one or more tissue engagement portions (2622). The tissue engagement portion (2622) and/or projection (2620) may be configured to engage tissue while not tearing the tissue to prevent a loss of tissue integrity. In some variations, the tissue engagement portion (2622) may be configured to pierce or penetrate through the tissue. In some variations, the geometry and size of each tissue engagement portion (2622) may be the same or different. For example, the tissue engagement portion (2622) may comprise a sharp point or a blunt, atraumatic end. In some variations, the tissue engagement portion (2622) may comprise one or more secondary structures (e.g., serrations) to prevent tissue from sliding down the projection (2620). In some variations, the tissue engagement portion (2622) may be substantially parallel to a longitudinal axis of the base (2620). In some variations, a length of the projection (2620) may be between about 0.1 mm and about 2 cm. For example, the projection (2620) may comprise a length of between about 1.25 mm and about 1.75 mm, and about 1.5 mm. In some variations, a length of the tissue engagement portion (2622) may be between about 1.0 mm and about 1.5 mm, including all ranges and sub-values in-between.

In some variations, the projections (2620) may be generally linear, but may comprise one or more bends. For example, a first portion (2624) of the projection (2620) may be configured to extend substantially perpendicularly to a longitudinal axis of the base (2620). In some variations, the projections may comprise one or more curved or angulated portions between the first portion (2624) and second portion (2622). In some variations, tissue may be configured to engage one or more portions of the projection (2620).

In some variations, a first portion (2624) of a projection (2622) may be angled between about 60 degrees and about 120 degrees relative to the longitudinal axis of the base (2610), including all values and sub-ranges in-between. For example, the projection (2620) may comprise an angle of between about 80 degrees and about 100 degrees relative to the longitudinal axis of the base (2610). As shown in FIG. 26A, the first portion (2624) may be substantially perpendicular to the longitudinal axis of the base (2610). Each first portion (2624) of the projection (2620) may have the same angle or a different angle relative to the longitudinal axis. In some variations, a second portion (2622) of a projection (2620) may be angled up to about 30 degrees relative to the longitudinal axis of the base (2610). For example, as shown in FIG. 26A, the second portion (2622) may be substantially parallel to the longitudinal axis of the base (2610).

In some variations, the projection (2620) may be configured to engage a predetermined length and/or volume of tissue. For example, the second portion (2622) may engage and pierce the tissue while the first portion (2624) may engage and secure the tissue to the barb (2600). The second portion (2622) may be configured to pierce through tissue such that the layers of an interatrial septum (e.g., left and right atrium layers) are held together to reduce tissue separation and/or tissue shearing. For example, the projection (2620) may be configured to penetrate and staple the various layers of the septum together to reduce relative shearing of septal tissue layers during translation, thereby reducing chamfering of the anastomosis to be formed. The first portion (2624) may further be configured as a barrier (e.g., backstop, wall) against additional tissue engagement (e.g., advancement, penetration), thereby reducing tissue tearing. A predetermined volume of tissue may be captured by the projections (2620) as the barb is withdrawn into a lumen of the electrode.

In some variations, a barb may comprise between about 3 projections and about 12 projections, including all values and sub-ranges in-between. For example, a barb may comprise between about 3 projections and about 7 projections. In some variations, a plurality of tissue engagement portions (2622) may extend from the same first portion (2624) that may collectively comprise, for example, a set of concentric rings. In some variations, the set of projections may be staggered. Tissue engaged to the barb (2600) may form a generally conical or cylindrical tent-like shape. In some variations, the tissue engagement portions (2622) may extend along a majority of a length of the projection (2620). In some variations, the base (2610) may comprise a diameter less than a diameter of an electrode.

In some variations, the barb may be configured to transition from a compressed configuration to an expanded configuration. For example, the barb may be in a compressed configuration when disposed within a lumen of an electrode. The barb may transition to an expanded configuration when the second catheter is advanced relative to the first catheter such that the barb is advanced out of the lumen of the electrode, thereby allowing the barb engage a large volume of tissue.

Figure 29A:
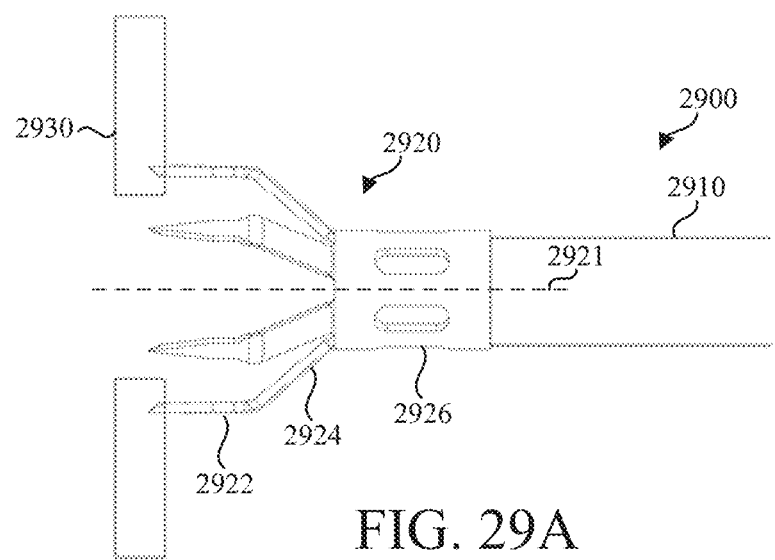
FIGS. 29A, 29B, and 29C are side views of a barb of an ablation device in an endocardial space.
Figure 29B:
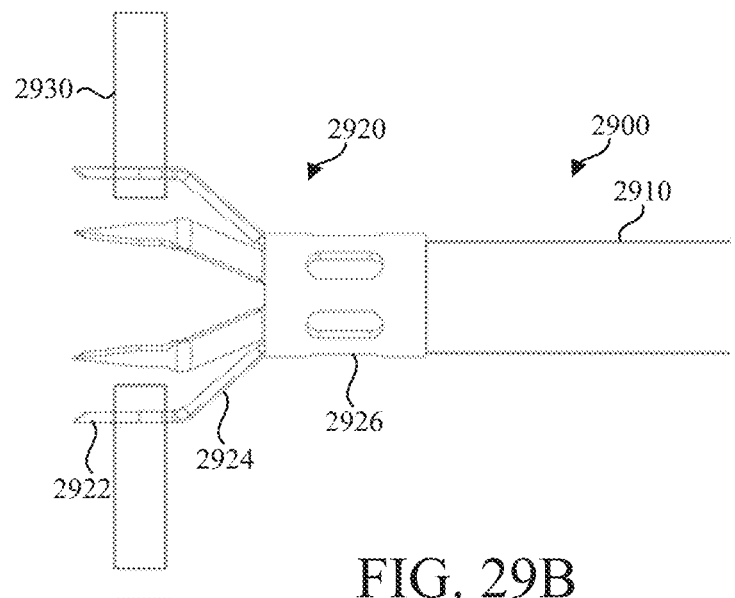
Figure 29C:
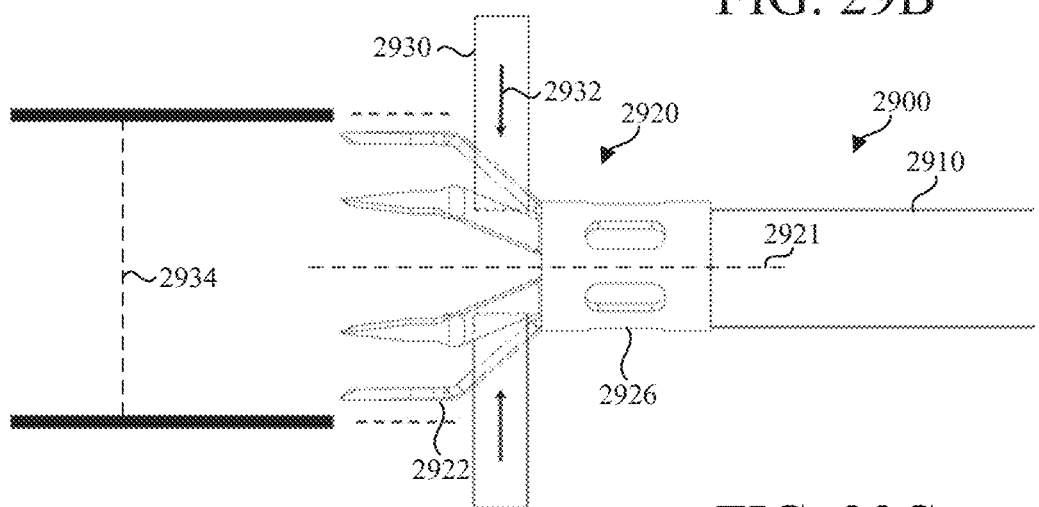

In some variations, a barb may be configured to engage tissue for cutting by rolling the barb (2920) by a predetermined angle. FIGS. 29A, 29B, and 29C are side views of a barb (2920) of an ablation device (2900) in an endocardial space. The ablation device (2900) may comprise a catheter (2910) (e.g., distal tip, dilator) and a barb (2920). The barb (2920) may comprise a base (2926) and one or more projections (e.g., prongs, tines) comprising a second portion (e.g., tissue engagement portion) (2922) (e.g., tip, point) and a first portion (2924).

In some variations, the second portion (2922) (e.g., tissue engagement portion) may be configured to engage tissue (2930) while not tearing the tissue to prevent a loss of tissue integrity. In some variations, the second portion (2922) may be configured to pierce or penetrate through the tissue. FIG. 29A depicts initial penetration of the tissue (2930) by the second portion (2922). As the barb (2920) is advanced towards the tissue (2930), FIG. 29B depicts penetration of the second portion (2922) through the entire thickness of the tissue (2930) (e.g., interatrial septum).

In some variations, a size (e.g., diameter) of the tissue (2930) to be cut may be controlled by rolling (e.g., twisting) the barb (2920) about a longitudinal axis (2921) of its base (2926). For example, rolling the barb (2920) after engagement with tissue (2930) (FIG. 29B) may increase an amount of tissue (2930) engaged to the barb (2920) to be cut. As the barb is rolled, tissue (2930) may be drawn toward (e.g., compressed) (2932) the longitudinal axis (2921) by the arrows (2932), as shown in FIG. 29C. This may enable a diameter (2934) of the tissue (2930) to be cut to be greater than a diameter of the barb (2920). In some variations, twisting the barb may increase a diameter of the tissue to be up to about 5 mm, up to about 3 mm, and up to about 1 mm, including all ranges and sub-values in-between.

In some variations, the barb (2920) may be configured to roll up to about 30 degrees, up to about 45 degrees, up to about 60 degrees, up to about 90 degrees, up to about 180 degrees, up to about 270 degrees, up to about 360 degrees, up to about 720 degrees, up to about 1,080 degrees, between about 90 degrees and about 720 degrees, and between about 180 degrees and about 360 degrees, including all ranges and sub-values in-between.

In some variations, a handle of the device may be configured to control rotation of the barb (2920) and/or catheter (2910), and therefore enable control of a size of the tissue (2930) to be cut. In some variations, a proximal portion of an ablation device (e.g., first catheter) may be fixed relative to a rotating distal portion of the ablation device (e.g., barb (2920) and catheter (2910)).

In some variations, the first portion (2924) may be angled relative to the second portion (2922) in a similar manner as described in detail herein with respect to FIGS. 26A-26C. In some variations, the projection may comprise a bend where the first portion (2924) is at an acute angle relative to the second portion (2922). For example, as shown in FIGS. 29A-29C, the first portion (1924) is at an acute angle relative to a longitudinal axis (2921) of the base (2926). The base (2926) may be generally cylindrical and configured to couple to a proximal portion of a catheter (2910) (e.g., second catheter, distal catheter). For example, the base (2926) may be proximal to a dilator (not shown in FIGS. 29A-29C).

Figure 30A:
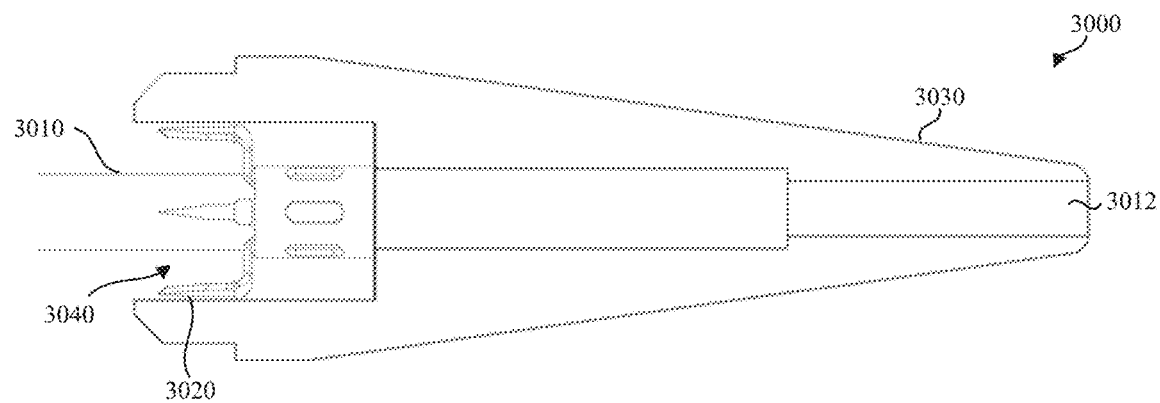
FIGS. 30A and 30B are cross-sectional side views of a barb and catheter of an ablation device.
Figure 30B:
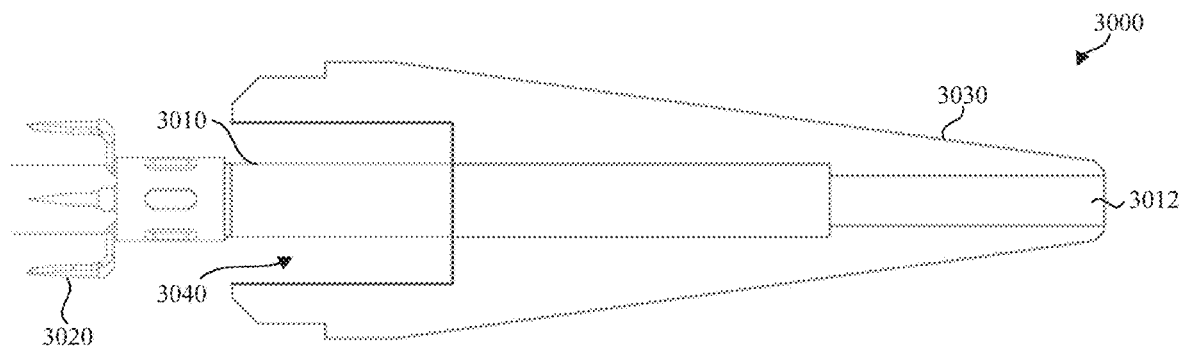

In some variations, a barb may be configured to translate relative to the dilator (3030) to transition between a first configuration (e.g., recessed configuration) and a second configuration (e.g., extended configuration). FIGS. 30A and 30B, are cross-sectional side views of a distal portion of an ablation device (3000) comprising a catheter (3010) (e.g., second catheter), barb (3020), and distal tip (3030) (e.g., dilator). In some variations, the catheter (3010) and/or dilator (3030) may comprise one or more lumens (3012). For example, a guidewire (not shown) may be configured to be slidably disposed within the lumen (3012) and/or other catheter (3010). In some variations, the dilator (3030) may define a recess (3040) configured to hold (e.g., surround, enclose) the barb (3020). That is, the barb (3020) may be configured to be seated within the recess (3040). For example, a length of the recess (3040) may be at least equal to a length of the barb (3020) such that the entire barb (3020) may fit within the recess (3040). In some variations, the recess (3040) may be defined within a proximal end of the dilator (3030).

FIG. 30A illustrates the ablation device (3000) in a first configuration where the barb (3020) is arranged inside the recess (3040) of the dilator (3030). In the first configuration, the barb (3020) may be protected from contact with tissue which may be useful while the catheter (3010) and dilator (3030) are advanced through the body of a patient. FIG. 30B illustrates the ablation device (3000) in a second configuration where the barb (3020) is arranged outside the recess (3040) of the dilator (3030). In the second configuration, the barb (3020) may be configured to engage tissue as described in detail herein.

In some variations, a handle of the device may be configured to control translation of the barb (3020) and/or catheter (3010) relative to the dilator (3030), and therefore enable control of a size of the tissue to be cut. For example, a barb (3020) extended from the dilator (3030) may tent engaged tissue and increase the diameter of tissue to be cut by the ablation device (3000). In some variations, a position of a proximal portion of an ablation device (e.g., catheter comprising an electrode) and dilator (3030) may be fixed relative to the translatable barb (3020). For example, the barb (3020) may transition from the first configuration to the second configuration after the dilator (3030) has advanced through the interatrial septum.

In some variations, the barb may be formed to have enough strength to hold tissue without breaking. The barb may comprise one or more of stainless steel, nitinol, platinum, polyvinyl chloride (PVC), polyethylene (PE), cross-linked polyethylene, polyolefins, polyolefin copolymer (POC), polyethylene terephthalate (PET), polyester, nylon, polymer blends, polyester, polyimide, polyamides, polyurethane, silicone, polydimethylsiloxane (PDMS), PEBAX, combinations thereof, and the like.

Figure 40A:
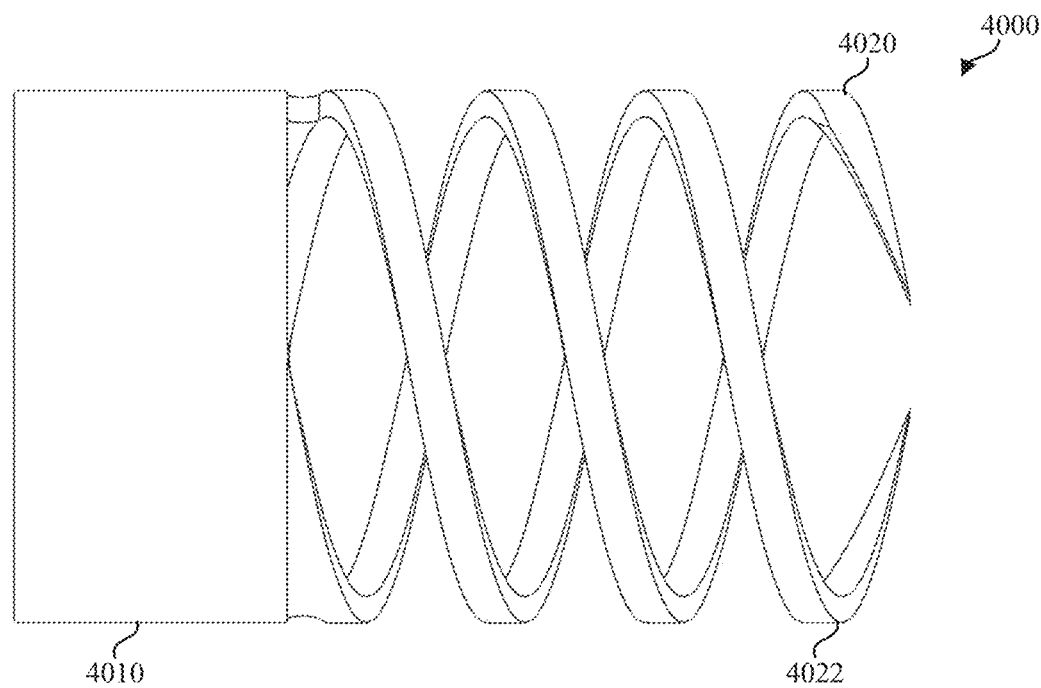
FIG. 40A is a side view of an illustrative variation of a barb of an ablation device.
Figure 40B:
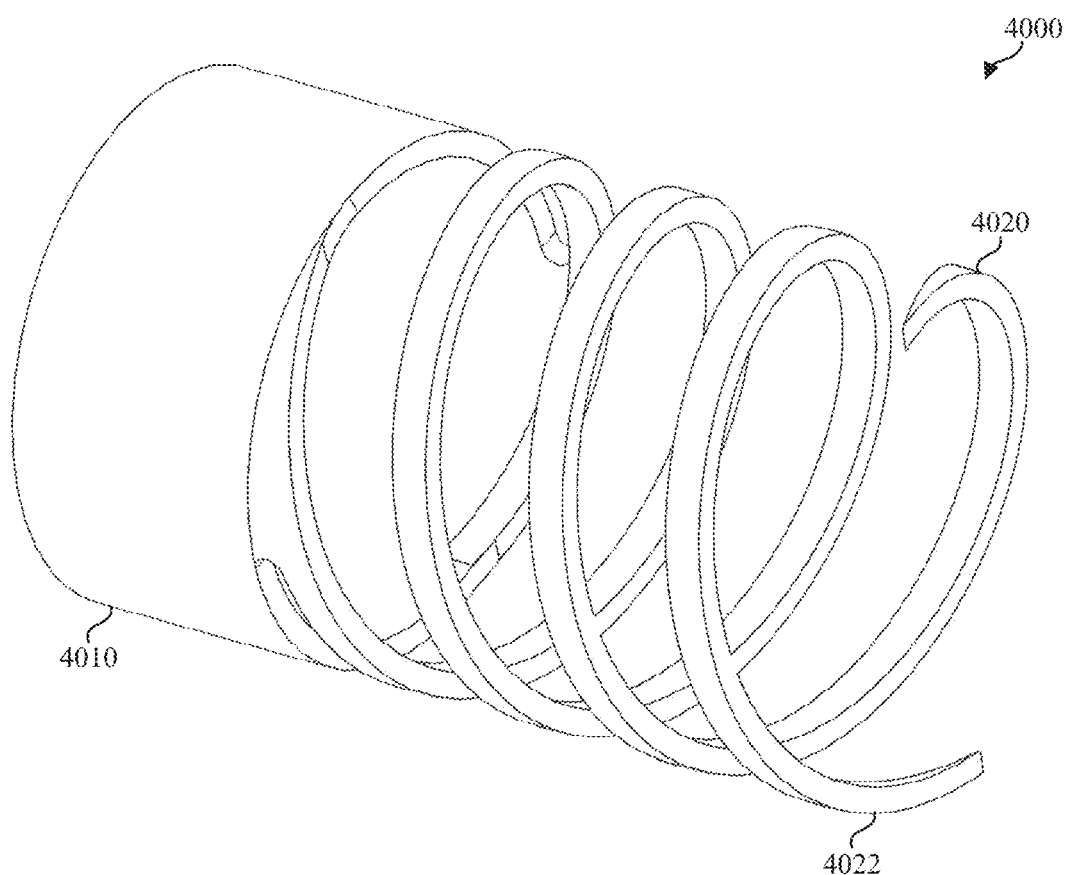
FIG. 40B is a perspective view of an illustrative variation of a barb of an ablation device.

Additionally or alternatively, a barb may comprise one or more of a spiral, helical, corkscrew, and coil shape. FIG. 40A is a side view and FIG. 40B is a perspective view of a barb (4000) comprising a double-helix shape. The barb (4000) may comprise a base (4010), a first projection (4020), and a second projection (4022). The projections (4020, 4022) may each comprise a distal tip configured to pierce (e.g., penetrate) tissue. For example, the barb (4000) may be configured to rotate (e.g., corkscrew) into tissue. The projections (4020, 4022) may have the same or different shape and dimensions. In some variations, a catheter may be configured to rotate about a longitudinal axis to enable the barb (4000) to twist and engage tissue. As described in detail herein with respect to FIGS. 29A-29C, rotation of the barb may enable control of a diameter of tissue to be cut.

In some variations, a barb may comprise set of concentric rings along a length of a second catheter. For example, the barb may comprise a set of rings with a thin radial edge of each ring configured to engage tissue. The tented tissue engaged by the barb may be configured to form a generally conical or cylindrical shape. In some variations, at least a portion of the barb may comprise a textured or roughened surface configured to aid tissue engagement. In other variations, the barb may comprise a stepped structure. In some variations, the projection may comprise a mesh comprised of one or more struts. For example, the mesh may be disposed radially about the second catheter and splay outward.

Visualization Features

In some variations, the ablation devices and systems described here may comprise one or more visualization features for indirectly visualizing the ablation device. For example, visualization features and techniques may facilitate one or more of imaging, positioning, alignment, and operation of the ablation device in a body cavity. For example, indirect visualization techniques may include, but are not limited to ultrasound, fluoroscopy, and X-ray. Fluoroscopically visualized elements, as described in detail herein, enable alignment of catheters to tissue and each other.

In some variations, a visualization feature may be visualized using a technique such as ultrasound and fluoroscopy during operation of an ablation system. For example, a contrast agent may be used to visualize one or more components of an ablation device and their positions and/or orientations relative to tissue such as an interatrial septum. In some variations, a contrast agent (e.g., contrast medium) may comprise one or more of agitated saline and microbubbles (e.g., $CO_2$). In particular, microbubbles may be used in conjunction with sonographic (e.g., ultrasound) examination such as an echocardiogram. For example, microbubbles may oscillate and vibrate when ultrasonic energy is received and reflect ultrasound waves. Microbubbles introduced into a body cavity may enhance a contrast of an image at the interface between the tissue, blood, and ablation device.

In some variations, microbubbles may comprise a shell and a gas core. For example, a microbubble shell may comprise one or more of albumin, galactose, proteins, lipids, polymers, combinations thereof, and the like. A microbubble gas core may comprise one or more of air, nitrogen, perfluorocarbons, combinations thereof, and the like.

Generally, microbubbles may comprise a diameter between about 1 μm and about 1 mm, about 1 μm and about 5 μm, about 1 μm and about 10 μm, about 10 ηm and about 50 μm, about 50 μm and about 0.1 mm, about 0.1 mm and about 0.5 mm, and about 0.5 mm and about 1 mm, including all ranges and sub-values in-between.

Figure 31A:
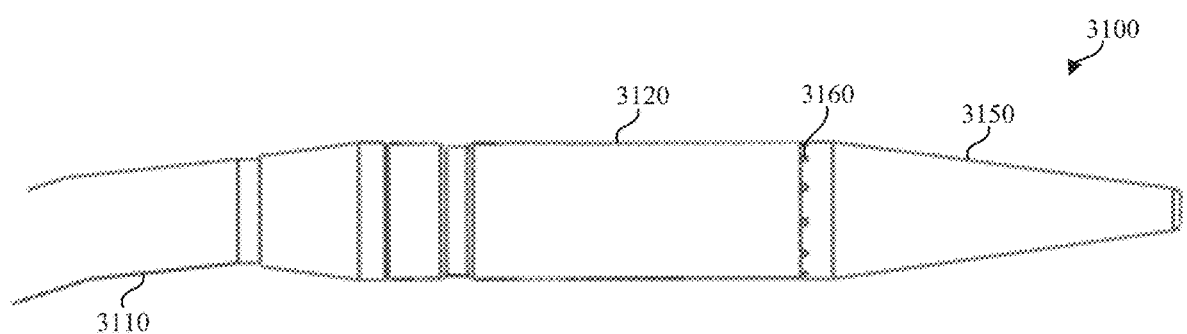
FIG. 31A is a side view of an illustrative variation of an ablation device.

In some variations, the ablation devices described herein may be configured to output microbubbles for indirect visualization. FIG. 31A is a side view of an ablation device (3100) comprising a first catheter (3110), electrode (3120), and dilator (3150). In some variations, the dilator (3150) may comprise one or more fluid ports (3160) configured to output a microbubble. That is, microbubbles may be introduced (e.g., injected) into a body cavity when the ablation device (3100) is in a closed configuration as described in detail herein. FIG. 31A illustrates a plurality of fluid ports (3160) arranged radially about a proximal circumference of the dilator (3150). In some variations, microbubbles may be delivered within a lumen of electrode (3120) and be configured to flow out of one or more of the fluid port (3160) to an exterior of the ablation device (3100).

Figure 42A:
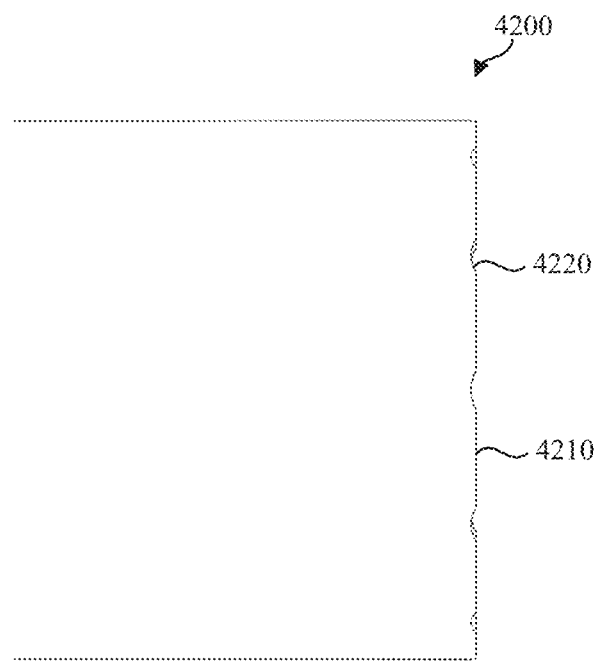
FIGS. 42A and 42B are schematic side and perspective views of an illustrative variation of an electrode of an ablation device.
Figure 42B:
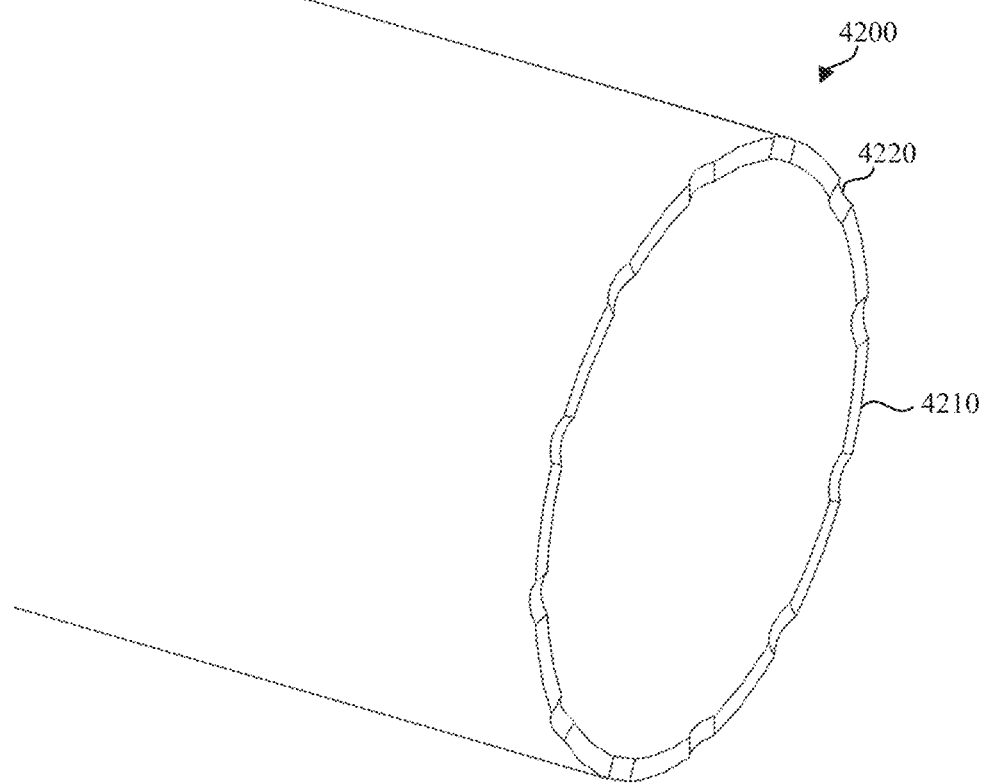

Additionally or alternatively, the electrode (3120) may comprise one or more fluid ports, as discussed in more detail with respect to FIGS. 42A and 42B. For example, a distal end of the electrode may comprise one or more apertures (e.g., openings, slits, channels, recesses, ridges) configured to output a microbubble. In some variations, any portion of the electrode (3120) may comprise a fluid port (3160).

Figure 31B:
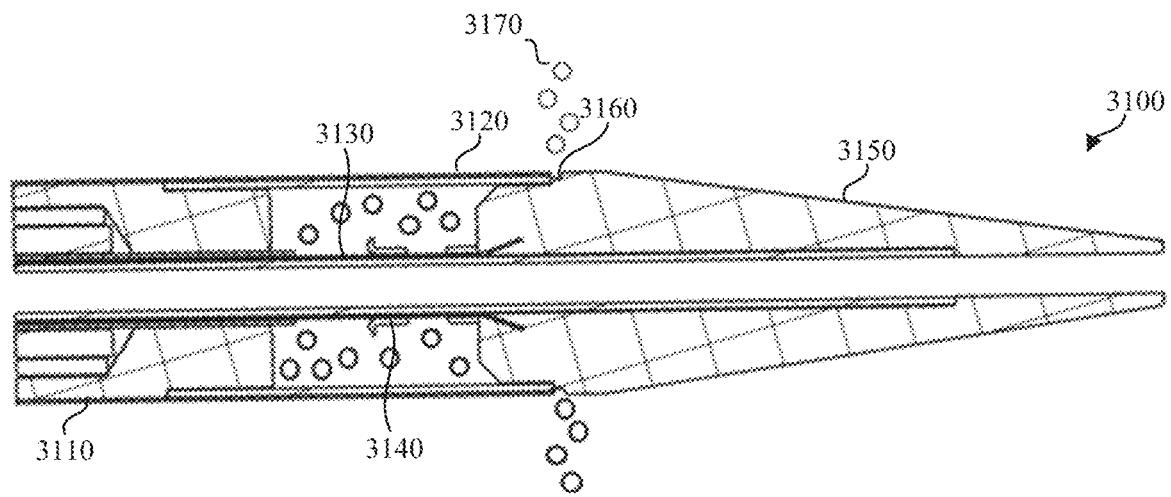
FIG. 31B is a cross-sectional side view of an illustrative variation of an ablation device.

FIG. 31B is a cross-sectional side view of the ablation device (3100) comprising the first catheter (3110), electrode (3120), second catheter (3130), barb (3140), and dilator (3150). The ablation device (3100) in the closed configuration shown in FIG. 31B depicts the barb (3140), microbubbles (3170), and proximal end of the dilator (3150) enclosed within a lumen of the electrode (3120). One or more of the first catheter (3110) and second catheter (3130) may be configured to output a contrast agent (3170) (e.g., microbubbles) from a respective contrast agent lumen (not shown in FIG. 31B). For example, the contrast agent (3170) may be output into a lumen of the electrode (3120) and then out of the ablation device (3100) via fluid port (3160).

Figure 31C:
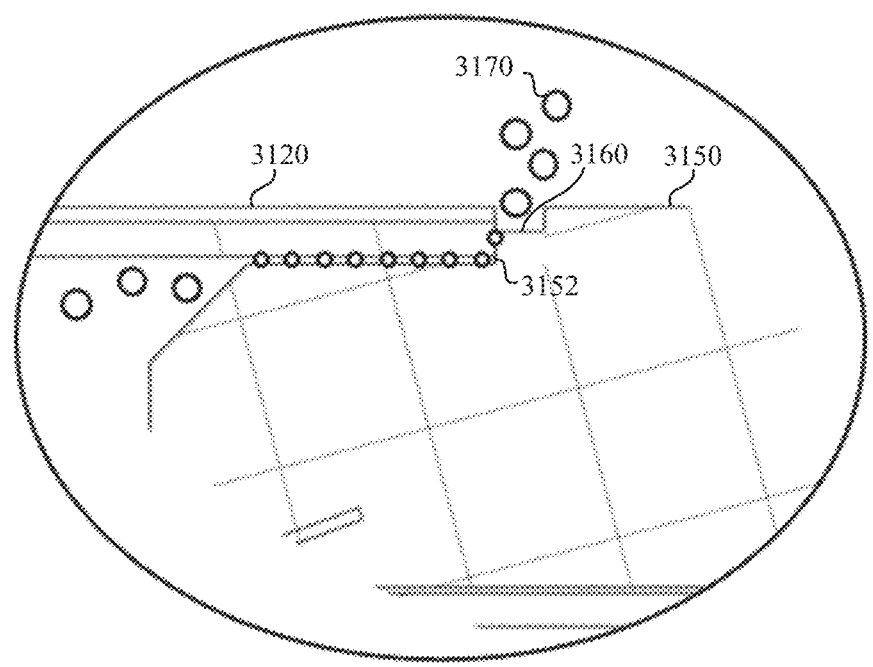
FIG. 31C is a detailed cross-sectional side view of the ablation device shown in FIG. 31B.

In some variations, a contrast agent (e.g., microbubbles) may be introduced (e.g., injected) into a lumen of the electrode (3120) and then into a body cavity when the ablation device (3100) is in a closed configuration. FIG. 31C is a detailed cross-sectional side view of the ablation device (3100). In some variations, the dilator (3150) may comprise a mating surface (3152) configured to engage a distal end of the electrode (3120) in a closed configuration in a similar manner as described with respect to, for example, FIGS. 6A-6C and 9A-9B. As shown in FIG. 31C, a contrast agent (3170) may be configured to flow between an inner diameter of the electrode (3120) and an outer diameter of a proximal end of the dilator (3150) and out of the fluid port (3160). Thus, the contrast agent (3170) may be output from the ablation device (3100) through the fluid port (3160). If the mating surface is not compressed against the electrode (3120) (e.g., withdrawn by an operator at a handle that applies a preload force), the ablation device (3100) may be configured to output microbubbles from the fluid port (3160). Thus, one or more fluid ports (3160) of the dilator (3150) may be configured to output a contrast agent (3170) received from a lumen of the electrode (3120).

Figure 31D:
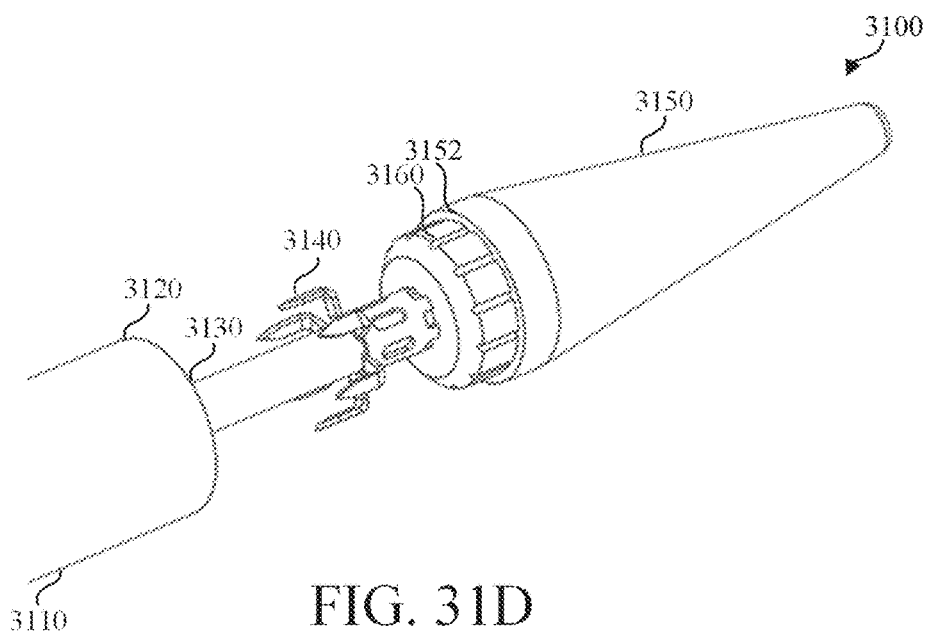
FIGS. 31D, 31E, and 31F are perspective views of illustrative variations of a distal portion of an ablation device.
Figure 31E:
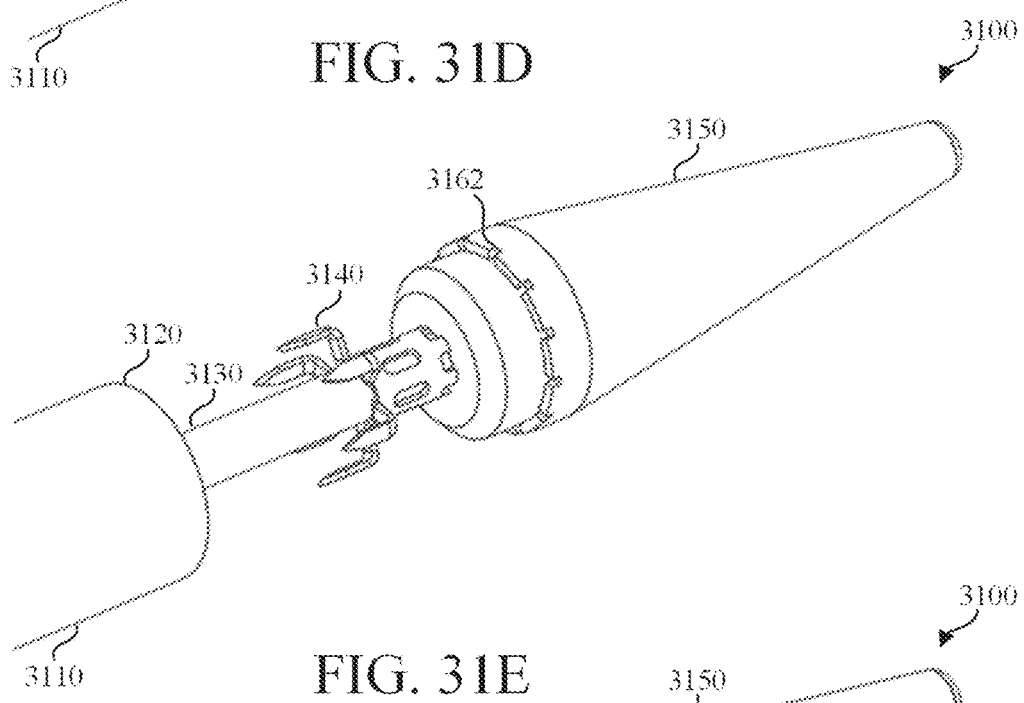
Figure 31F:
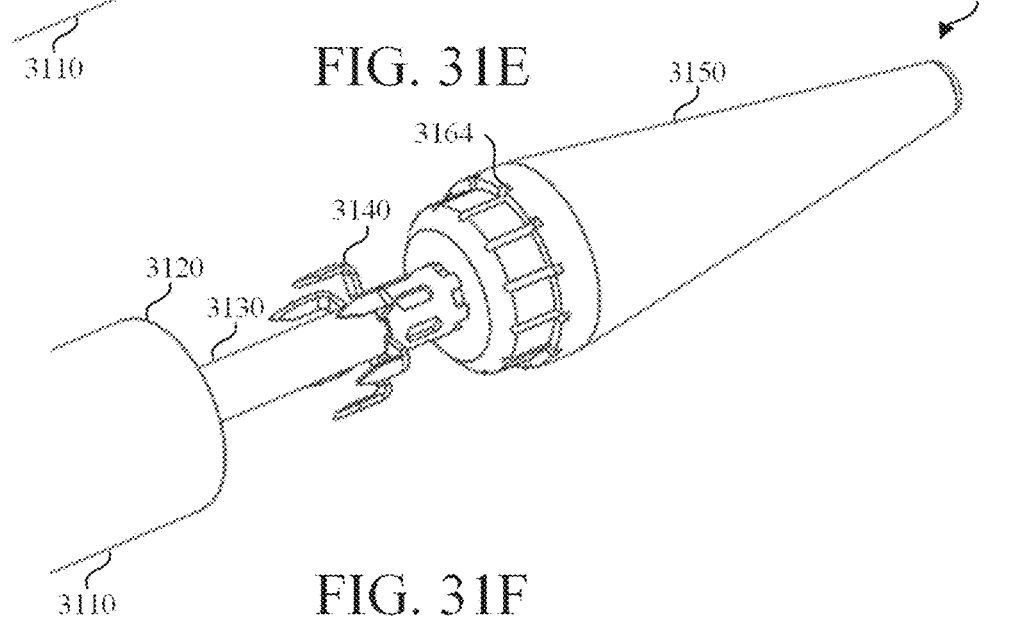

FIGS. 31D, 31E, and 31F are perspective views of a distal portion of an ablation device (3100) comprising the first catheter (3110), electrode (3120), second catheter (3130), barb (3140), and dilator (3150). The ablation device (3100) is disposed in an open configuration to aid illustration of various fluid port configurations (3160, 3162, 3164) of the dilator (3150). The fluid ports (3160, 3162, 3164) may be configured to enable a contrast agent (e.g., microbubbles) to flow from a lumen of the electrode (3120) to an exterior of the ablation device (3100). Without fluid ports (3160, 3162, 3164), a contrast agent may be sealed within the lumen of the electrode (3120) while the ablation device (3100) is in the closed configuration, thus requiring the electrode (3120) to be separated from the dilator (3150). By contrast, the fluid ports (3160) enable contrast agent flow into a body cavity from the closed configuration.

In some variations, the fluid port (3160) may comprise a shape including, but not limited to, an aperture, opening, slit, channel, recess, ridge, hole, combinations thereof, and the like. FIG. 31D illustrates a fluid port (3160) configuration comprising a plurality of lengthwise channels disposed along a proximal portion of the dilator (3150) proximal to the mating surface (3152) of the dilator (3150). FIG. 31E illustrates a fluid port (3162) configuration comprising a plurality of recesses disposed within the mating surface (3152) of the dilator (3150). FIG. 31F illustrates a fluid port (3164) configuration comprising a combination of the lengthwise channels of FIG. 31D and recesses of FIG. 31E. In some variations, the ablation device (3100) may comprise one or more fluid ports (3160). For example, the ablation device (3100) may comprise up to about 3 fluid ports, up to about 5 fluid ports, up to about 7 fluid ports, up to about 10 fluid ports, up to about 20 fluid ports, up to about 50 fluid ports, up to about 75 fluid ports, and up to about 100 fluid ports, including all values and sub-ranges in-between.

As shown in FIGS. 42A and 42B, an electrode (4200) may comprise one or more fluid ports (4220). For example, a distal end (4210) of the electrode (4200) may comprise one or more fluid ports (4220) (e.g., apertures, openings, slits, channels, recesses, ridges, vents) configured to output a fluid (e.g., contrast agent, contrast medium, microbubble). For example, the fluid ports (4220) may comprise a diameter at least as large as a diameter of a microbubble to allow microbubbles to pass therethrough. In some variations, a fluid port of an electrode (4200) may be aligned or offset from a fluid port of a dilator. In some variations, the fluid ports described herein may be formed via laser cutting. In some variations, any portion of the electrode (4200) may comprise a fluid port (4220).

Figure 33A:
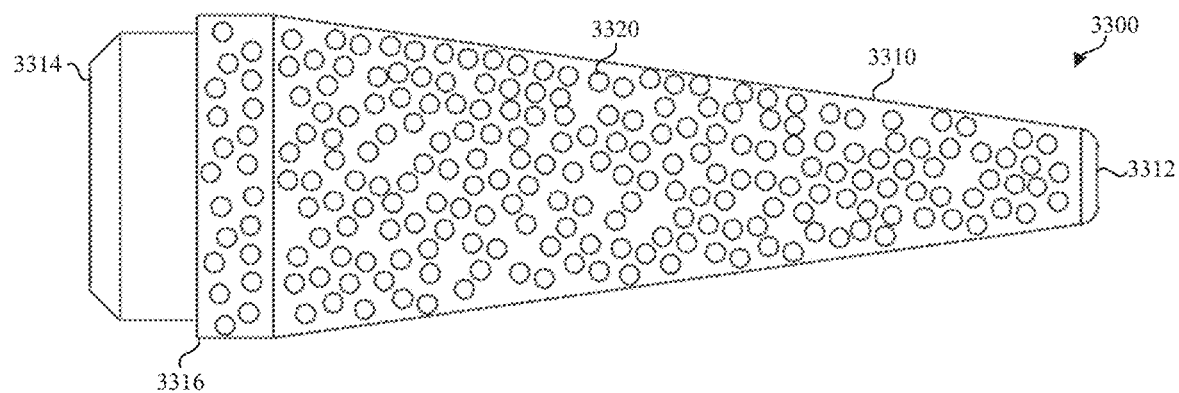
FIG. 33A is a side view of an illustrative variation of a catheter of an ablation device.
Figure 33B:
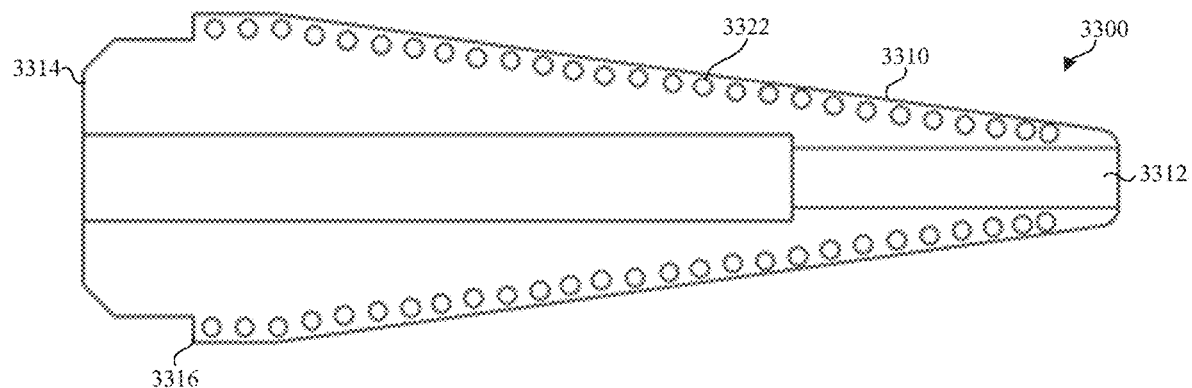
FIG. 33B is a cross-sectional side view of an illustrative variation of a catheter of an ablation device.

FIG. 33A is a side view and FIG. 33B is a cross-sectional side view of a distal portion (3310) (e.g., dilator, distal tip) of an ablation device (3300). In some variations, a dilator (3310) may comprise a lumen (3312), a proximal end (3314), a mating surface (3316), and one or more visualization features (3320, 3222). In some variations, a visualization feature (3320, 3222) may correspond to an echogenic region.

In some variations, the echogenic region may comprise one or more microspheres, recesses, protrusions, channels, grooves, scratches, edges, indentations, blind holes, hills-and-valleys, undercuts, combinations thereof, and the like. For example, one or more microspheres, recesses, or protrusions may comprise a diameter of between about 5 µm and about 100 µm. In some variations, the microspheres may comprise a gas core. The microspheres may comprise glass.

In some variations, the echogenic region may comprise one or more portions of the dilator. For example, FIGS. 33A and 33B illustrate a proximal portion (3314) without visualization features (3320, 3222). In some variations, the echogenic region may comprise a plurality of texture patterns. For example, a first texture pattern may be arranged along a distal end of the dilator (3310) and a second texture pattern may be arranged along a proximal end of the dilator (3310). This may aid identification of different portions of the dilator (3310). In some variations, a texture pattern may comprise a shape including, but not limited to circumferential, radial, cross-hatched, random, linear, curved, spiral, ovoid, ellipsoid, sinusoidal, polygonal, non-linear, combinations thereof, and the like.

In some variations, the echogenic region may comprise a visualization feature (e.g., recess, protrusion, etc.) density of between about 5% and about 50%, about 10% and about 40%, about 20% and about 30%, about 5% and about 10%, about 10% and about 20%, about 30% and about 40%, and about 40% and about 50%, including all values and subranges in-between.

In some variations, an echogenic region may be on and/or below a surface of the dilator (3310). For example, FIG. 33A depicts a schematic (e.g., not to scale) representation of a plurality of microspheres formed on top of a surface of the dilator (3310). In some variations, the echogenic region may comprise one or more surface textures or patterns on the surface of the dilator (3310). In some variations, a surface texture of an echogenic region may be generated using one or more of grit blasting on an injection mold, laser engraving, abrasive finishing, grooving, etching, deposition, combinations thereof, and the like.

FIG. 33B depicts a schematic representation of a plurality of microspheres formed beneath a surface of the dilator (3310). In some variations, heat treatment (e.g., vesiculation) may be applied to the dilator (3310) to generate one or more microspheres beneath the surface of the dilator (3310). For example, heating the dilator (3310) above a melting temperature of a material (e.g., plastic) of the dilator (3310) may induce microbubble formation of void inclusions under a surface of the dilator through vaporization of volatile compounds. In some variations, a dilator may be formed using microspheres such as glass beads arranged beneath a surface of the dilator (3310). In some variations, a high temperature heat source (e.g., flame, laser) may treat a surface of the dilator (3310) in short bursts (e.g., sub-second) that may melt a surface but not through an entire thickness of the dilator (3310). Additionally or alternatively, a glass microsphere may be compounded into a base resin material that is injection molded to form the dilator (3310).

Additionally or alternatively, fluoroscopy is a technique for real-time X-ray imaging and may be used to guide catheter insertion and movement through blood vessels. Generally, in fluoroscopy, an X-ray beam is emitted from a fluoroscope through an area of interest in a body. Objects to be visualized (e.g., ablation device) may be imaged using an image intensifier. A user viewing the real-time images shown by the image intensifier may then determine the orientation and alignment of the catheters relative to each other.

In some variations, one or more of the first and second catheters may comprise a metal-based radiopaque marker comprising one or more of a ring, band, and ink (e.g. platinum, platinum-iridium, gold, nitinol, palladium) configured to permit fluoroscopic visualization.

The ablation devices described herein may comprise any radiopaque metal, such as tungsten, platinum iridium, stainless steel, titanium, as well as a tungsten filled polymer, zirconia ceramic, or any suitable radiopaque material. A visualization feature may be located at any suitable position on or within the catheter (e.g., one or more exterior surfaces of the device, inside of the catheter, or the like). In some variations, one or more portions of the ablation device may be made from a radiopaque material, or visualization feature may be attached to the device by any suitable method, for example, by mechanical attachment (e.g., embedded in a portion of the catheter, circumferential circumscription, or the like), adhesive bonding, welding, soldering, combinations thereof or the like.

Sensor

In some variations, the ablation devices and systems described here may comprise one or more sensors. Generally, the sensors described here may be configured to receive and/or transmit a signal corresponding to one or more parameters. In some variations, the sensor may comprise one or more of a pressure sensor, temperature sensor, electrical sensor (e.g., impedance sensors, electrical voltage sensor for sensing signals such as electromyogram, electrocardiogram, and the like), magnetic sensor (e.g., RF coil), electromagnetic sensor (e.g., infrared photodiode, optical photodiode, RF antenna), force sensor (e.g., a strain gauge), flow or velocity sensor (e.g., hot wire anemometer, vortex flowmeter), acceleration sensor (e.g., accelerometer), chemical sensor (e.g., pH sensors, protein sensor, glucose sensor), oxygen sensor (e.g., pulse oximetry sensor, myocardial oxygen consumption sensor), audio sensor (e.g., a microphone to detect heart murmurs, auscultation), sensor for sensing other physiological parameters (e.g., sensors to sense motion of heart walls, heart rate, breathing rate, arrhythmia), a stimulator (e.g., for stimulation and/or pacing function), combinations thereof, and the like. In some variations, an impedance sensor may be configured to monitor impedance between the electrode and return electrode to confirm completion of tissue excision.

Guidewire

In some variations, a guidewire may be slidably disposed within an ablation device and configured to cross the interatrial septum (e.g., using a standard transseptal puncture technique). In some variations, first and second catheters of the ablation device may be translated along the guidewire relative to one another and/or the interatrial septum. For example, the guidewire may comprise one or more of stainless steel, nitinol, platinum, and other suitable, biocompatible materials.

Catheter

Generally, the catheters described here may be configured to deliver an electrode and barb to one or more heart chambers for cutting tissue such as an interatrial septum. In some variations, a catheter may comprise a shaft composed of a flexible polymeric material such as Teflon, Nylon, Pebax, combinations thereof, and the like. In some variations, the ablation device may comprise one or more steerable or deflectable catheters (e.g., unidirectional, bidirectional, 4-way, omnidirectional). In some variations, the first catheter may comprise one or more pull wires configured to steer or deflect a portion of the first catheter. In some variations, the first catheter may have a bend radius of between about 45 degrees and about 270 degrees. In some variations, the second catheter described herein define a lumen through which a guidewire may pass.

In some variations, the catheter may be woven and/or braided and composed of a material (e.g., nylon, stainless steel, polymer) configured for catheter pushability and flexibility. In some variations, a first catheter may comprise a predetermined curved shape configured to guide a second catheter towards the septum at a predetermined orientation and angle.

Figure 34A:
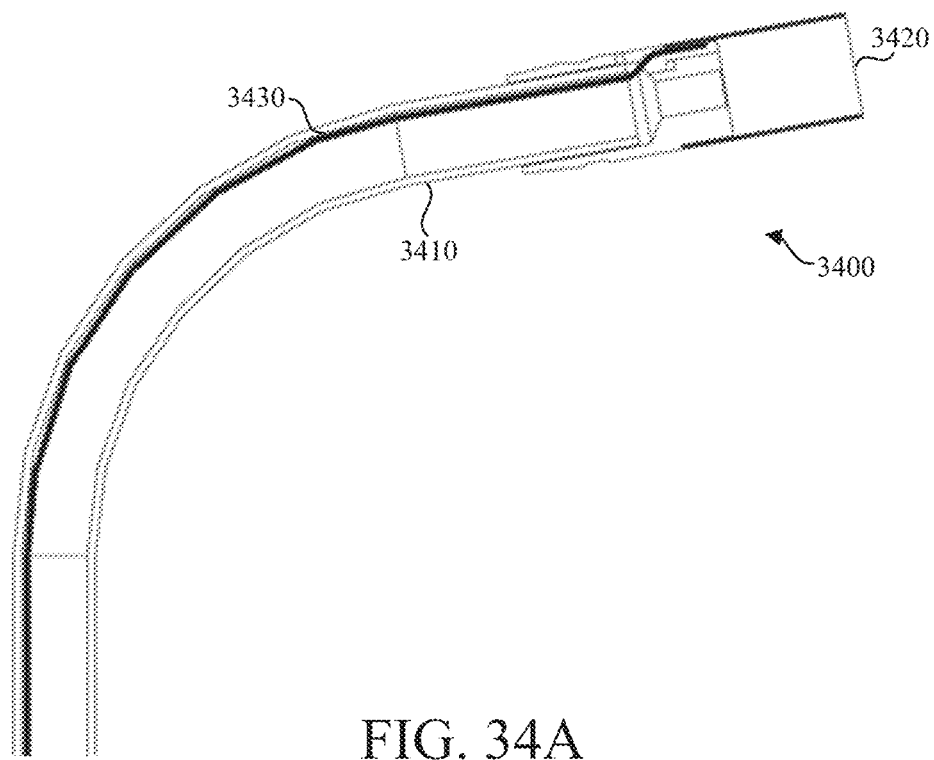
FIGS. 34A and 34B are cross-sectional plan views of a distal end of a catheter of an ablation device.
Figure 34B:
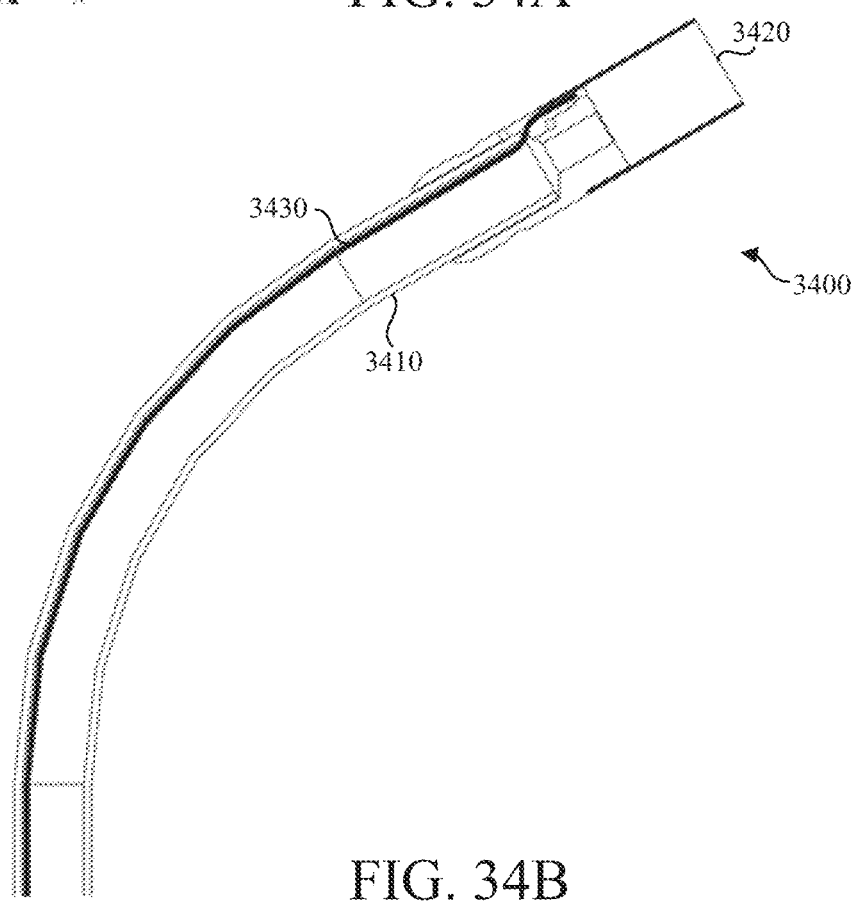

FIGS. 34A and 34B are cross-sectional side views of a distal end of a first catheter (3410) of an ablation device (3400). In some variations, a distal portion of the first catheter (3410) may comprise a predetermined bend (e.g., precurve tip), as shown in FIG. 34A. For example, the predetermined bend may allow a distal end of the first catheter (3410) to be oriented at a predetermined angle to tissue such as an interatrial septum. In some variations, the predetermined bend may comprise an angle between about 30 degrees and about 70 degrees.

In some variations, the distal portion of the first catheter (3410) may be positioned at a predetermined location and/or orientation (e.g., substantially perpendicular to a tissue wall) by deflecting (e.g., controlling a bend of) the first catheter (3410). In some variations, the first catheter actuator (3430) may be configured to deflect a distal portion of the first catheter (3410) while also electrically coupling the electrode (3430) to a signal generator (not shown). In this manner, the first catheter actuator (3430) may simultaneously function as a pull wire configured to steer the first catheter (3410) and deliver energy to the electrode (3420).

In some variations, the ablation device (3400) may comprise a first catheter (3410), an electrode (3420) coupled to a distal end of the first catheter (3410), and a first catheter actuator (3430) coupled to the electrode (3420). For example, the first catheter actuator (3430) may be electrically coupled to the electrode (3420). In some variations, the first catheter actuator (3430) may be coupled (e.g., affixed, welded, laser welded) to an inner surface of the electrode (3420). Therefore, pulling on the first catheter actuator (3430) may allow a predetermined amount of tension to be applied to a distal portion of the first catheter (3410). A first catheter actuator (3430) may have a longitudinal axis that is offset and parallel with respect to a central longitudinal axis (not shown) of the first catheter (3410). Pulling on the first catheter actuator (3430) may generate a bending moment between a central longitudinal axis of the first catheter (3410) and the radius to where the first catheter actuator (3430) is coupled to the electrode (3420).

The electrode (3420) may be configured to ablate tissue using electrical current passed from the signal generator through an electrical conductor (e.g., lead wire) of the first catheter actuator (3430). In some variations, the first catheter actuator (3430) may comprise a pull wire extending along a length of the first catheter (3410). A proximal end of the first catheter actuator (3430) may be configured to couple to an actuation mechanism. For example, a handle may comprise the actuation mechanism configured to steer the first catheter (3410) via the first catheter actuator (3430). That is, tension and/or compression may be applied to the first catheter actuator (3430) in order to deflect (e.g., change an angle) the distal portion of the first catheter (3410), as shown in FIG. 34B. Accordingly, a separate pull wire and lead wire is unnecessary such that the ablation device (3400) may be reduced in size and be less costly to manufacture.

Figure 34C:
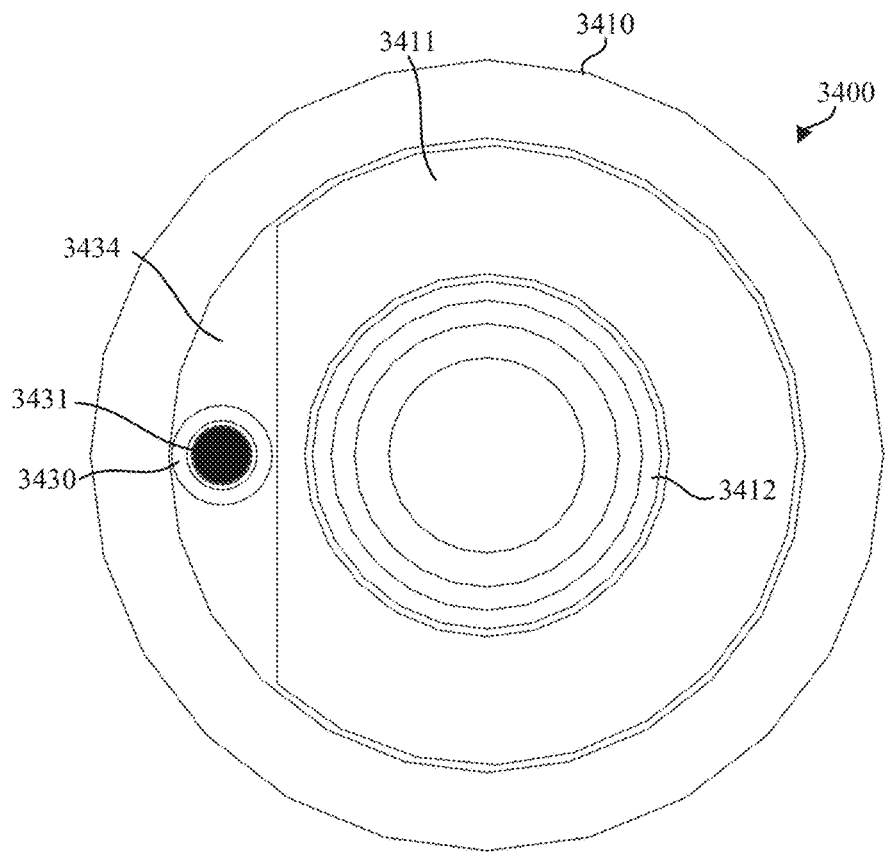
FIGS. 34C and 34D are cross-sectional side views of a catheter of an ablation device.
Figure 34D:
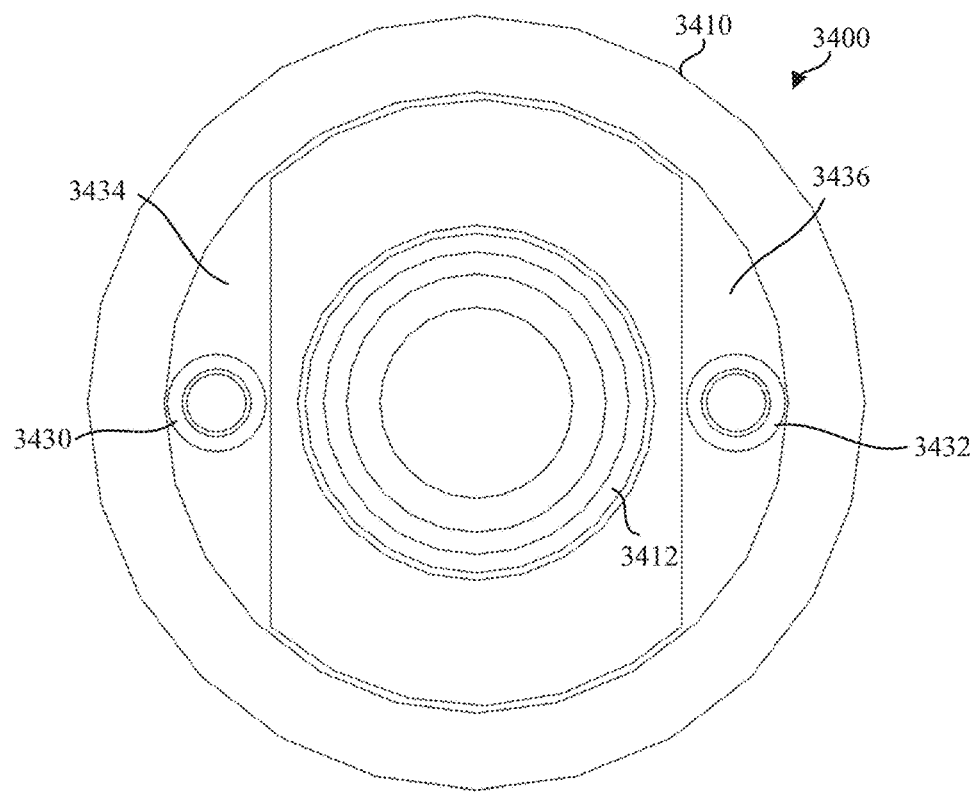

FIGS. 34C and 34D are cross-sectional side views of variations of the ablation device (3400). FIG. 34C illustrates an ablation device (3400) comprising a single first catheter actuator (3430) and FIG. 34D illustrates an ablation device (3400) comprising a pair of first catheter actuators (3430, 3432). Each first catheter actuator (3430, 3432) may be configured to electrically couple to an electrode for redundancy.

FIG. 34C depicts an ablation device (3400) comprising a first catheter (3410) defining a first catheter lumen (3412) and a first catheter actuator lumen (3434). In some variations, the first catheter actuator (3430) may comprise a lead wire (3431) comprising an insulator surrounding an electrode wire. In some variations, the insulator may be configured as a slidable channel. The insulator may comprise, for example, PTFE, PEEK, polyimide, combinations thereof, and the like. In some variations, the first catheter actuators (3430, 3432) may be coupled to an inner wall of the first catheter (3410) along a length of the first catheter (3410).

In some variations, a plurality of first catheter actuators may further aid steerability and enhance control of an ablation device. For example, the first catheter actuators may be actuated together to provide a push and pull action (e.g., one actuator configured to pull while another actuator pushes). FIG. 34D depicts an ablation device (3400) comprising a first catheter (3410) defining first catheter actuator lumens (3434, 3436) having respective first catheter actuators (3430, 3432). In some variations, the first catheter actuators (3430, 3432) may be disposed on opposite side of the first catheter (3410). In some variations, the first catheter actuator lumens (3434, 3436) may comprise a "D" shape.

In some variations, a first catheter actuator may be composed of stainless steel. In some variations, a first catheter (3410) may comprise a core (3411) (e.g., PTFE) configured to maintain an alignment and radial position of the first catheter actuator(s) (3430, 3432).

Dilator

Generally, the dilators described here may be configured to puncture tissue such as an interatrial septum to allow one or more portions of an ablation device to be advanced into a body cavity such as a left atrium of the heart. In some variations, a dilator may generally be configured to dilate tissue such as an interatrial septum. The dilator may be atraumatic in profile to minimize any inadvertent or unintended damage. The dilator may comprise a taper of between about 1 degree and about 45 degrees to facilitate device crossing of the septum to the left atrium. In some variations, the dilator may comprise a thermoplastic polymer, nylon, polyurethane, ABS, acetal, polycarbonate, PET, PEBA, PEEK, PTFE, silicone, PS, PEI, latex, sulphate, barium sulfate, a copolymer, combinations thereof, and the like. As described in more detail herein, a dilator may comprise one or more visualization features such as a fluid port and echogenic region.

In some variations, a dilator of an ablation device may be configured to aid a tissue compression and/or cutting process. As described herein, a distal end of an electrode may be configured to abut against a corresponding mating surface of a dilator. For example, a second catheter may be withdrawn with respect to a first catheter such that a mating surface applies a preload force to an electrode. Compression of the tissue between the electrode and mating surface (via the preload force) may reduce the thickness of the tissue to be cut such that a septum may be cut more quickly and with less energy. Furthermore, compressed tissue may hold (e.g., secure, lock) the tissue in place relative to the ablation device to ensure that only a predetermined portion of tissue is cut. In some variations, compression of the tissue while electrical energy is applied may fuse layers of tissue (e.g., left and right atrial septal layers) together during ablation, thereby reducing a surface area of exposed tissue along a perimeter of the anastomosis after tissue excision. Compression of tissue may also reduce a volume of tissue.

In some variations, the dilator may be configured to contact and electrically short the electrode when tissue is fully cut. This may halt the formation of cutting plasma and reduce excess energy delivery, heat, bubble formation, neurostimulation, and the like. For example, when an uninsulated distal end of an electrode is energized, cutting plasma may be generated to excise tissue compressed between the electrode and a mating surface of the dilator. However, once the tissue is cut and separated from the electrode, the electrode may be isolated from the conductive pathway of the body provided by the tissue, thereby extinguishing the cutting plasma. Thus, completion of tissue ablation may be performed mechanically without sensors and/or feedback control, thereby reducing complexity of an ablation procedure.

Figure 35A:
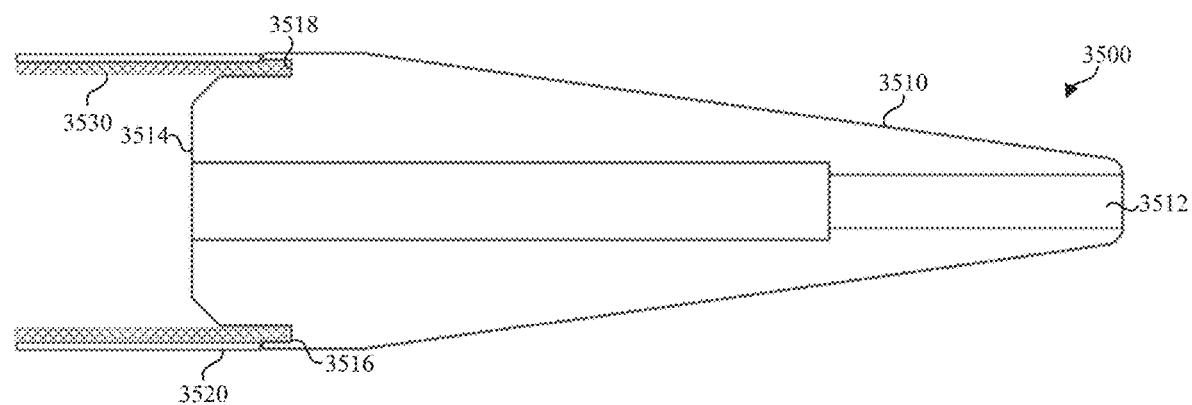
FIG. 35A is a cross-sectional side view of an illustrative variation of a distal portion of an ablation device.

FIG. 35A is a cross-sectional side view of a distal end of an ablation device (3500) comprising a dilator (3510), insulator (3520), and electrode (3530). The dilator (3510) may comprise a lumen (3512), a proximal end (3514), and a mating surface (3516) that defines a recess (3518) configured to receive a distal end of the electrode (3530). As shown in FIG. 35A, the distal end of the electrode (3530) is uninsulated. In some variations, the mating surface (3518) may comprise one or more of a non-conductive and/or thermally resistant portion. In some variations, the mating surface (3518) may be configured to withstand high temperatures generated during an ablation procedure. For example, the non-conductive portion may comprise one or more of a polymer (e.g., PEEK, polyimide), ceramic (e.g., zirconia), and aluminum oxide. Therefore, the electrode (3530) may be configured to electrically short when the electrode (3530) cuts tissue and engages the recess (3518) of the mating surface (3516).

Figure 35B:
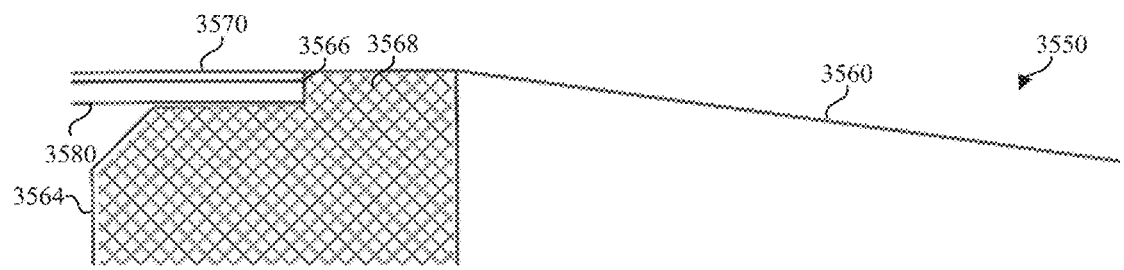
FIG. 35B is a detailed cross-sectional side view of another variation of a distal portion of an ablation device.

Additionally or alternatively, the mating surface may comprise a deformable material. FIG. 35B is a detailed cross-sectional side view of an ablation device (3550) including a dilator (3560), insulator (3570), and electrode (3580). The dilator (3560) may comprise a proximal end (3564) and a mating surface (3566). In some variations, the mating surface (3516) may be configured to be deformable (e.g., compressible). As the dilator (3560) is withdrawn towards the electrode (3580), tissue disposed between the electrode (3580) and mating surface (3566) may be compressed along with the mating surface itself.

Additionally or alternatively, the mating surface may comprise a conductive portion configured to focus RF energy (e.g., focused monopolar) in order to function as a dissipation element and/or enhance electric field lines and thus control stray excitation of tissue during cutting. For example, the conductive portion of the dilator may increase the surface area electrically coupled to the electrode in order to reduce a current density of the electrode below a threshold level sufficient to cut tissue. Thus, the electrode may be configured to contact the conductive mating surface after the tissue is cut. In some variations, the conductive portion of the mating surface may have a surface area between about 4 times and about 10 times the surface area of an exposed portion of the electrode (e.g., distal edge of the electrode).

In some variations, the dilator may comprise a length of between about 2 mm and about 2 cm. For example, the dilator may comprise a length of between about 5 mm and about 1 cm. In some variations, the dilator may comprise a taper of between about 5 degrees and about 20 degrees relative to a longitudinal axis of the dilator. In some variations, a distal end of the dilator may be atraumatic (e.g., rounded, blunted). As described herein, a barb may be coupled to the proximal end of the dilator.

Handle

Generally, the handles described here may be configured to allow an operator to grasp and control one or more of the position, orientation, and operation of an ablation device. In some variations, a handle may comprise an actuator to permit translation and/or rotation of the first and second catheters in addition to steering by an optional delivery catheter. Deployment of a barb, in some variations, may be performed by a deployment mechanism (e.g., screw/rotation mechanism, translation mechanism, slider). In some variations, the handle may be configured to limit the applied force that a user may administer to the advancement and retraction of the catheter shafts relative to each other. For example, the handle may be configured to apply energy to the electrode to ablate tissue and/or control one or more sensors. In some variations, the handle may be coupled between a signal generator and an ablation device.

Figure 39A:
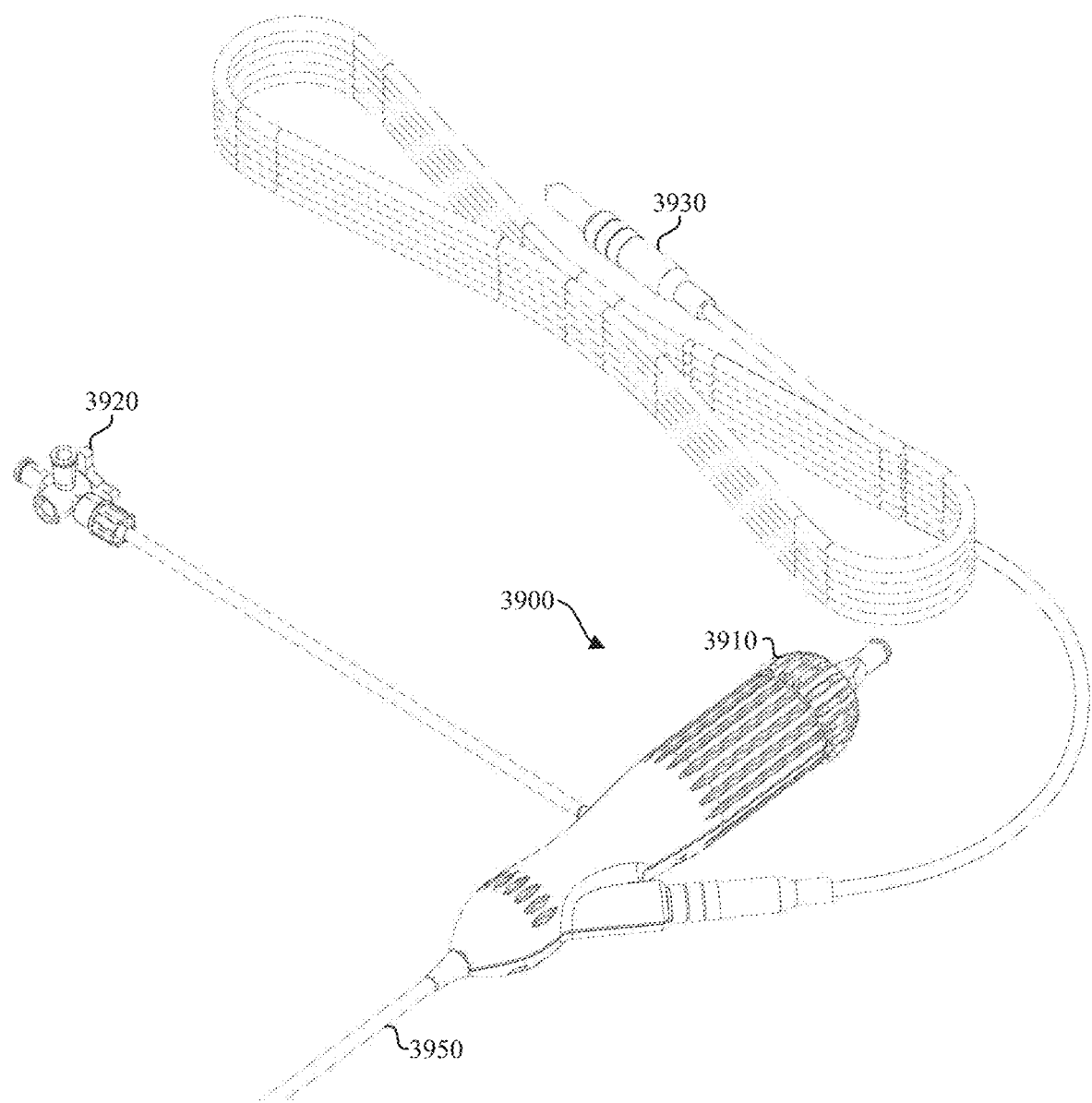
FIG. 39A is a perspective view of an illustrative variation of a handle of an ablation device.
Figure 39B:
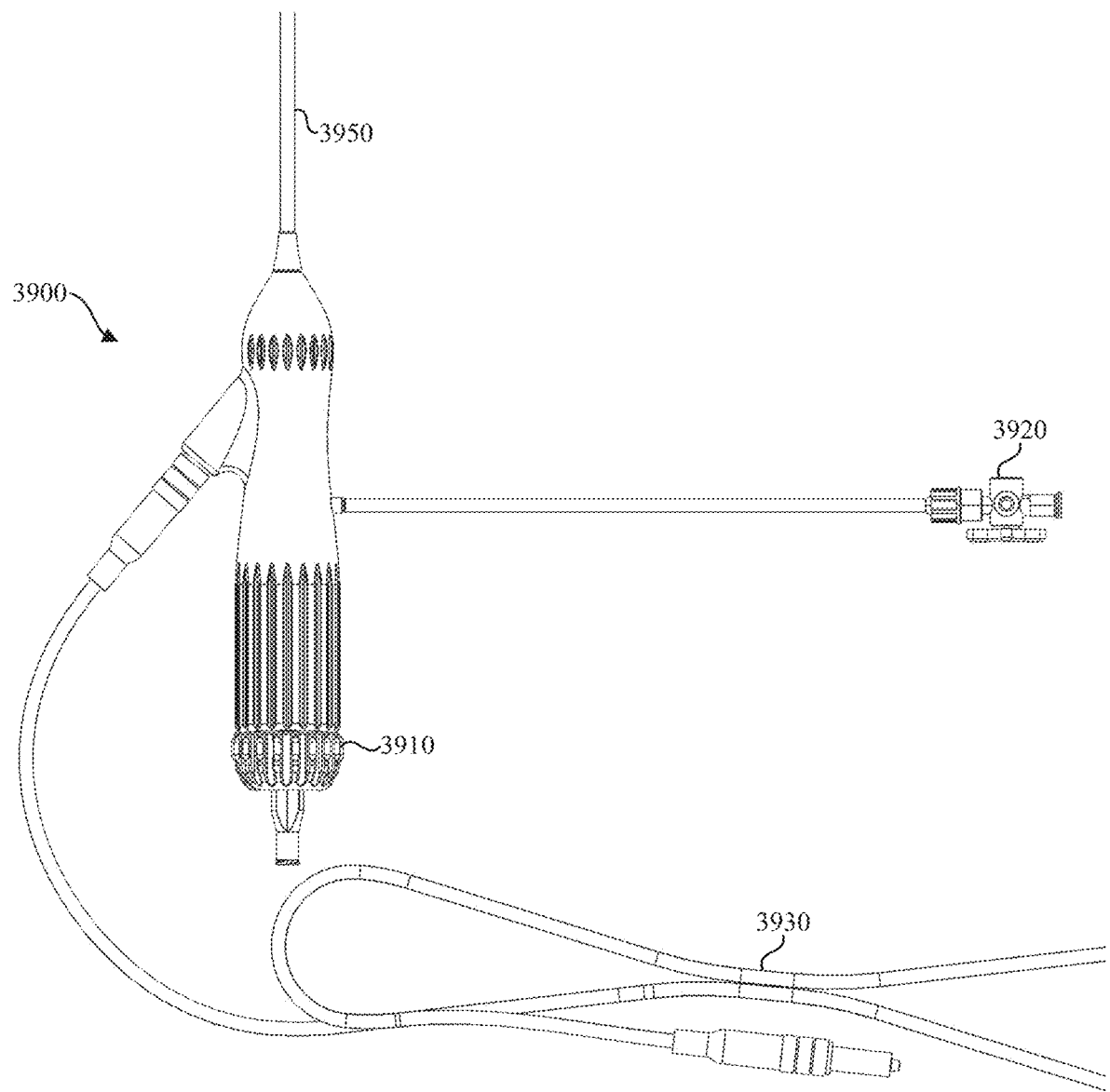
FIG. 39B is a plan view of the handle depicted in FIG. 39A.

FIG. 39A is a perspective view and FIG. 39B is a plan view of a handle (3900) of an ablation device. In some variations, the handle (3900) may comprise one or more actuation mechanisms (3910), fluid ports (3920), and detachable electrical connector (3930). The handle (3900) may be coupled to a proximal end of a first catheter (3950). In some variations, the handle (3900) may be configured to be held (e.g., grasped) by an operator and enable control of one or more of catheter deflection (e.g., steerability), tissue ablation (e.g., electrode energy delivery), catheter translation (e.g., transition between open and closed configuration, tissue compression), and visualization (e.g., contrast fluid delivery).

For example, actuation mechanism (3910) may be configured to control a preload force, as described in detail herein, of a dilator of a second catheter applied against an electrode of the first catheter. In some variations, the actuation mechanism (3910) may comprise a screw mechanism having a plurality of predetermined stops that enable an operator to select an amount of preload at a distal end of the ablation device. For example, an operator may select a predetermined preload force using the actuation mechanism (3910) when the ablation device is in a cutting configuration where tissue is compressed between an electrode and a dilator. In some variations, the actuation mechanism (3910) may be coupled to a shaft of a second catheter such that the actuation mechanism (3910) may be configured to pull a distal portion of the second catheter towards the handle (3900) using the screw mechanism.

In some variations, an actuation mechanism (3910) may be configured to actuate one or more first catheter actuators as described herein. For example, the first catheter actuators may be configured to steer and/or deflect a distal portion of the first catheter. That is, the actuation mechanism (3910) may be configured to push and/or pull on the first catheter.

Signal Generator

Generally, the signal generators described here may be configured to provide energy (e.g., energy waveforms) to an ablation device to ablate predetermined portions of tissue such as an interatrial septum. In some variations, an ablation system as described herein may include a signal generator having an energy source and a processor configured to deliver a waveform to deliver energy to tissue (e.g., interatrial septum). The waveforms disclosed herein may aid in forming an anastomosis. In some variations, the signal generator may be configured to control waveform generation and delivery in response to received sensor data. For example, energy delivery may be inhibited unless a pressure sensor measurement confirms tissue engagement and compression between an electrode and corresponding mating surface.

The signal generator may generate and deliver several types of signals including, but not limited to, radiofrequency (RF), direct current (DC) impulses, stimulus range impulses, and/or hybrid electrical impulses. For example, the signal generator may generate monophasic (DC) pulses and biphasic (DC and AC) pulses. The signal generator may comprise a processor, memory, energy source, and user interface. The processor may incorporate data received from one or more of memory, energy source, user interface, ablation device. The memory may further store instructions to cause the processor to execute modules, processes and/or functions associated with the system, such as waveform generation and delivery. For example, the memory may be configured to store patient data, clinical data, procedure data, and the like.

In some variations, the signal generator may be configured to generate alternating current, voltage, and/or power in the radiofrequency spectrum between about 9 kHz and about 300 MHz at a power level between about 5 W and about 500 W. In some variations, the RF generator is operated by outputting constant voltage, constant power, and/or constant current. In some variations, the RF generator outputs a constant sine wave throughout the duration of tissue cutting. For example, the RF generator may be configured to output a sine wave between about 400 kHz and about 600 kHz, between about 450 kHz and about 550 kHz, and between about 475 kHz and about 525 kHz, including all values and sub-ranges in-between. In some variations, the RF signal output is interrupted and dampened such that RF energy is applied for a fixed percentage of operation time.

In some variations, the signal generator may be configured to synchronize energy delivery with a predetermined phase of a patient's cardiac cycle. For example, a sensor may be configured to measure an ECG signal and the signal generator may be configured to deliver a signal waveform based on (e.g., in synchronicity) with the ECG signal. Additionally or alternatively, a pacing signal for cardiac stimulation may be generated and used to deliver a signal waveform by the signal generator in synchronization with the pacing signal.

Figure 37:
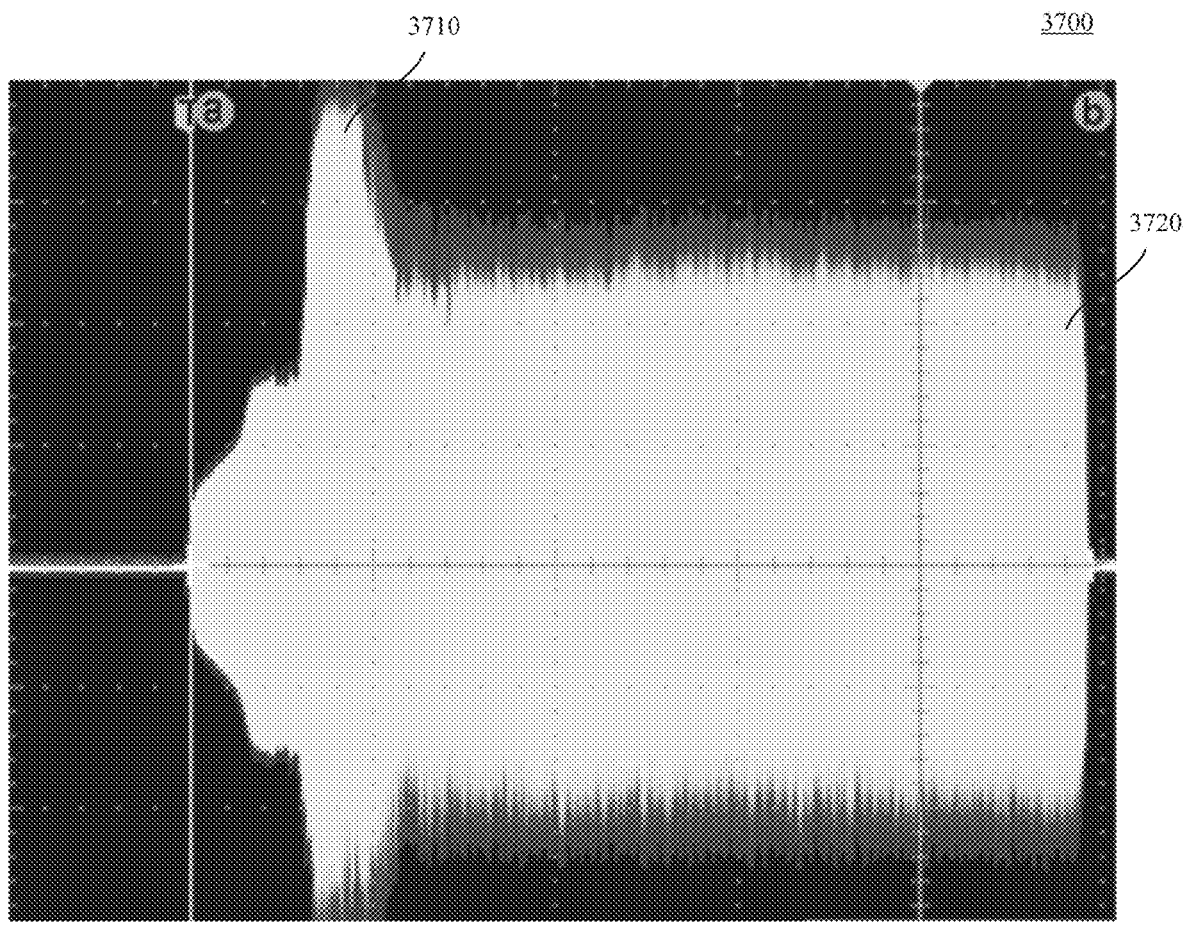
FIG. 37 is an illustrative variation of a voltage waveform of an ablation procedure.

FIG. 37 is a voltage waveform (3700) of an illustrative variation of an ablation procedure comprising a first waveform (e.g., overshoot spike) (3710) and a second waveform (e.g., substantially steady-state voltage) (3720). In some variations, a signal generator may be configured to generate a first waveform (3710) followed by a second waveform (3720) where the first waveform comprise a first voltage higher than a second voltage of the second waveform. The first waveform (3710) may be configured to cut tissue quickly upon energy delivery. The second waveform (3720) having a lower voltage may reduce one or more of thermal spread, bubbling, neurostimulation, and the like. The second waveform may be configured to desiccate the cut tissue held within the ablation device, thereby aiding containment and compartmentalization of tissue.

Alternatively, the first waveform may be configured to desiccate the tissue. For example, the first waveform may comprise a voltage below an ionization threshold of vapor (e.g., below about 130 volts) for a duration of between about 100 msec and about 60 seconds. Impedance may be monitored to prevent plasma formation.

Generally, the processor (e.g., CPU) described here may process data and/or other signals to control one or more components of the system. The processor may be configured to receive, process, compile, compute, store, access, read, write, and/or transmit data and/or other signals. In some variations, the processor may be configured to access or receive data and/or other signals from one or more of a sensor (e.g., pressure sensor) and a storage medium (e.g., memory, flash drive, memory card). In some variations, the processor may be any suitable processing device configured to run and/or execute a set of instructions or code and may include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data and/or power transfer), and/or central processing units (CPU). The processor may be, for example, a general purpose processor, Field Programmable Gate Array (FPGA), an Application Specific Integrated Circuit (ASIC), a processor board, and/or the like. The processor may be configured to run and/or execute application processes and/or other modules, processes and/or functions associated with the system. The underlying device technologies may be provided in a variety of component types (e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Generally, the ablation device described here may comprise a memory configured to store data and/or information. In some variations, the memory may comprise one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some variations, the memory may store instructions to cause the processor to execute modules, processes, and/or functions associated with a ablation device, such as signal waveform generation, ablation device control, data and/or signal transmission, data and/or signal reception, and/or communication. Some variations described herein may relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes.

In some variations, the ablation device may further comprise a communication device configured to permit an operator to control one or more of the devices of the ablation system. The communication device may comprise a network interface configured to connect the ablation device to another system (e.g., Internet, remote server, database) by wired or wireless connection. In some variations, the ablation device may be in communication with other devices (e.g., cell phone, tablet, computer, smart watch, and the like) via one or more wired and/or wireless networks. In some variations, the network interface may comprise one or more of a radiofrequency receiver/transmitter, an optical (e.g., infrared) receiver/transmitter, and the like, configured to communicate with one or more devices and/or networks. The network interface may communicate by wires and/or wirelessly with one or more of the ablation device, network, database, and server.

The network interface may comprise RF circuitry configured to receive and/or transmit RF signals. The RF circuitry may convert electrical signals to/from electromagnetic signals and communicate with communications networks and other communications devices via the electromagnetic signals. The RF circuitry may comprise well-known circuitry for performing these functions, including but not limited to an antenna system, an RF transceiver, one or more amplifiers, a tuner, one or more oscillators, a mixer, a digital signal processor, a CODEC chipset, a subscriber identity module (SIM) card, memory, and so forth.

Wireless communication through any of the devices may use any of plurality of communication standards, protocols and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol. In some variations, the devices herein may directly communicate with each other without transmitting data through a network (e.g., through NFC, Bluetooth, WiFi, RFID, and the like).

In some variations, the user interface may comprise an input device (e.g., touch screen) and output device (e.g., display device) and be configured to receive input data from one or more of the ablation device, network, database, and server. For example, operator control of an input device (e.g., keyboard, buttons, touch screen) may be received by the user interface and may then be processed by processor and memory for the user interface to output a control signal to the ablation device. Some variations of an input device may comprise at least one switch configured to generate a control signal. For example, an input device may comprise a touch surface for an operator to provide input (e.g., finger contact to the touch surface) corresponding to a control signal. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device comprising at least one switch, a switch may comprise, for example, at least one of a button (e.g., hard key, soft key), touch surface, keyboard, analog stick (e.g., joystick), directional pad, mouse, trackball, jog dial, step switch, rocker switch, pointer device (e.g., stylus), motion sensor, image sensor, and microphone. A motion sensor may receive operator movement data from an optical sensor and classify an operator gesture as a control signal. A microphone may receive audio data and recognize an operator voice as a control signal.

A haptic device may be incorporated into one or more of the input and output devices to provide additional sensory output (e.g., force feedback) to the operator. For example, a haptic device may generate a tactile response (e.g., vibration) to confirm operator input to an input device (e.g., touch surface). As another example, haptic feedback may notify that operator input is overridden by the ablation device.

II. Methods

Also described here are methods of forming an anastomosis in an interatrial septum of a patient using the systems and devices described herein. In particular, the systems, devices, and methods described herein may be used to capture, excise, and remove a predetermined portion of tissue to create an anastomosis for treating heart failure. In some variations, a method of forming an anastomosis may include advancing a device into a right atrium of a patient. A guidewire may be advanced across an interatrial septum of the heart and into a left atrium. The device may comprise a dilator configured to puncture the septum such that a first catheter is disposed within the right atrium and a second catheter is disposed in the left atrium. The second catheter may comprise a barb configured to engage and secure tissue when withdrawn relative to the first catheter. As the barb is further withdrawn (e.g., towards the right atrium), the engaged tissue may stretch and/or compress against the barb and form a "tent" shape due to the elasticity of the tissue. The barb and the engaged tented tissue may be withdrawn into a lumen of the electrode (e.g., tubular electrode). By positioning the ablation device across both sides of the interatrial septum, a predetermined force may be applied to engage and/or compress a predetermined portion of septum tissue to be ablated. For example, the electrode of the first catheter may compress septum tissue against a proximal end (e.g., mating surface) of the dilator. The electrode disposed in the right atrium may be energized to cut (e.g., excise) tissue using RF energy using an ablation waveform as described in more detail herein. The excised tissue may be enclosed by the ablation device to prevent tissue loss. For example, excised tissue may be held by the barb and the electrode may surround the excised tissue and barb. Accordingly, the ablation devices described herein may be configured to form an interatrial anastomosis safely and efficiently.

Figure 18:
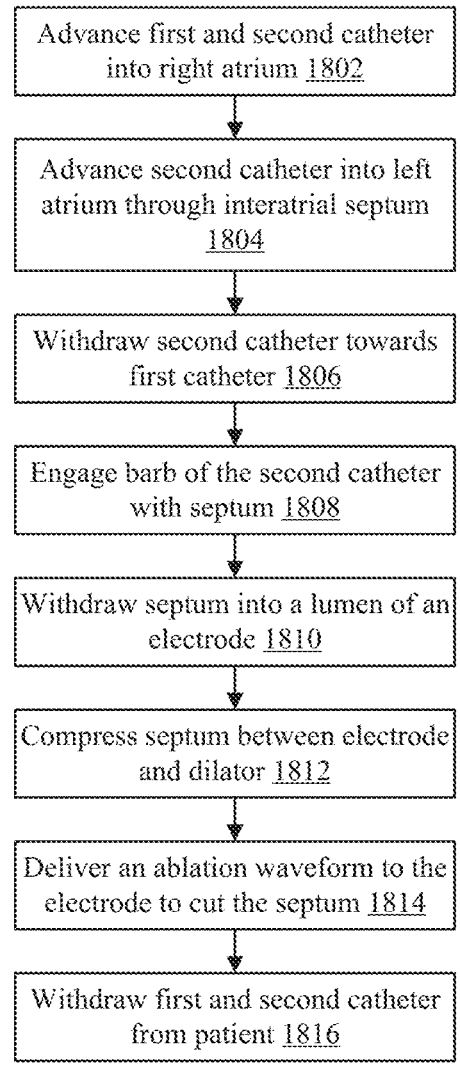
FIG. 18 is a flowchart of an illustrative variation of a method of forming an anastomosis.

FIG. 18 is a flowchart that generally describes a variation of a method of forming an anastomosis (1800). The method (1800) may include advancing an ablation device comprising a first catheter and a second catheter into a right atrium of a patient (1802). For example, the ablation device may be advanced over a guidewire and inserted through the femoral vein using, for example, a transseptal puncture method. In some variations, the ablation device within the right atrium may be oriented approximately perpendicular to an interatrial septum. For example, a first catheter actuator as described herein may be configured to deflect a distal portion of the ablation device to reposition the ablation device relative to the interatrial septum. The first catheter may abut the second catheter when advanced into the heart. For example, a delivery catheter may be configured to hold each of the first catheter and the second catheter until deployment in the heart.

The ablation device catheters may be indirectly visualized as necessary throughout an ablation procedure. Indirect visualization, such as echocardiography and/or fluoroscopy, may assist an operator in positioning and/or aligning the ablation device relative to tissue. For example, under ultrasound imaging, a contrast agent such as microbubbles may be introduced into an endocardial space using the ablation device in order to position an electrode and/or dilator relative to an interatrial septum disposed therebetween. A user may then bring the catheters into close approximation to compress and cut the tissue. In some variations, the ablation device may be configured to output microbubbles in a closed configuration for ultrasonic visualization of the ablation device and interatrial septum.

In some variations, a contrast agent may be introduced into the heart via a fluid port in the dilator. In some of these variations, a contrast agent may be introduced into a lumen of the electrode. Additionally or alternatively, a distal end of the ablation device may comprise an echogenic region may receive ultrasound waves. For example, the distal end of the ablation device may comprise one or more microspheres comprising a diameter of between about 5 μm and about 100 μm.

Figure 32:
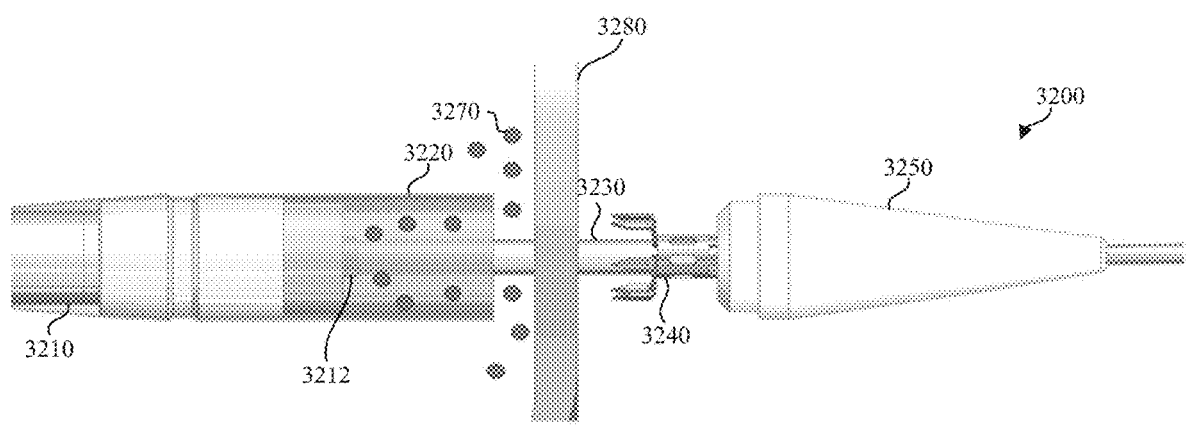
FIG. 32 is a side view of an illustrative variation of an ablation device in an endocardial space.

FIG. 32 is a side view of an ablation device (3200) in an endocardial space. In some variations, ablation device (3200) may comprise a first catheter (3210), an electrode (3220), second catheter (3230), barb (3240), and dilator (3250). The ablation device (3200) is depicted in an open configuration with tissue (e.g., interatrial septum) (3280) disposed between the electrode (3220) spaced apart from the barb (3240) and dilator (3250). In some variations, the first catheter (3120) may be configured to output a contrast agent (e.g., microbubbles) (3270) into a lumen of the electrode (3220) and endocardial space. For example, a contrast agent lumen (3212) of the first catheter (3210) may be configured to output a contrast agent (3270) into a lumen of the electrode (3220). Contact between the contrast agent (3270) and the electrode (3220) and tissue (3280) may enable indirect visualization (e.g., echocardiography) of one or more steps of an ablation procedure. Visualization of the ablation device (3200) and tissue (3280) may aid positioning of the electrode with respect to the tissue (3280). For example, contrast agent (3270) may be introduced into a right atrium prior to engaging the tissue (3280) using the barb. The contrast agent (3270) flowing through the lumen of the electrode (3220) and the endocardial space may allow visualization of the electrode (3220) and the right atrium side of the interatrial septum.

Figure 19A:
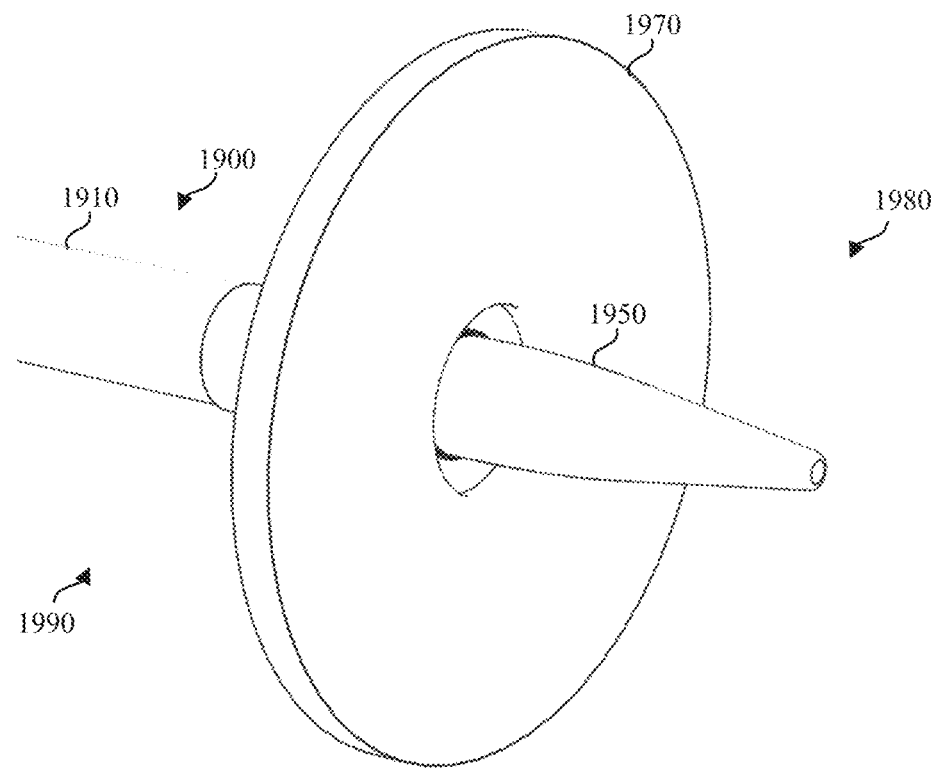
FIGS. 19A and 19B are schematic perspective views of an illustrative variation of an ablation device in an endocardial space.
Figure 19B:
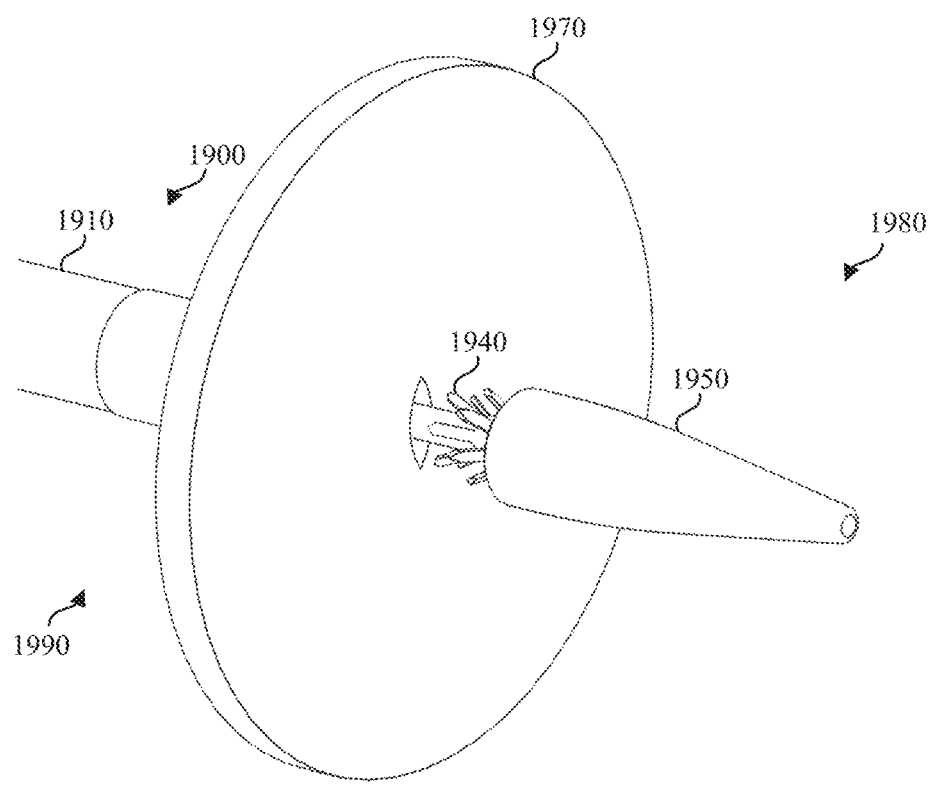

The second catheter may be advanced into a left atrium through the interatrial septum (1804). For example, a dilator of the second catheter may be advanced (e.g., over a guidewire) across the interatrial septum such that the guidewire and dilator are located in the left atrium. The second catheter may be translated relative to the first catheter. A barb of the second catheter may be advanced into the left atrium such that the electrode of the first device may be located in the right atrium. Septum tissue may slide over the barb as it is advanced into the left atrium. As shown in FIGS. 19A and 19B, an ablation device (1900) may be disposed within a right atrium (1990) and advanced into a left atrium (1980) using a dilator of a second catheter (1950). The second catheter (1950) may be translated relative to a first catheter (1910) in the right atrium (1990) and the interatrial septum (1970). The barb (1940) of the second catheter (1950) may be advanced through the septum (1970) and into the left atrium (1980). As shown in the cross-sectional side view of FIG. 19C, the first catheter (1910) may comprise a tubular electrode (1920), a lumen (1922), a lead (1924), connector (1926), and insulator (1960). The second catheter (1950) may comprise a barb (1940), mating surface (1954), dilator, and dilator lumen (1952).

In some variations, the ablation device may introduce a contrast agent (e.g., microbubbles) for visualization an interface between the dilator, tissue, and electrode. In some variations, the electrode may be repositioned between about 2 mm and about 5 mm away from the interatrial septum based on the visualization.

The second catheter may be withdrawn relative to the first catheter (1806). For example, the second catheter may be translated toward the first catheter to bring the electrode and dilator closer together. In some variations, the second catheter may be withdrawn while the first catheter is held in a substantially fixed position in the right atrium. In some variations, a contrast agent (e.g., microbubbles) may be introduced to confirm a position of the barb, tissue, and electrode.

In some variations, withdrawing the second catheter towards the first catheter may comprise translating the barb relative to the dilator to engage the first portion of the septum. For example, the barb may be withdrawn away from the dilator as shown in FIGS. 30A and 30B. In particular, the first catheter (3030) may transition from a first configuration where the barb (3020) is arranged inside a recess (3040) of the dilator (3030) to a second configuration where the barb (3020) is arranged outside the recess (3040).

As the second catheter is withdrawn, the barb of the second catheter may engage a predetermined portion of the septum (1808). In some variations, as shown in FIGS. 29A-29C, may comprise rotating the barb about a longitudinal axis of the barb. A size of a first tissue portion cut from a second tissue portion may correspond to a rotation angle of the barb. The barb may be rotated at a rotation angle of up to about 360 degrees.

As shown in FIG. 19D, as the second catheter (1950) is withdrawn relative to the first catheter (1910), the barb (1940) may engage septum tissue (1970). For example, the barb may pierce through the first portion when withdrawing the second catheter towards the first catheter. The barb may pierce through the first portion such that the layers of an interatrial septum (e.g., left and right atrium layers) are held together to reduce tissue separation and/or tissue shearing. Accordingly, the barb (1940) may capture (e.g., secure, hold) tissue (1970) while maintaining the structural integrity of the septum. In some variations, the withdrawn barb may apply a force to the septum to hold and stretch the portion (e.g., first portion) of the septum over the barb. The force may increase as the second catheter is withdrawn further towards the first catheter. In some variations, withdrawal of the second catheter may apply a force of at least 20 grams to the interatrial septum. For example, the ablation device may apply a force of between about 20 grams and about 30 grams to the interatrial septum. In some variations, the first portion of the septum may form a substantially cylindrical shape when withdrawn into the lumen.

The barbs described herein have a configuration designed to engage the first portion of the septum without shearing the tissue (e.g., breaking or tearing through one or more layers of the interatrial septum) such that the first portion remains intact when engaged to the barb and withdrawn into the lumen of the electrode. That is, the forces applied by the barbs described herein allow the structural integrity of the first portion to be maintained even when the barb pierces through the septum. This may ensure that the first portion of the septum to be excised remains held and secured by the barb throughout the procedure, thereby improving the consistency and safety of the methods described herein.

Figure 19E:
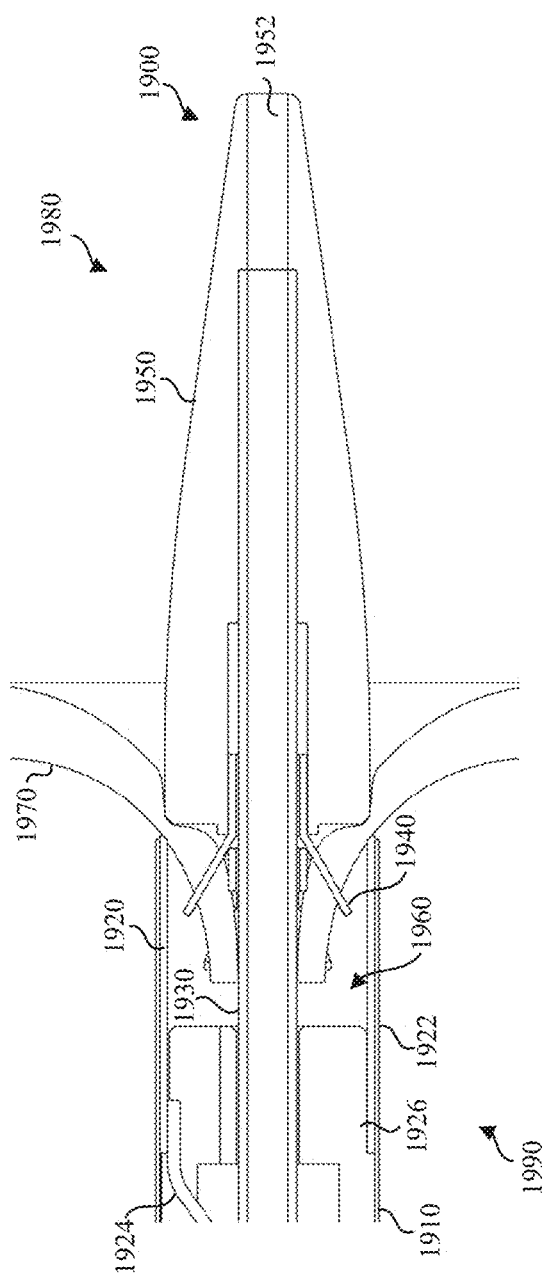

The septum may be withdrawn into a lumen of an electrode (1810). In some variations, a portion of the interatrial septum may form a tent over the barb as the septum is withdrawn into the lumen of the electrode. In this manner, tissue to be cut may be secured within the ablation device prior to excision to reduce the risk of uncontrolled tissue loss in the heart chambers and vasculature. As shown in FIG. 19E, a portion of the septum (1970) may form a tent-like shape over the barb (1940). In some variations, the barb (1940) engaged to tissue may rotate as it is withdrawn into the lumen of the electrode to apply a rotational force to the stretched (e.g., tented) septum tissue. In some variations, a size (e.g., diameter) of the tissue (1970) to be cut may be controlled by varying a distance that the engaged tissue (1970) is withdrawn into the lumen (1922). Therefore, a size of an anastomosis may be independent of the electrode diameter. By withdrawing the second catheter towards the first catheter, the ablation device (1900) engages, stretches, compresses, locks, and tents the tissue, as well as controls a size of the opening to be cut. In some variations, the size of an anastomosis may depend on the distance the barb is withdrawn into the electrode such that a size of an anastomosis may be independent of the diameter of the ablation device.

In some variations, a contrast agent (e.g., microbubbles) may be introduced to confirm a position of the barb, tissue, and electrode (e.g., confirm that the electrode is in the right atrium).

The septum may be compressed (1812) between the electrode and dilator. As shown in FIG. 19E, a portion of the interatrial septum (1970) may be held between the electrode (1920) and the dilator (1950). For example, the electrode and the dilator may be brought together to abut (e.g., compress) opposite sides of the interatrial septum (1970) to "lock" the tissue (1970) in place relative to the ablation device (1900). In some variations, the force applied to the interatrial septum by the barb (1940) and through compression may be applied prior to and during delivery of the ablation waveform. The compressed tissue may allow a reduction in applied RF energy necessary to cut the tissue. In some variations, one or more of the barb and dilator may be rotated about a longitudinal axis of the second catheter to further engage and/or compress tissue.

In some variations, as shown in FIG. 35B, withdrawing the second catheter towards the first catheter may deform a compressible proximal portion of the dilator.

FIG. 36A is a side view of an ablation device (3600) in an endocardial space illustrating compression step of an ablation procedure. In some variations, the ablation device (3600) may comprise a first catheter (3610), an electrode (3620), second catheter (3630), barb (3640), and dilator (3650). In some variations, the first catheter (3610) may comprise a contrast agent lumen (3612) as described in more detail herein. In some variations, the electrode (3620) may comprise a lumen configured to hold one or more of the barb (3640), a first portion (3672) of tissue, and a proximal portion (3652) of the dilator (3650). In some variations, a guidewire (3630) may be slidably disposed within the second catheter (3630).

As depicted in FIG. 36A, the barb (3640) may be configured to engage a first portion (3672) of the interatrial septum (3670) in a cutting configuration where the tissue (3674) is compressed between a distal edge of the electrode (3630) and the proximal portion (3652) of the dilator (3650). For example, a distal end of an electrode (3620) may be configured to abut against a corresponding mating surface (3652) of the dilator (3650). For example, the second catheter (3630) may be withdrawn with respect to the first catheter (3610) such that a mating surface (3652) applies a preload force to the tissue (3674) and electrode (3620). In some variations, application of the preload force may be controlled by an operator via an actuator of a handle. Compression of the tissue between the electrode and mating surface (via the preload force) may reduce the thickness of the tissue to be cut such that a septum may be cut faster and with less energy. Furthermore, compressed tissue may hold (e.g., secure, lock) the tissue in place relative to the ablation device to ensure that only a predetermined portion of tissue is cut. Compression of tissue may also reduce a volume of tissue. In some variations, a preload force may be between about 0.4 N to about 25 N, about 1 N to about 10 N, about 5 N to about 10 N, about 5 N to about 15 N, about 10 N to about 20 N, including all ranges and sub-values in-between.

In some variations, the compressed tissue (3674) and the dilator (3650) may come to rest in a static equilibrium state where the proximal portion (3652) of the dilator (3650) compresses the tissue (3674) against the electrode (3620) with a shear force comprising a radial component. In some variations, extension of the dilator (3650) prior to cutting is beneficial to the operator when viewed fluoroscopically. In some variations, the ablation device (3600) in the cutting configuration (FIG. 36A) may correspond to a dilator (3650) being extended about 1 mm away from an end of the electrode (3620).

An ablation waveform may be delivered to the electrode to cut the septum (1814). For example, a signal generator may generate a biphasic radiofrequency waveform configured to ablate a portion of the interatrial septum held by the device. In some variations, the electrode may be configured to transmit 50 mA to 4 A of current between about 0.1 kV and about 4.0 kV at a rate of up to about 500 kHz.

In some variations, delivery of the ablation waveform may be controlled based on a distance between the electrode and the dilator. For example, the electrode may be configured to electrically short when the electrode contacts the mating surface of the dilator during delivery of the ablation waveform.

In some variations, the ablation waveform may comprise a first waveform followed by a second waveform. The first waveform may comprise a first voltage and the second waveform may comprise a second voltage. The first voltage may be higher than the second voltage.

Figure 19F:
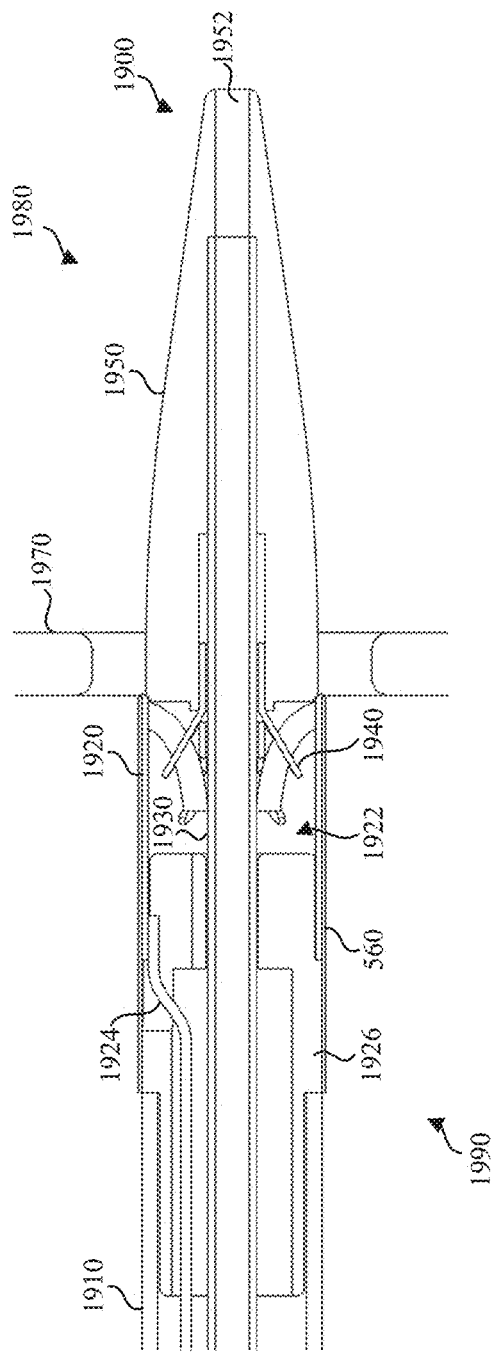

FIG. 19F illustrates the interatrial septum (1970) defining the predetermined opening and the ablation device (1900) holding the excised tissue by the barb (1940) within the lumen (1922) of the electrode (1920). As shown in FIG. 19F, the septum (1970) may snap back after excising the tissue engaged by the barb (1940). The tissue within the lumen (1922) may be sealed within the ablation device (1900) once ablation is completed and the electrode contacts the dilator (1950). In this manner, excised tissue may be prevented from being lost in the body.

Figure 36B:
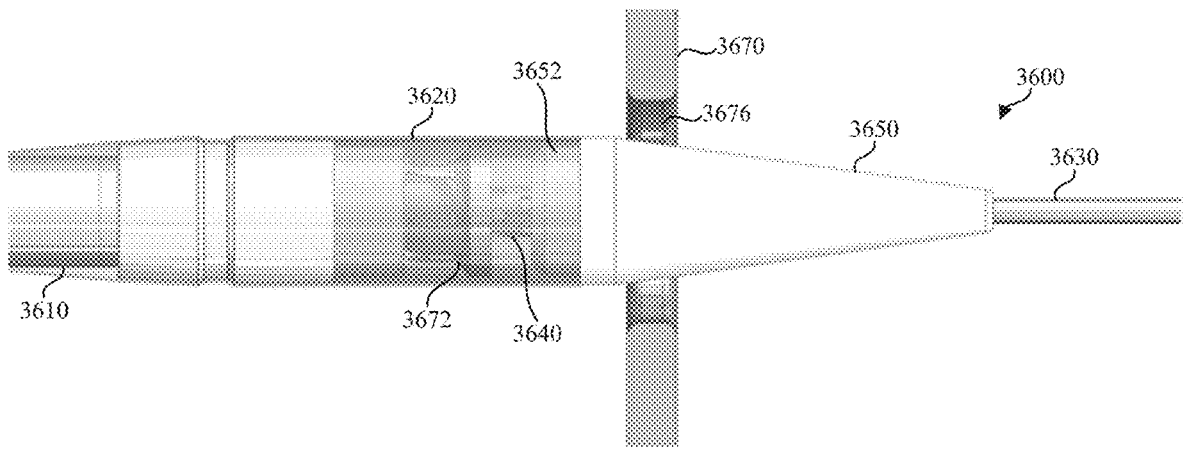

FIG. 36B depicts the ablation device (3600) in a closed (e.g., seated) configuration with cut tissue (e.g., first portion) (3672) engaged to the barb (3640) and held within a lumen of the electrode (3620). The proximal portion (3652) of the dilator (3650) may be, for example, seated within the lumen of the electrode (3620). FIG. 36B depicts a hole (3676) formed in the interatrial septum (3670).

In some variations, visualization may confirm the completion of an energy delivery process. For example, the differences between the ablation device (3600) in the cutting configuration (FIG. 36A) and the closed configuration (FIG. 36B) may be confirmed through indirect visualization. For example, fluoroscopic visualization may confirm when tissue is interposed between the electrode (3620) and dilator (3650) and when tissue has been cut after energy delivery based on an imaged position of the dilator (3650) relative to the electrode (3620).

In some variations, a preload force (e.g., first predetermined force) may be applied by the dilator (3650) to the electrode (3620) during and/or after energy delivery to ensure withdrawal of the second catheter (3630) towards the first catheter (3610). In some variations, an operator may activate a switch in a handle to initiate energy delivery to cut tissue. As the proximal portion (3652) withdraws toward and compresses against the electrode (3620) during energy delivery, the proximal portion (3652) may shear (e.g., cut, separate) the tissue from the septum (3670) with a second predetermined force greater than the first predetermined force. That is, the proximal portion (3652) may function as a cutting board to ensure that even small fibers of tissue (3674) (e.g., second portion) are cut from the septum (3670). Alternatively, a preload force may not be applied to the tissue (3674) and electrode (3620) when delivering an ablation waveform to the electrode (3620). During energy delivery, the dilator (3650) may naturally withdraw into the lumen of the electrode (3620) after tissue (3674) is cut (e.g., ablated)

In some variations, a proximal portion (3652) of the dilator (3650) as shown in FIG. 36B may be disposed within a lumen of the electrode (3620) when a mating surface (e.g., proximal portion (3652)) engages the electrode. The proximal portion (3652) arranged within the lumen of the electrode (3620) may securely and coaxially attach the electrode to the dilator. For example, the dilator may be secured to the first catheter (3610) to withstand dislodgment from a lateral load such as when the ablation device is tracked over a curved guidewire. Furthermore, the electrode (3620) securely engaged to the dilator (3650) may be configured to prevent the ablation device (3600) from catching (e.g., snagging) against a vessel, tissue (e.g., transseptal crossing), introducer, sheath, and the like during advancement and withdrawal through a body cavity. In some variations, between about 0.5 mm and about 2 mm of the proximal portion (3652) of the dilator (3650) may be disposed within the lumen of the electrode (3620) when the mating surface engages the electrode (3620). In some variations, the ablation device (3600) shown in FIG. 36B may be withdrawn from the patient.

The first and second catheter may be withdrawn from the patient (1816). This may include withdrawing the excised tissue held within the first catheter as the first and second catheters are withdrawn together. In some variations, the procedure may be ultrasonically and/or fluoroscopically imaged during one or more steps.

EXAMPLES

Figure 20:
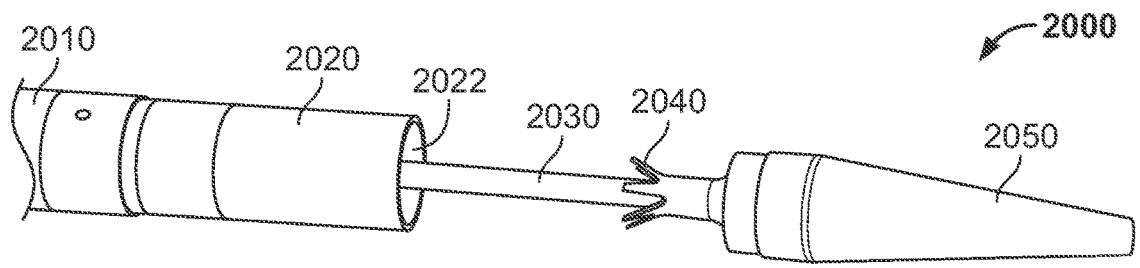
FIG. 20 is a perspective view of an illustrative variation of an ablation device.
Figure 21:
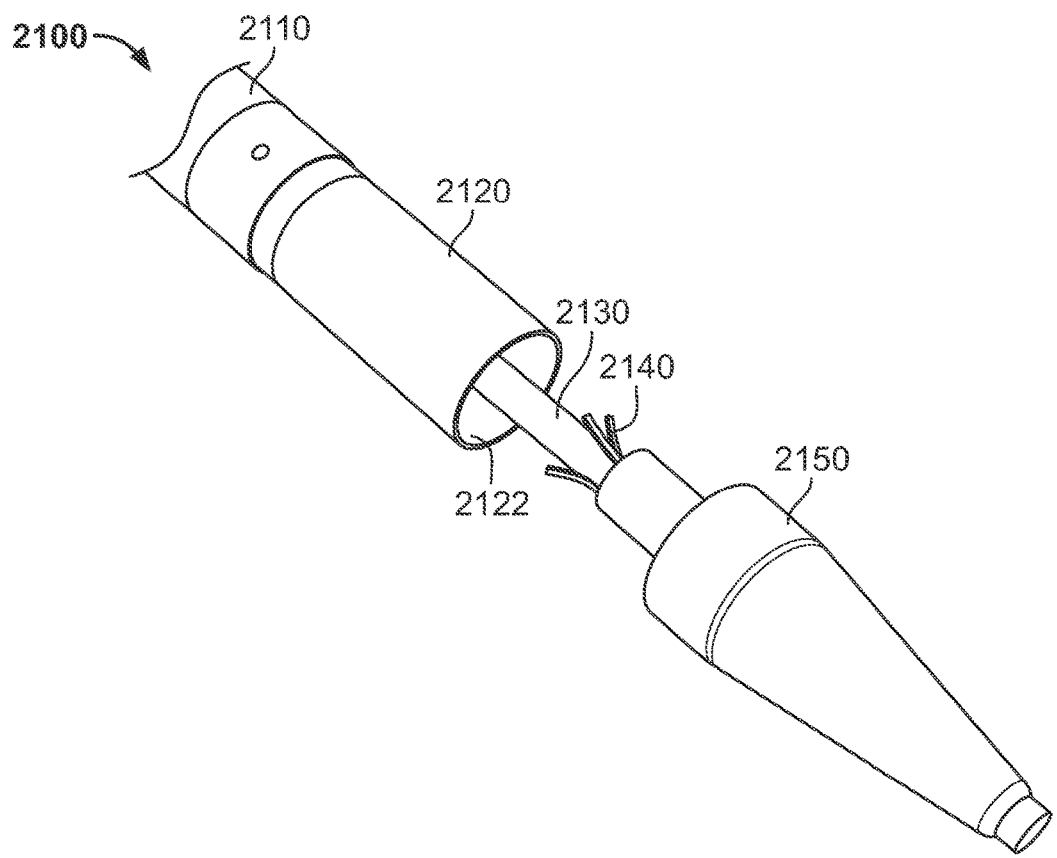
FIG. 21 is a perspective view of an illustrative variation of an ablation device.

FIGS. 20 and 21 are perspective views of variations of ablation devices (2000, 2100). In some variations, the ablation device (2000, 2100) may comprise a first catheter (2010, 2110) and a second catheter (2030, 2130). The first catheter (2010, 2110) may comprise a tubular electrode (2020, 2120). The electrode (2020, 2120) may define a lumen (2022, 2122) configured to hold a barb (2040, 2140) of the second catheter (2030, 2130). The tubular electrode (2020, 2120) may comprise a cylindrical shape. In some variations, the ablation device (2000, 2100) may comprise a second catheter (2030, 2130) slidably disposed within the first catheter (2010, 2110). The second catheter (2030, 2130) may comprise a barb (2040, 2140) and a dilator (2050, 2150) configured to engage the electrode (2020, 2120). In some variations, the barb (2040, 2140) may comprise a plurality of projections that are angled generally towards the electrode (2020, 2120). The dilator (2050, 2150) may comprise a tapered, conical shape. FIG. 22 is perspective view of an ablation device (2200) engaged by excised tissue (2260). In some variations, the ablation device (2200) may comprise a first catheter (2210) and a second catheter (2230). The excised tissue (2260) fits within a lumen (2222) of the electrode (2220) for removal from a patient.

Figure 23:
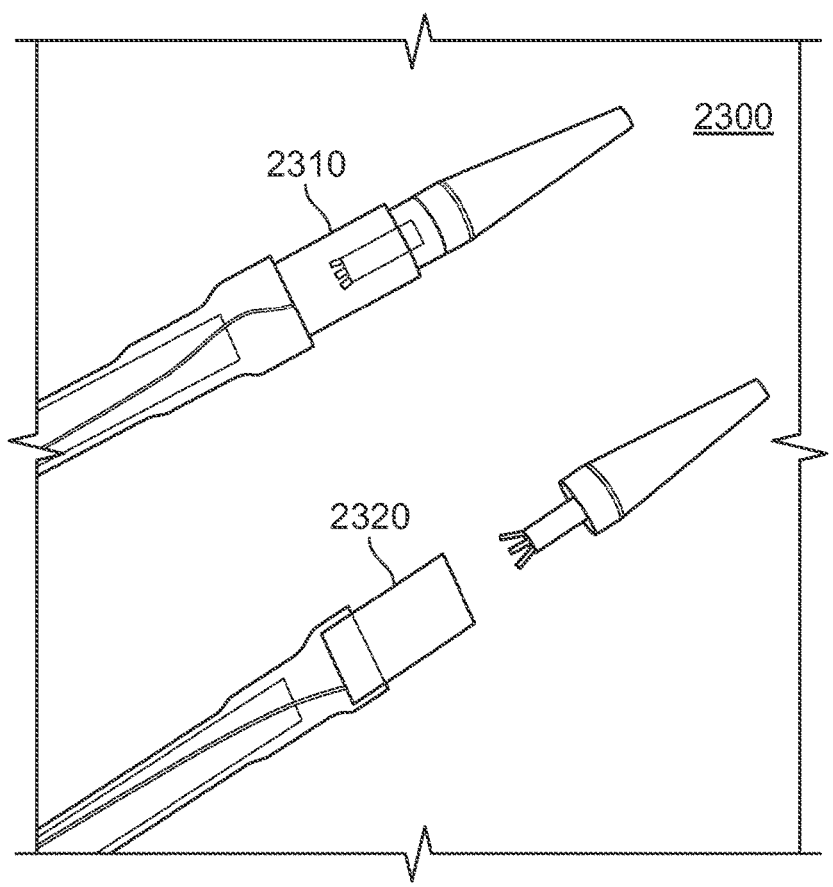
FIG. 23 is a fluoroscopic visualization of illustrative variations of the ablation device in open and closed configurations.

FIG. 23 is a fluoroscopic visualization (2300) of ablation devices (2310, 2320) in respective open and closed configurations. One or more portions of the ablation devices (2310, 2320) may comprise a radiopaque portion.

Figure 24:
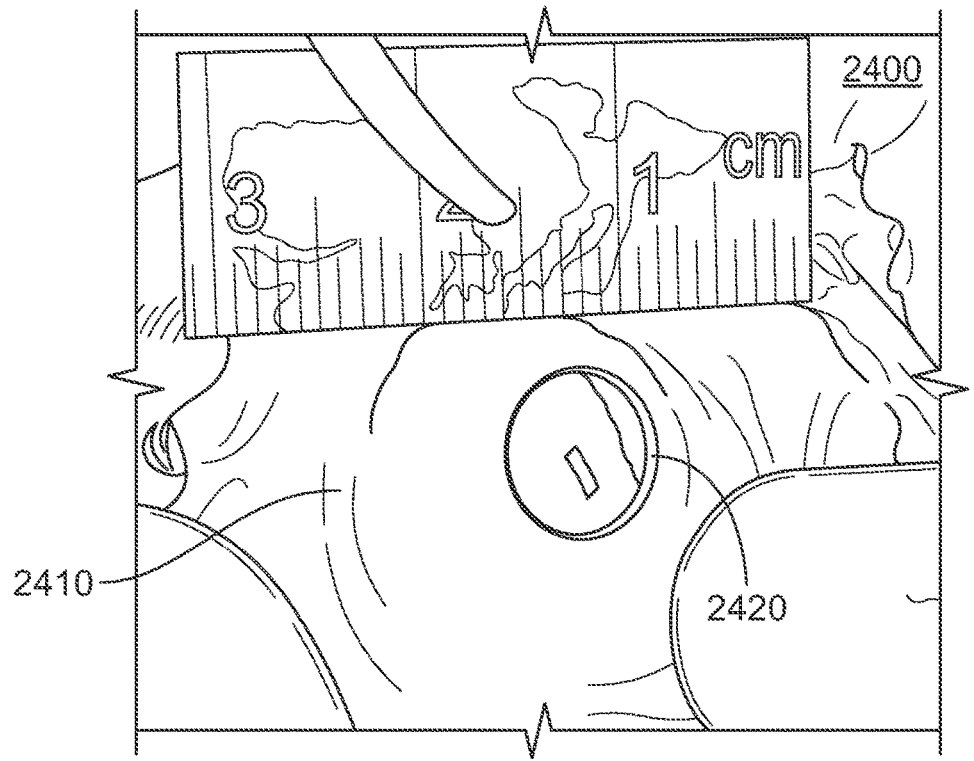
FIG. 24 is an image of an anastomosis formed in cadaver tissue.
Figure 25A:
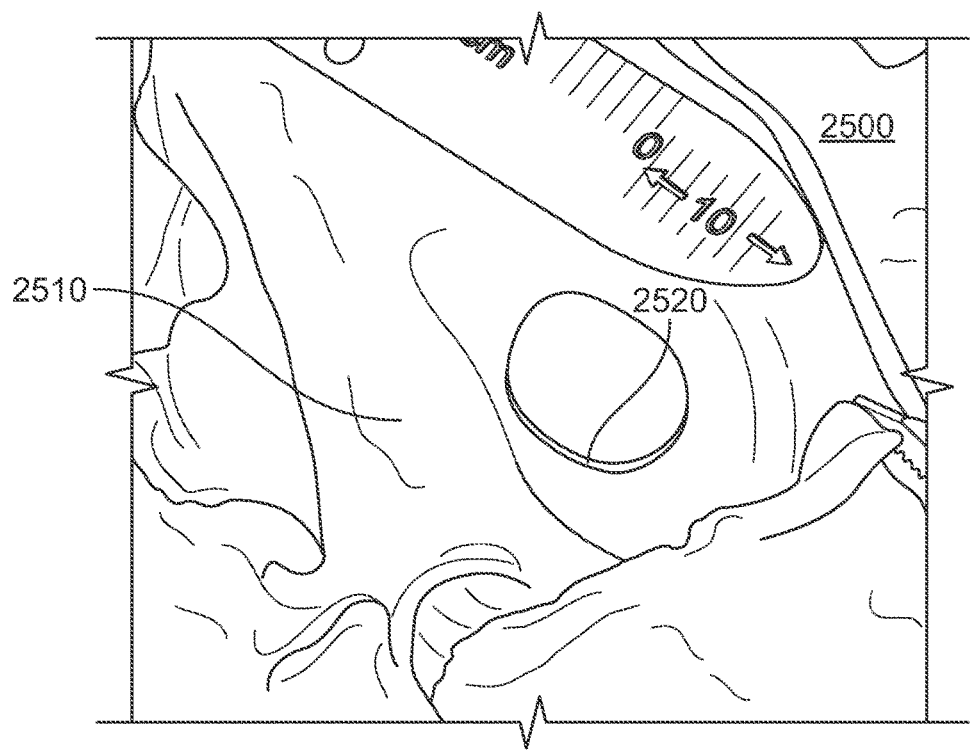
FIGS. 25A and 25B are images of an anastomosis formed in porcine tissue.
Figure 25B:
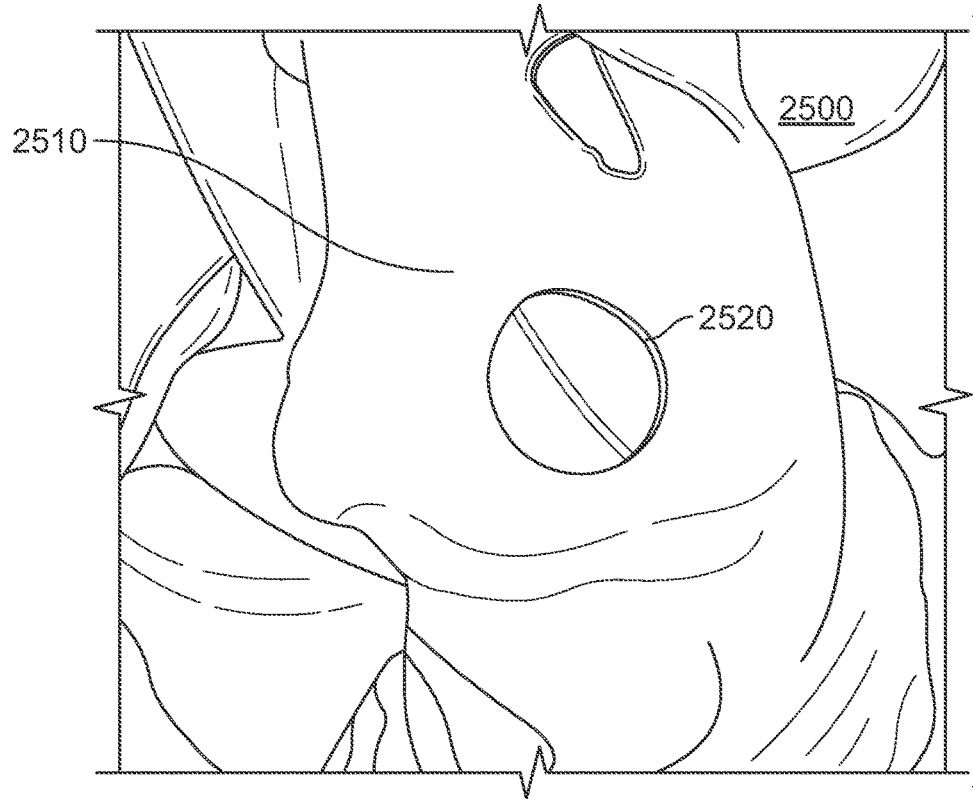

FIG. 24 is an image (2400) of an anastomosis (2420) formed in cadaver tissue (2410) using the ablation systems and methods described herein. FIGS. 25A and 25B are images (2500) of an anastomosis (2520) formed in porcine tissue (2510) using the ablation systems and methods described herein.

FIGS. 27A and 27B are perspective views of variations of an ablation device (2700) engaged to tissue (2760). In some variations, the ablation device (2700) may comprise a first catheter (2710) and a second catheter (2730). The first catheter (2710) may comprise a tubular electrode (2720). The electrode (2720) may define a lumen (2722) configured to hold a barb (2740) of the second catheter (2730). The tubular electrode (2720) may comprise a cylindrical shape. In some variations, the ablation device (2700) may comprise a second catheter (2730) slidably disposed within the first catheter (2710). The second catheter (2730) may comprise a barb (2740) similar to the variation depicted in FIGS. 26A and 26B and a dilator (2750) configured to engage the electrode (2720). In some variations, the barb (2740) may comprise a plurality of projections comprising tissue engagement portions that are substantially parallel to a longitudinal axis of the second catheter (2730). The dilator (2750) may comprise a tapered, conical shape.

Figure 27C:
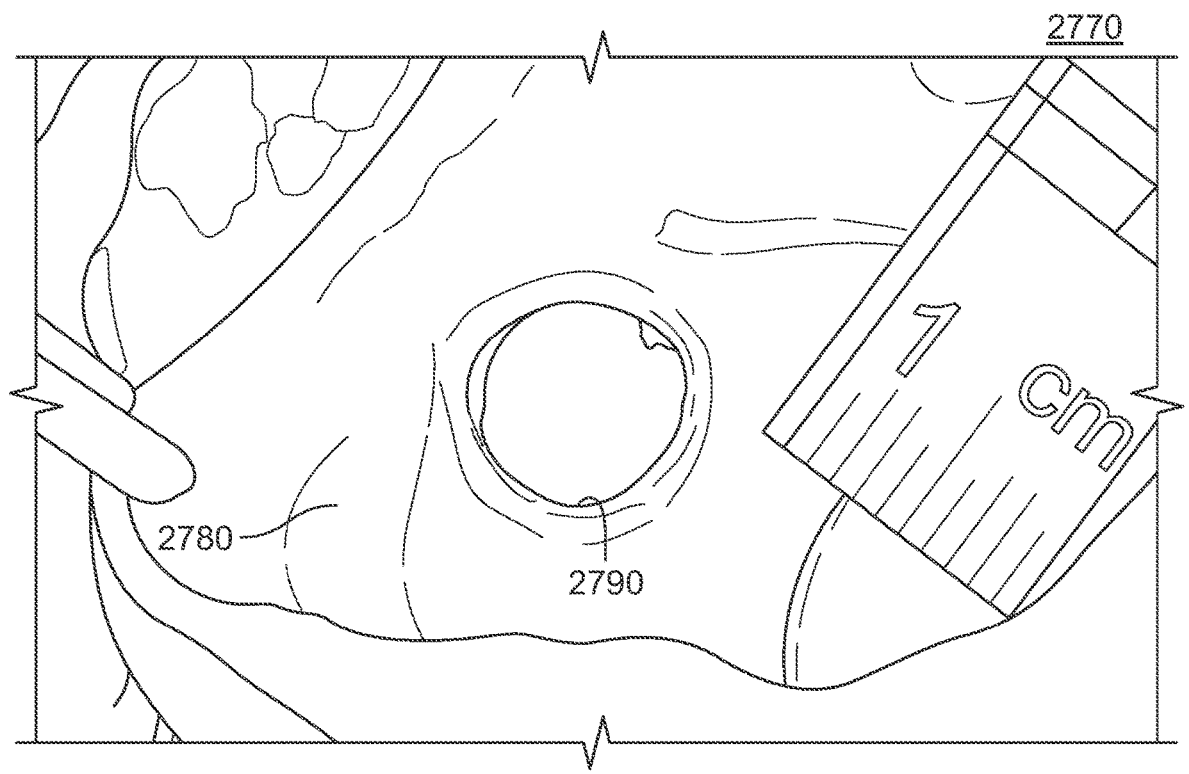
FIG. 27C is an image of an anastomosis formed in tissue.

Tissue (2760) may be configured to be engaged to the barb (2740) as described in more detail herein. Although the second catheter (2730) is advanced relative to the first catheter (2710) in FIGS. 27A and 27B to show the barb (2740) and excised tissue (2760), the excised tissue (2260) fits within a lumen (2722) of the electrode (2720) to facilitate tissue removal from a patient. In some variations, the lumen (2722) may have a length of at least 1 mm. For example, the lumen (2722) may have a length between about 5 mm and about 4 cm. FIG. 27C is an image (2770) of an anastomosis (2790) formed in tissue (2780) using the ablation systems and methods described herein.

FIGS. 28A and 28B are perspective views of variations of an ablation device (2800) engaged to tissue (2860). In some variations, the ablation device (2800) may comprise a first catheter (not shown) and a second catheter (2830). In some variations, the ablation device (2800) may comprise a second catheter (2830) slidably disposed within the first catheter. The second catheter (2830) may comprise a barb (2840) similar to the variation depicted in FIGS. 26A and 26B and a dilator (2850). In some variations, the barb (2840) may comprise a plurality of projections comprising tissue engagement portions that are substantially parallel to a longitudinal axis of the second catheter (2830). Tissue (2860) may be configured to be engaged to the barb (2840) as described in more detail herein.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

The specific examples and descriptions herein are exemplary in nature and variations may be developed by those skilled in the art based on the material taught herein without departing from the scope of the present invention, which is limited only by the attached claims Although the foregoing implementations has, for the purposes of clarity and understanding, been described in some detail by of illustration and example, it will be apparent that certain changes and modifications may be practiced, and are intended to fall within the scope of the appended claims. Additionally, it should be understood that the components and characteristics of the elements described herein may be used in any combination, and the methods described herein may comprise all or a portion of the elements described herein. The description of certain elements or characteristics with respect to a specific figure are not intended to be limiting or nor should they be interpreted to suggest that the element cannot be used in combination with any of the other described elements.

In addition, any combination of two or more such features, structure, systems, articles, materials, kits, steps and/or methods, disclosed herein, if such features, structure, systems, articles, materials, kits, steps and/or methods are not mutually inconsistent, is included within the inventive scope of the present disclosure. Moreover, some variations disclosed herein may be distinguishable from the prior art for specifically lacking one or more features, elements, and functionality found in a reference or combination of references (i.e., claims directed to such variations may include negative limitations).

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The invention claimed is:

1. A method of forming an anastomosis in a heart, comprising:
    advancing a first and second catheter into a right atrium, wherein the first catheter comprises an atraumatic electrode defining a lumen and the second catheter comprises a dilator and a barb, wherein a largest outer diameter of the barb is less than a largest outer diameter of the dilator, and a largest outer diameter of a base portion is less than a largest outer diameter of the barb;
    advancing the second catheter into a left atrium through an interatrial septum such that the first catheter is in the right atrium;
    applying a force to compress a portion of the septum between the atraumatic electrode and the dilator; and
    cutting the compressed portion of the septum by delivering an ablation waveform to the atraumatic electrode such that a cut portion of the septum is held within the lumen.

2. The method of claim 1, wherein applying the force compresses the portion of the septum in a static equilibrium state.

3. The method of claim 1, wherein the septum is intact after applying the force to compress the portion of the septum.

4. The method of claim 1, wherein applying the force compresses the portion of the septum with a shear force.

5. The method of claim 4, wherein the shear force comprises a radial component.

6. The method of claim 1, wherein the septum is intact prior to delivery of the ablation waveform.

7. The method of claim 1, further comprising selecting an amount of the force between about 10 N and about 20 N to compress the septum using an actuation mechanism coupled to the second catheter.

8. The method of claim 7, wherein the actuation mechanism comprises a screw mechanism comprising a plurality of predetermined stops.

9. The method of claim 1, wherein compressing the portion of the septum comprises holding the portion of the septum in place relative to the first and second catheter.

10. The method of claim 1, wherein compressing the portion of the septum comprises engaging the portion of the septum to a mating surface of the second catheter.

11. The method of claim 1, wherein cutting the compressed portion by delivering the ablation waveform comprises forming an anastomosis in the septum comprising a diameter of between about 1 mm and about 1.5 cm.

12. The method of claim 1, wherein the ablation waveform comprises a two-phase waveform.

13. The method of claim 1, wherein the ablation waveform comprises a first waveform followed by a second waveform, the first waveform comprising a first voltage and the second waveform comprising a second voltage, and the first voltage higher than the second voltage.

14. The method of claim 1, wherein the ablation waveform comprises a current between about 50 mA and about 4 A, a voltage of between about 0.1 kV and about 4.0 kV, and a frequency of up to about 500 kHz.

15. The method of claim 1, further comprising tenting the septum over the second catheter and into the lumen by withdrawing the second catheter towards the first catheter.

16. The method of claim 1, wherein the barb comprises a rigid barb.

17. The method of claim 15, wherein tenting the septum comprises holding the atraumatic electrode in a substantially fixed position while withdrawing the second catheter towards the first catheter.

18. The method of claim 15, wherein tenting the septum comprises withdrawing a portion of the dilator into the lumen.

19. The method of claim 15, wherein tenting the septum forms a substantially conical or cylindrical shape.

20. The method of claim 1, wherein the barb comprises a projection coupled to the base portion, wherein the base portion couples the projection to the second catheter, and the base portion spaces the projection proximally from the dilator.

21. The method of claim 20, wherein the projection comprises a first portion of the projection coupled substantially perpendicularly to the base portion and a second portion of the projection coupled substantially perpendicular to the first portion of the projection, wherein tenting the first portion of the septum comprises piercing the first portion of the septum using the second portion of the projection.

22. The method of claim 20, wherein the projection is coupled proximal to the base portion.

23. The method of claim 15, wherein tenting the septum comprises piercing the septum with the barb.

24. The method of claim 1, wherein a proximal portion of the dilator comprises a first step portion comprising a first diameter and a second step portion comprising a second diameter greater than the first diameter, the first step portion proximal to the second step portion.

25. The method of claim 24, wherein the second step comprises a mating surface configured to engage an atraumatic distal end of the electrode.

26. The method of claim 1, wherein the force comprises a preload force.

27. The method of claim 1, wherein the atraumatic electrode comprises a blunt distal end.

\* \* \* \* \*